(12) United States Patent
Kumar et al.

(10) Patent No.: US 9,739,779 B2
(45) Date of Patent: Aug. 22, 2017

(54) METHODS OF SCREENING FOR JANUS KINASE 3 INTERACTING COMPOUNDS

(71) Applicants: Narendra Kumar, Kingsville, TX (US); Jayshree Mishra, Kingsville, TX (US)

(72) Inventors: Narendra Kumar, Kingsville, TX (US); Jayshree Mishra, Kingsville, TX (US)

(*) Notice: Subject to any disclaimer, the term of this patent is extended or adjusted under 35 U.S.C. 154(b) by 0 days.

(21) Appl. No.: 15/135,950

(22) Filed: Apr. 22, 2016

(65) Prior Publication Data

US 2016/0223545 A1 Aug. 4, 2016

Related U.S. Application Data

(63) Continuation-in-part of application No. 14/483,622, filed on Sep. 11, 2014, now abandoned.

(60) Provisional application No. 61/960,652, filed on Sep. 23, 2013.

(51) Int. Cl.
*G01N 33/53* (2006.01)
*G01N 33/573* (2006.01)
*C12Q 1/48* (2006.01)

(52) U.S. Cl.
CPC .......... *G01N 33/573* (2013.01); *C12Q 1/485* (2013.01); *C07K 2319/23* (2013.01); *G01N 2333/912* (2013.01); *G01N 2500/04* (2013.01)

(58) Field of Classification Search
None
See application file for complete search history.

(56) References Cited

U.S. PATENT DOCUMENTS

2006/0030018 A1* 2/2006 Zuccola ............... C12N 9/1205
435/194
2014/0065153 A1* 3/2014 Christiano ............ A61K 31/519
424/139.1

* cited by examiner

*Primary Examiner* — Jacob Cheu
(74) *Attorney, Agent, or Firm* — Benjamin Aaron Adler

(57) ABSTRACT

The present invention provides a method for screening compounds for their ability to inhibit autophosphorylation of Janus kinase 3 in the absence of any additional substrate. The present invention also provides a method for screening compounds that bind to Janus kinase 3 domains other than the kinase domain, to identify synthetic or natural compounds including biomolecules, that modulate Janus kinase 3 activity. This invention also describes a multi-component screening kit composed of purified recombinant Janus kinase 3 proteins and recombinant phosphorylated Janus kinase 3 fusion proteins including, one or more phosphorylated or non-phosphorylated domain-deleted Janus kinase 3 fusion proteins.

15 Claims, 13 Drawing Sheets

```
ATGGCACCTCCAAGTGAGGAGACACCTTCTGATCCCTCAGCGCTCTTGCAGCCTCTCATCCTCAGA
GGCAGGAGCCCTGCATGTGCTCCTTCCTCCCCGGGGACCTGGGCCTCCCCAGCGATTGTCATTCTC
TTTTGGGGACTACTTGGCTGAGGATTTATGTGTGCGAGCTGCCAAGGCCTGTGGCATCCTGCCTGT
TTATCATTCGCTTTTCGCTCTGGCCACTGAGGACTTCTCTTGCTGGTTTCCCCAAGCCACATCTT
CTGCATAGAGGACGTGGACACTCAAGTCTTGGTCTACAGGCTACGCTTTTATTTCCCTGACTGGTT
TGGGCTGGAGACATGTCACCGCTTTGGGCTGCGCAAAGATTTGACCAGTGCCATCCTTGACTTACA
TGTTTTAGAACATCTCTTTGCTCAGCACCGCAGTGACCTGGTGAGTGGGCGCCTCCCGGTGGGCCT
TAGCATGAAGGAGCAGGGAGAGTTCCTGAGCCTGGCCGTGCTGGACTTGGCCCAGATGGCTCGTGA
GCAGGCCCAGCGCCCAGGAGAGCTGCTGAAGACGGTCAGTTACAAAGCCTGTCTGCCGCCCAGCCT
GCGCGATGTGATCCAGGGCCAGAACTTCGTGACACGCAGGCGCATCCGCAGGACCGTGGTCTTGGC
GCTGCGCCGTGTGGTCGCCTGCCAGGCCGACCGCTACGCGCTCATGGCCAAGTATATTCTGGACCT
GGAGCGGCTACATCCAGCGGCCACCACCGAGACCTTCCGTGTGGGGCTCCCGGGCGCCCAGGAGGA
GCCGGGGCTTCTGCGTGTGGCGGGGGACAACGGCATCTCCTGGAGCTCCGGGGACCAGGAGCTTTT
CCAGACCTTCTGTGACTTTCCGGAAATCGTGGATGTCAGCATCAAGCAGGCCCCACGTGTGGGTCC
GGCAGGGGAGCACCGGCTGGTCACTGTCACCAGGATGGACGGCCACATCCTGGAAGCGGAGTTTCC
GGGGCTGCCTGAGGCGCTGTCTTTCGTGGCCCTCGTGGATGGGTACTTCCGCCTGATCTGCGACTC
CAGGCATTATTTCTGCAAGGAGGTGGCGCCGCCACGGCTGCTGGAGGAGGAGGCGGAGCTGTGCCA
TGGACCCATCACGTTAGACTTTGCCATCCACAAGCTGAAGGCCGCTGGCTCCCTCCCAGGCACCTA
TATTCTCCGCCGCAGCCCGCAGGACTATGACAGCTTTCTTCTTACCGCCTGCGTCCAGACTCCTCT
TGGCCCCGACTACAAGGGCTGCCTCATCCGCCAGGACCCCAGCGGGGCTTTCTCCCTGGTTGGCCT
CAGCCAGCCCCACAGAAGCCTGCGGGAGCTGCTTGCAGCCTGCTGGAATTCTGGGCTGCGAGTAGA
CGGTGCTGCCCTGAACCTAACATCCTGCTGCGCTCCCAGACCCAAGGAAAAGTCCAATTTGATCGT
GGTGCGAAGGGGCTGCACCCCCGCGCCTGCCCCTGGCTGCTCCCGTCCTGCTGTGCGCTGACACA
GCTGAGCTTCCACACAATTCCAACGGACAGCCTGGAGTGGCACGAGAACCTGGGTCACGGTTCTTT
TACCAAGATCTTCGTGGCCGCAGGCGGGAGGTCGTGGATGGTGAGACACATGACTCGGAAGTCCT
CCTGAAGGTCATGGACTCCAGACATCGGAACTGCATGGAGTCTTTTCTGGAAGCCGCAAGCTTGAT
GAGCCAAGTATCCTACCCGCACCTGGTGTTACTGCACGGCGTCTGCATGGCTGGAGACAGCATCAT
GGTGCAGGAATTTGTGTATCTAGGAGCAATTGACATGTACCTGCGCAAGCGTGGCCACCTGGTGTC
AGCCAGCTGGAAACTGCAGGTGACCAAGCAGCTGGCATATGCCCTTAACTACTTGGAGGACAAAGG
CCTTCCTCACGGCAACGTCTCAGCACGGAAGGTGCTCCTGGCTCGTGAGGGGGTGATGGGAATCC
ACCTTTCATTAAGCTGAGTGATCCTGGTGTCAGTCCCACTGTGCTGAGCCTGGAAATGCTCACCGA
CAGAATACCCTGGGTGGCCCCCGAATGTCTCCAGGAGGCTCAGACACTCTGCTTGGAGGCTGACAA
GTGGGGCTTTGGAGCCACCACGTGGGAGGTGTTCAGCGGGGGACCCGCCCACATCACCTCGCTGGA
GCCCGCCAAAAAGCTGAAGTTCTATGAGGACCAGGGACAGCTGCCCGCTCTCAAATGGACAGAACT
GGCGGGACTTATCACACAGTGCATGGCGTATGATCCTGGCCGGCGCCCCTCCTTCCGAGCTATCCT
CAGAGACCTCAACGGCCTCATTACATCAGATTACGAGCTCCTCTCAGACCCCACACCTGGCATCCC
GAGTCCTCGAGATGAGCTGTGCGGTGGCGCCCAGCTCTATGCCTGCCAGGACCCCGCCATATTCGA
GGAGAGACACCTTAAGTACATCTCTTTGCTGGGCAAGGGCAACTTTGGCAGCGTGGAGCTGTGCCG
CTATGACCCCCTGGGGGACAATACGGGACCCCTGGTGGCAGTGAAACAGCTACAGCACAGCGGGCC
AGACCAGCAGAGGGACTTCCAGCGGGAGATTCAGATCCTTAAGGCTCTGCACAGCGACTTCATCGT
CAAGTACCGGGGAGTCAGCTATGGGCCAGGTCGCCAGAGCCTGCGGTTGGTGATGGAGTACCTGCC
CAGCGGCTGCCTGCGAGACTTCCTGCAGCGCCATCGCGCGCGCCTGCACACCGACCGCCTACTGCT
GTTCGCTTGGCAGATCTGCAAGGGCATGGAGTACCTGGGTGCGCGCCGCTGCGTACACCGTGACCT
GGCTGCGCAACATCTTGGTGGAGAGCGAGGCTCATGTGAAGATCGCGGACTTCGGCCTCGCTAA
GCTGCTGCCCCTGGGAAAGGACTACTACGTGGTCCGCGAGCCTGGCCAAAGCCCCATCTTTTGGTA
TGCCCCGGAGTCCCTATCTGACAACATCTTCTCCCGCCAATCTGACGTGTGGAGCTTCGGAGTGGT
GTTGTACGAGCTCTTCACCTACTGCGACAAGAGCTGCAGCCCATCCGCTGAGTTCCTGCGCATGAT
GGGGCCTGAGCGTGAAGGACCCCGCTCTGCCGCCTCCTGGAGCTGCTGGCAGAGGGCCGACGCCT
CCCACCACCTCCCACCTGCCCCACCGAGGTTCAGGAGCTCATGCAGCTGTGCTGGGCGCCCAGCCC
GCACGACCGGCCAGCCTTCGGCACCCTGAGCCCCAGCTGGACGCGCTGTGGCGTGGAAGACCCGG
ATAGCAGCCAGGGGCGAGAGTGAGCTTGGTTCCTATGATCGGCTGTGTGACCTCAGGCAGGAAAC
TGTCCCTTTCTGGGCCCCATCACCCCCTTATCCCCTCTGGCCACTCCTTCCCATCATTCTTTCTTC
CCAGAATGGGGATATTAAATATGTGAGGCCGCATCGTGACTGACTGA
```

SEQ ID NO: 1

FIG. 1A

```
AGTATTCATGTCCCCTATACTAGGTTATTGGAAAATTAAGGGCCTTGTGCAACCCACTCGACTTCTTTTGGA
ATATCTTGAAGAAAAATATGAAGAGCATTTGTATGAGCGCGATGAAGGTGATAAATGGCGAAACAAAAAGTT
TGAATTGGGTTTGGAGTTTCCCAATCTTCCTTATTATATTGATGGTGATGTTAAATTAACACAGTCTATGGC
CATCATACGTTATATAGCTGACAAGCACAACATGTTGGGTGGTTGTCCAAAAGAGCGTGCAGAGATTTCAAT
GCTTGAAGGAGCGGTTTTGGATATTAGATACGGTGTTTCGAGAATTGCATATAGTAAAGACTTTGAAACTCT
CAAAGTTGATTTTCTTAGCAAGCTACCTGAAATGCTGAAAATGTTCGAAGATCGTTTATGTCATAAAACATA
TTTAAATGGTGATCATGTAACCCATCCTGACTTCATGTTGTATGACGCTCTTGATGTTGTTTTATACATGGA
CCCAATGTGCCTGGATGCGTTCCCAAAATTAGTTTGTTTTAAAAAACGTATTGAAGCTATCCCACAAATTGA
TAAGTACTTGAAATCCAGCAAGTATATAGCATGGCCTTTGCAGGGCTGGCAAGCCACGTTTGGTGGTGGCGA
CCATCCTCCAAAATCGGATCTGGTTCCGCGTGGATCCCCGAATTCCATGGCACCTCCAAGTGAGGAGACACC
TCTGATCCCTCAGCGCTCTTGCAGCCTCTCATCCTCAGAGGCAGGAGCCCTGCATGTGCTCCTTCCTCCCCG
GGGACCTGGGCCTCCCCAGCGATTGTCATTCTCTTTTGGGGACTACTTGGCTGAGGATTTATGTGTGCGAGC
TGCCAAGGCCTGTGGCATCCTGCCTGTTTATCATTCGCTTTTCGCTCTGGCCACTGAGGACTTCTCTTGCTG
GTTTCCCCCAAGCCACATCTTCTGCATAGAGGACGTGGACACTCAAGTCTTGGTCTACAGGCTACGCTTTTA
TTTCCCTGACTGGTTTGGGCTGGAGACATGTCACCGCTTTGGGCTGCGCAAAGATTTGACCAGTGCCATCCT
TGACTTACATGTTTTAGAACATCTCTTTGCTCAGCACCGCAGTGACCTGGTGAGTGGGCGCCTCCCGGTGGG
CCTTAGCATGAAGGAGCAGGGAGAGTTCCTGAGCCTGGCCGTGCTGGACTTGGCCCAGATGGCTCGTGAGCA
GGCCCAGCGCCCAGGAGAGCTGCTGAAGACGGTCAGTTACAAAGCCTGTCTGCCGCCCAGCCTGCGCGATGT
GATCCAGGGCCAGAACTTCGTGACACGCAGGCGCATCCGCAGGACCGTGGTCTTGGCGCTGCGCCGTGTGGT
CGCCTGCCAGGCCGACCGCTACGCGCTCATGGCCAAGTATATTCTGGACCTGGAGCGGCTACATCCAGCGGC
CACCACCGAGACCTTCCGTGTGGGGCTCCCGGGCGCCCAGGAGGAGCCGGGGCTTCTGCGTGTGGCGGGGGA
CAACGGCATCTCCTGGAGCTCCGGGGACCAGGAGCTTTTCCAGACCTTCTGTGACTTTCCGGAAATCGTGGA
TGTCAGCATCAAGCAGGCCCCACGTGTGGGTCCGCAGGGGAGCACCGGCTGGTCACTGTCACCAGGATGGA
CGGCCACATCCTGGAAGCGGAGTTTCCGGGGCTGCCTGAGGCGCTGTCTTTCGTGGCCCTCGTGGATGGGTA
CTTCCGCCTGATCTGCGACTCCAGGCATTATTTCTGCAAGGAGGTGGCGCCGCCACGGCTGCTGGAGGAGGA
GGCGGAGCTGTGCCATGGACCCATCACGTTAGACTTTGCCATCCACAAGCTGAAGGCCGCTGGCTCCCTCCC
AGGCACCTATATTCTCCGCCGCAGCCCGCAGGACTATGACAGCTTTCTTCTTACCGCCTGCGTCCAGACTCC
TCTTGGCCCCGACTACAAGGGCTGCCTCATCCGCCAGGACCCCAGCGGGGCTTTCTCCCTGGTTGGCCTCAG
CCAGCCCCACAGAAGCCTGCGGGAGCTGCTTGCAGCCTGCTGGAATTCTGGGCTGCGAGTAGACGGTGCTGC
CCTGAACCTAACATCCTGCTGCGCTCCAGACCCAAGGAAAAGTCCAATTTGATCGTGGTGCGAAGGGGCTG
CACCCCCGCGCCTGCCCCTGGCTGCTCCCCGTCCTGCTGTGCGCTGACACAGCTGAGCTTCCACACAATTCC
AACGGACAGCCTGGAGTGGCACGAGAACCTGGGTCACGGTTCTTTTACCAAGATCTTCCGTGGCCGCAGGCG
GGAGGTCGTGGATGGTGAGACACATGACTCGGAAGTCCTCCTGAAGGTCATGGACTCCAGACATCGGAACTG
CATGGAGTCTTTTCTGGAAGCCGCAAGCTTGATGAGCCAAGTATCCTACCCGCACCTGGTGTTACTGCACGG
CGTCTGCATGGCTGGAGACAGCATCATGGTGCAGGAATTTGTGTATCTAGGAGCAATTGACATGTACCTGCG
CAAGCGTGGCCACCTGGTGTCAGCAGCTGGAAACTGCAGGTGACCAAGCAGCTGGCATATGCCCTTAACTA
CTTGGAGGACAAAGGCCTTCCTCACGGCAACGTCTCAGCACGGAAGGTGCTCCTGGCTCGTGAGGGGGTGA
TGGGAATCCACCTTTCATTAAGCTGAGTGATCCTGGTGTCAGTCCCACTGTGCTGAGCCTGGAAATGCTCAC
CGACAGAATACCCTGGGTGGCCCCCGAATGTCTCCAGGAGGCTCAGACACTCTGCTTGGAGGCTGACAAGTG
GGGCTTTGGAGCCACCACGTGGGAGGTGTTCAGCGGGGACCCGCCCACATCACCTCGCTGGAGCCCGCCAA
AAAGCTGAAGTTCTATGAGGACCAGGGACAGCTGCCCGCTCTCAAATGGACAGAACTGGCGGACTTATCAC
ACAGTGCATGGCGTATGATCCTGGCCGGCGCCCCTCCTTCCGAGCTATCCTCAGAGACCTCAACGGCCTCAT
TACATCAGATTACGAGCTCCTCTCAGACCCCACACCTGGCATCCCGAGTCCTCGAGATGAGCTGTGCGGTGG
CGCCCAGCTCTATGCCTGCCAGGACCCCGCCATATTCGAGGAGAGACACCTTAAGTACATCTCTTTGCTGGG
CAAGGGCAACTTTGGCAGCGTGGAGCTGTGCCGCTATGACCCCCTGGGGGACAATACGGGACCCCTGGTGGC
AGTGAAACAGCTACAGCACAGCGGGCCAGACCAGCAGAGGGACTTCCAGCGGGAGATTCAGATCCTTAAGGC
TCTGCACAGCGACTTCATCGTCAAGTACCGGGGAGTCAGCTATGGGCCAGGTCGCCAGAGCCTGCGGTTGGT
GATGGAGTACCTGCCCAGCGGCTGCCTGCGAGACTTCCTGCAGCGCCATCGCGCGCCTGCACACCGACCG
CCTACTGCTGTTCGCTTGGCAGATCTGCAAGGGCATGGATACCTGGGTGCGCGCCGCTGCGTACACCGTGA
CCTGGCTGCGCGCAACATCTTGGTGGAGAGCGAGGCTCATGTGAAGATCGCGGACTTCGGCCTCGCTAAGCT
GCTGCCCCTGGGAAAGGACTACTACGTGGTCCGCGAGCCTGGCCAAAGCCCCATCTTTTGGTATGCCCCGGA
GTCCCTATCTGACAACATCTTCTCCCGCCAATCTGACGTGTGGAGCTTCGGAGTGGTGTTGTACGAGCTCTT
CACCTACTGCGACAAGAGCTGCAGCCCATCCGCTGAGTTCCTGCGCATGATGGGCCTGAGCGTGAAGGACC
CCGCTCTGCCGCCTCCTGGAGCTGCTGGCAGAGGGCCGACGCCTCCCACCACCTCCCACCTGCCCCACCGA
GGTTCAGGAGCTCATGCAGCTGTGCTGGGCGCCCAGCCCGCACGACCGGCCAGCCTTCGGCACCCTGAGCCC
CCAGCTGGACGCGCTGTGGCGTGGAAGACCCGGATAGCAGCCAGGGGCGAGAGTGAGCTTGGTTCCTATGAT
CTGGCTGTGTGACCTCAGGCAGGAAACTGTCCCTTTCTGGGCCCCATCACCCCCTTATCCCCTCTGGCCACT
CCTTCCCATCATTCTTTCTTCCCAGAATGGGGATATTAAATATGTGAGGCCGCATCGTGACTGACTGA
```

SEQ ID NO: 2

FIG. 1B

```
AGTATTCATGTCCCCTATACTAGGTTATTGGAAAATTAAGGGCCTTGTGCAACCCACTCGACTTCT
TTTGGAATATCTTGAAGAAAAATATGAAGAGCATTTGTATGAGCGCGATGAAGGTGATAAATGGCG
AAACAAAAAGTTTGAATTGGGTTTGGAGTTTCCCAATCTTCCTTATTATATTGATGGTGATGTTAA
ATTAACACAGTCTATGGCCATCATACGTTATATAGCTGACAAGCACAACATGTTGGGTGGTTGTCC
AAAAGAGCGTGCAGAGATTTCAATGCTTGAAGGAGCGGTTTTGGATATTAGATACGGTGTTTCGAG
AATTGCATATAGTAAAGACTTTGAAACTCTCAAAGTTGATTTTCTTAGCAAGCTACCTGAAATGCT
GAAAATGTTCGAAGATCGTTTATGTCATAAAACATATTTAAATGGTGATCATGTAACCCATCCTGA
CTTCATGTTGTATGACGCTCTTGATGTTGTTTTATACATGGACCCAATGTGCCTGGATGCGTTCCC
AAAATTAGTTTGTTTTAAAAAACGTATTGAAGCTATCCCACAAATTGATAAGTACTTGAAATCCAG
CAAGTATATAGCATGGCCTTTGCAGGGCTGGCAAGCCACGTTTGGTGGTGGCGACCATCCTCCAAA
ATCGGATCTGGTTCCGCGTGGATCCCCGAATTCCATGGCACCTCCAAGTGAGGAGACACCTCTGAT
CCCTCAGCGCTCTTGCAGCCTCTCATCCTCAGAGGCAGGAGCCCTGCATGTGCTCCTTCCTCCCCG
GGGACCTGGGCCTCCCCAGCGATTGTCATTCTCTTTTGGGGACTACTTGGCTGAGGATTTATGTGT
GCGAGCTGCCAAGGCCTGTGGCATCCTGCCTGTTTATCATTCGCTTTTCGCTCTGGCCACTGAGGA
CTTCTCTTGCTGGTTTCCCCCAAGCCACATCTTCTGCATAGAGGACGTGGACACTCAAGTCTTGGT
CTACAGGCTACGCTTTTATTTCCCTGACTGGTTTGGGCTGGAGACATGTCACCGCTTTGGGCTGCG
CAAAGATTTGACCAGTGCCATCCTTGACTTACATGTTTTAGAACATCTCTTTGCTCAGCACCGCAG
TGACCTGGTGAGTGGGCGCCTCCCGGTGGGCCTTAGCATGAAGGAGCAGGGAGAGTTCCTGAGCCT
GGCCGTGCTGGACTTGGCCCAGATGGCTCGTGAGCAGGCCCAGCGCCCAGGAGAGCTGCTGAAGAC
GGTCAGTTACAAAGCCTGTCTGCCGCCCAGCCTGCGCGATGTGATCCAGGGCCAGAACTTCGTGAC
ACGCAGGCGCATCCGCAGGACCGTGGTCTTGGCGCTGCGCCGTGTGGTCGCCTGCCAGGCCGACCG
CTACGCGCTCATGGCCAAGTATATTCTGGACCTGGAGCGGCTACATCCAGCGGCCACCACCGAGAC
CTTCCGTGTGGGGCTCCCGGGCGCCCAGGAGGAGCCGGGGCTTCTGCGTGTGGCGGGGACAACGG
CATCTCCTGGAGCTCCGGGGACCAGGAGCTTTTCCAGACCTTCTGTGACTTTCCGGAAATCGTGGA
TGTCAGCATCAAGCAGGCCCCACGTGTGGGTCCGGCAGGGGAGCACCGGCTGGTCACTGTCACCAG
GATGGACGGCCACATCCTGGAAGCGGAGTTTCCGGGGCTGCCTGAGGCGCTGTCTTTCGTGGCCCT
CGTGGATGGGTACTTCCGCCTGATCTGCGACTCCAGGCATTATTTCTGCAAGGAGGTGGCGCCGCC
ACGGCTGCTGGAGGAGGAGGCGGAGCTGTGCCATGGACCCATCACGTTAGACTTTGCCATCCACAA
GCTGAAGGCCGCTGGCTCCCTCCCAGGCACCTATATTCTCCGCCGCAGCCCGCAGGACTATGACAG
CTTTCTTCTTACCGCCTGCGTCCAGACTCCTCTTGGCCCCGACTACAAGGGCTGCCTCATCCGCCA
GGACCCCAGCGGGGCTTTCTCCCTGGTTGGCCTCAGCCAGCCCCACAGAAGCCTGCGGGAGCTGCT
TGCAGCCTGCTGGAATTCTGGGCTGCGAGTAGACGGTGCTGCCCTGAACCTAACATCCTGCTGCGC
TCCCAGACCCAAGGAAAAGTCCAATTTGATCGTGGTGCGAAGGGGCTGCACCCCCGCGCCTGCCCC
TGGCTGCTCCCCGTCCTGCTGTGCGCTGACACAGCTGAGCTTCCACACAATTCCAACGGACAGCCT
GGAGTGGCACGAGAACCTGGGTCACGGTTCTTTTACCAAGATCTTCCGTGGCCGCAGGCGGGAGGT
CGTGGATGGTGAGACACATGACTCGGAAGTCCTCCTGAAGGTCATGGACTCCAGACATCGGAACTG
CATGGAGTCTTTTCTGGAAGCCGCAAGCTTGATGAGCCAAGTATCCTACCCGCACCTGGTGTTACT
GCACGGCGTCTGCATGGCTGGAGACAGCATCATGGTGCAGGAATTTGTGTATCTAGGAGCAATTGA
CATGTACCTGCGCAAGCGTGGCCACCTGGTGTCAGCCAGCTGGAAACTGCAGGTGACCAAGCAGCT
GGCATATGCCCTTAACTACTTGGAGGACAAAGGCCTTCCTCACGGCAACGTCTCAGCACGGAAGGT
GCTCCTGGCTCGTGAGGGGGGTGATGGGAATCCACCTTTCATTAAGCTGAGTGATCCTGGTGTCAG
TCCCACTGTGCTGAGCCTGGAAATGCTCACCGACAGAATACCCTGGGTGGCCCCGAATGTCTCCA
GGAGGCTCAGACACTCTGCTTGGAGGCTGACAAGTGGGGCTTTGGAGCCACCACGTGGGAGGTGTT
CAGCGGGGGACCCGCCCACATCACCTCGCTGGAGCCCGCCAAAAAGCTGAAGTTCTATGAGGACCA
GGGACAGCTGCCCGCTCTCAAATGGACAGAACTGGCGGGACTTATCACACAGTGCATGGCGTATGA
TCCTGGCCGGCGCCCCTCCTTCCGAGCTATCCTCAGAGACCTCAACGGCCTCATTACATCAGATTA
CGAGCTCCTCTCAGACCCCTAGCCTGGCATCCCGAGTCCTCGAGATGAGCTGTGCGGTGGCGCCCA
GCTCTATGCCTGCCAGGA
```

SEQ ID NO: 3

FIG. 1C

```
AGTATTCATGTCCCCTATACTAGGTTATTGGAAAATTAAGGGCCTTGTGCAACCCACTCGACTTCT
TTTGGAATATCTTGAAGAAAAATATGAAGAGCATTTGTATGAGCGCGATGAAGGTGATAAATGGCG
AAACAAAAAGTTTGAATTGGGTTTGGAGTTTCCCAATCTTCCTTATTATATTGATGGTGATGTTAA
ATTAACACAGTCTATGGCCATCATACGTTATATAGCTGACAAGCACAACATGTTGGGTGGTTGTCC
AAAAGAGCGTGCAGAGATTTCAATGCTTGAAGGAGCGGTTTTGGATATTAGATACGGTGTTTCGAG
AATTGCATATAGTAAAGACTTTGAAACTCTCAAAGTTGATTTTCTTAGCAAGCTACCTGAAATGCT
GAAAATGTTCGAAGATCGTTTATGTCATAAAACATATTTAAATGGTGATCATGTAACCCATCCTGA
CTTCATGTTGTATGACGCTCTTGATGTTGTTTTATACATGGACCCAATGTGCCTGGATGCGTTCCC
AAAATTAGTTTGTTTTAAAAAACGTATTGAAGCTATCCCACAAATTGATAAGTACTTGAAATCCAG
CAAGTATATAGCATGGCCTTTGCAGGGCTGGCAAGCCACGTTTGGTGGTGGCGACCATCCTCCAAA
ATCGGATCTGGTTCCGCGTGGATCCCCGAATTCCATGGCACCTCCAAGTGAGGAGACACCTCTGAT
CCCTCAGCGCTCTTGCAGCCTCTCATCCTCAGAGGCAGGAGCCCTGCATGTGCTCCTTCCTCCCCG
GGGACCTGGGCCTCCCCAGCGATTGTCATTCTCTTTTGGGGACTACTTGGCTGAGGATTTATGTGT
GCGAGCTGCCAAGGCCTGTGGCATCCTGCCTGTTTATCATTCGCTTTTCGCTCTGGCCACTGAGGA
CTTCTCTTGCTGGTTTCCCCCAAGCCACATCTTCTGCATAGAGGACGTGGACACTCAAGTCTTGGT
CTACAGGCTACGCTTTTATTTCCCTGACTGGTTTGGGCTGGAGACATGTCACCGCTTTGGGCTGCG
CAAAGATTTGACCAGTGCCATCCTTGACTTACATGTTTTAGAACATCTCTTTGCTCAGCACCGCAG
TGACCTGGTGAGTGGGCGCCTCCCGGTGGGCCTTAGCATGAAGGAGCAGGGAGAGTTCCTGAGCCT
GGCCGTGCTGGACTTGGCCCAGATGGCTCGTGAGCAGGCCCAGCGCCCAGGAGAGCTGCTGAAGAC
GGTCAGTTACAAAGCCTGTCTGCCGCCAGCCTGCGCGATGTGATCCAGGGCCAGAACTTCGTGAC
ACGCAGGCGCATCCGCAGGACCGTGGTCTTGGCGCTGCGCCGTGTGGTCGCCTGCCAGGCCGACCG
CTACGCGCTCATGGCCAAGTATATTCTGGACCTGGAGCGGCTACATCCAGCGGCCACCACCGAGAC
CTTCCGTGTGGGCTCCCGGGCGCCCAGGAGGAGCCGGGGCTTCTGCGTGTGGCGGGGGACAACGG
CATCTCCTGGAGCTCCGGGGACCAGGAGCTTTTCCAGACCTTCTGTGACTTTCCGGAAATCGTGGA
TGTCAGCATCAAGCAGGCCCCACGTGTGGGTCCGGCAGGGGAGCACCGGCTGGTCACTGTCACCAG
GATGGACGGCCACATCCTGGAAGCGGAGTTTCCGGGGCTGCCTGAGGCGCTGTCTTTCGTGGCCCT
CGTGGATGGGTACTTCCGCCTGATCTGCGACTCCAGGCATTATTTCTGCAAGGAGGTGGCGCCGCC
ACGGCTGCTGGAGGAGGAGGCGGAGCTGTGCCATGGACCCATCACGTTAGACTTTGCCATCCACAA
GCTGAAGGCCGCTGGCTCCCTCCCAGGCACCTATATTCTCCGCCGCAGCCCGCAGGACTATGACAG
CTTTCTTCTTACCGCCTGCGTCCAGACTCCTCTTGGCCCCGACTACAAGGGCTGCCTCATCCGCCA
GGACCCCAGCGGGGCTTTCTCCCTGGTTGGCCTCAGCCAGCCCCACAGAAGCCTGCGGGAGCTGCT
TGCAGCCTGCTGGAATTCTGGGCTGCGAGTAGACGGTGCTGCCCTGAACCTAACATCCTGCTGCGC
TCCCAGACCCAAGGAAAAGTCCAATTTGATCTAGGTGCGAAGGGGCTG
                                                      SEQ ID NO: 4
```

FIG. 1D

```
AGTATTCATGTCCCCTATACTAGGTTATTGGAAAATTAAGGGCCTTGTGCAACCCACTCGACTTCT
TTTGGAATATCTTGAAGAAAAATATGAAGAGCATTTGTATGAGCGCGATGAAGGTGATAAATGGCG
AAACAAAAAGTTTGAATTGGGTTTGGAGTTTCCCAATCTTCCTTATTATATTGATGGTGATGTTAA
ATTAACACAGTCTATGGCCATCATACGTTATATAGCTGACAAGCACAACATGTTGGGTGGTTGTCC
AAAAGAGCGTGCAGAGATTTCAATGCTTGAAGGAGCGGTTTTGGATATTAGATACGGTGTTTCGAG
AATTGCATATAGTAAAGACTTTGAAACTCTCAAAGTTGATTTTCTTAGCAAGCTACCTGAAATGCT
GAAAATGTTCGAAGATCGTTTATGTCATAAAACATATTTAAATGGTGATCATGTAACCCATCCTGA
CTTCATGTTGTATGACGCTCTTGATGTTGTTTTATACATGGACCCAATGTGCCTGGATGCGTTCCC
AAAATTAGTTTGTTTTAAAAAACGTATTGAAGCTATCCCACAAATTGATAAGTACTTGAAATCCAG
CAAGTATATAGCATGGCCTTTGCAGGGCTGGCAAGCCACGTTTGGTGGTGGCGACCATCCTCCAAA
ATCGGATCTGGTTCCGCGTGGATCCCCGAATTCCATGGCACCTCCAAGTGAGGAGACACCTCTGAT
CCCTCAGCGCTCTTGCAGCCTCTCATCCTCAGAGGCAGGAGCCCTGCATGTGCTCCTTCCTCCCCG
GGGACCTGGGCCTCCCCAGCGATTGTCATTCTCTTTTGGGGACTACTTGGCTGAGGATTTATGTGT
GCGAGCTGCCAAGGCCTGTGGCATCCTGCCTGTTTATCATTCGCTTTTCGCTCTGGCCACTGAGGA
CTTCTCTTGCTGGTTTCCCCCAAGCCACATCTTCTGCATAGAGGACGTGGACACTCAAGTCTTGGT
CTACAGGCTACGCTTTTATTTCCCTGACTGGTTTGGGCTGGAGACATGTCACCGCTTTGGGCTGCG
CAAAGATTTGACCAGTGCCATCCTTGACTTACATGTTTTAGAACATCTCTTTGCTCAGCACCGCAG
TGACCTGGTGAGTGGGCGCCTCCCGGTGGGCCTTAGCATGAAGGAGCAGGGAGAGTTCCTGAGCCT
GGCCGTGCTGGACTTGGCCCAGATGGCTCGTGAGCAGGCCCAGCGCCCAGGAGAGCTGCTGAAGAC
GGTCAGTTACAAAGCCTGTCTGCCGCCCAGCCTGCGCGATGTGATCCAGGGCCAGAACTTCGTGAC
ACGCAGGCGCATCCGCAGGACCGTGGTCTTGGCGCTGCGCCGTGTGGTCGCCTGCCAGGCCGACCG
CTACGCGCTCATGGCCAAGTATATTCTGGACCTGGAGCGGCTACATCCAGCGGCCACCACCGAGAC
CTTCCGTGTGTAGCTCCCGGGCGCCCAGGAGGAGCCGGGGCTTCTGCG
```

SEQ ID NO: 5

FIG. 1E

MAPPSEETPLIPQRSCSLSSSEAGALHVLLPPRGPGPPQRLSFSFGDYLAEDLCVRAAKACGILPV
YHSLFALATEDFSCWFPPSHIFCIEDVDTQVLVYRLRFYFPDWFGLETCHRFGLRKDLTSAILDLH
VLEHLFAQHRSDLVSGRLPVGLSMKEQGEFLSLAVLDLAQMAREQAQRPGELLKTVSYKACLPPSL
RDVIQGQNFVTRRRIRRTVVLALRRVVACQADRYALMAKYILDLERLHPAATTETFRVGLPGAQEE
PGLLRVAGDNGISWSSGDQELFQTFCDFPEIVDVSIKQAPRVGPAGEHRLVTVTRMDGHILEAEFP
GLPEALSFVALVDGYFRLICDSRHYFCKEVAPPRLLEEEAELCHGPITLDFAIHKLKAAGSLPGTY
ILRRSPQDYDSFLLTACVQTPLGPDYKGCLIRQDPSGAFSLVGLSQPHRSLRELLAACWNSGLRVD
GAALNLTSCCAPRPKEKSNLIVVRRGCTPAPAPGCSPSCCALTQLSFHTIPTDSLEWHENLGHGSF
TKIFRGRRREVVDGETHDSEVLLKVMDSRHRNCMESFLEAASLMSQVSYPHLVLLHGVCMAGDSIM
VQEFVYLGAIDMYLRKRGHLVSASWKLQVTKQLAYALNYLEDKGLPHGNVSARKVLLAREGGDGNP
PFIKLSDPGVSPTVLSLEMLTDRIPWVAPECLQEAQTLCLEADKWGFGATTWEVFSGGPAHITSLE
PAKKLKFYEDQGQLPALKWTELAGLITQCMAYDPGRRPSFRAILRDLNGLITSDYELLSDPTPGIP
SPRDELCGGAQLYACQDPAIFEERHLKYISLLGKGNFGSVELCRYDPLGDNTGPLVAVKQLQHSGP
DQQRDFQREIQILKALHSDFIVKYRGVSYGPGRQSLRLVMEYLPSGCLRDFLQRHRARLHTDRLLL
FAWQICKGMEYLGARRCVHRDLAARNILVESEAHVKIADFGLAKLLPLGKDYYVVREPGQSPIFWY
APESLSDNIFSRQSDVWSFGVVLYELFTYCDKSCSPSAEFLRMMGPEREGPPLCRLLELLAEGRRL
PPPPTCPTEVQELMQLCWAPSPHDRPAFGTLSPQLDALWRGRPG*

SEQ ID NO: 6

FIG. 2A

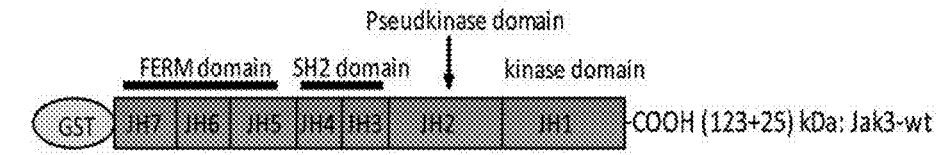

Pseudkinase domain
FERM domain   SH2 domain   ↓   kinase domain
GST JH7 JH6 JH5 JH4 JH3 JH2 JH1 -COOH (123+25) kDa: Jak3-wt VFMSPILGYWKIKGLVQPTRLLLEYLEEKYEEHLYERDEGDKWRNKKFELGLEFPNLPYYIDGD
VKLTQSMAIIRYIADKHNMLGGCPKERAEISMLEGAVLDIRYGVSRIAYSKDFETLKVDFLSKL
PEMLKMFEDRLCHKTYLNGDHVTHPDFMLYDALDVVLYMDPMCLDAFPKLVCFKKRIEAIPQID
KYLKSSKYIAWPLQGWQATFGGGDHPPKSDLVPRGSPNSMAPPSEETPLIPQRSCSLSSSEAGA
LHVLLPPRGPGPPQRLSFSFGDYLAEDLCVRAAKACGILPVYHSLFALATEDFSCWFPPSHIFC
IEDVDTQVLVYRLRFYFPDWFGLETCHRFGLRKDLTSAILDLHVLEHLFAQHRSDLVSGRLPVG
LSMKEQGEFLSLAVLDLAQMAREQAQRPGELLKTVSYKACLPPSLRDVIQGQNFVTRRRIRRTV
VLALRRVVACQADRYALMAKYILDLERLHPAATTETFRVGLPGAQEEPGLLRVAGDNGISWSSG
DQELFQTFCDFPEIVDVSIKQAPRVGPAGEHRLVTVTRMDGHILEAEFPGLPEALSFVALVDGY
FRLICDSRHYFCKEVAPPRLLEEEAELCHGPITLDFAIHKLKAAGSLPGTYILRRSPQDYDSFL
LTACVQTPLGPDYKGCLIRQDPSGAFSLVGLSQPHRSLRELLAACWNSGLRVDGAALNLTSCCA
PRPKEKSNLIVVRRGCTPAPAPGCSPSCCALTQLSFHTIPTDSLEWHENLGHGSFTKIFRGRRR
EVVDGETHDSEVLLKVMDSRHRNCMESFLEAASLMSQVSYPHLVLLHGVCMAGDSIMVQEFVYL
GAIDMYLRKRGHLVSASWKLQVTKQLAYALNYLEDKGLPHGNVSARKVLLAREGGDGNPPFIKL
SDPGVSPTVLSLEMLTDRIPWVAPECLQEAQTLCLEADKWGFGATTWEVFSGGPAHITSLEPAK
KLKFYEDQGQLPALKWTELAGLITQCMAYDPGRRPSFRAILRDLNGLITSDYELLSDPTPGIPS
PRDELCGGAQLYACQDPAIFEERHLKYISLLGKGNFGSVELCRYDPLGDNTGPLVAVKQLQHSG
PDQQRDFQREIQILKALHSDFIVKYRGVSYGPGRQSLRLVMEYLPSGCLRDFLQRHRARLHTDR
LLLFAWQICKGMEYLGARRCVHRDLAARNILVESEAHVKIADFGLAKLLPLGKDYYVVREPGQS
PIFWYAPESLSDNIFSRQSDVWSFGVVLYELFTYCDKSCSPSAEFLRMMGPEREGPPLCRLLEL
LAEGRRLPPPPTCPTEVQELMQLCWAPSPHDRPAFGTLSPQLDALWRGRPGQPGARVSLVPMIW
LCDLRQETVPFWAPSPPYPLWPLLPIILSSQNGDIKYVRPHRD*L SEQ ID NO: 7 (non-phosphorylated)
SEQ ID NO: 11 (phosphorylated)

FIG. 2B

VFMSPILGYWKIKGLVQPTRLLLEYLEEKYEEHLYERDEGDKWRNKKFELGLEFPNLPYYIDGDV
KLTQSMAIIRYIADKHNMLGGCPKERAEISMLEGAVLDIRYGVSRIAYSKDFETLKVDFLSKLPE
MLKMFEDRLCHKTYLNGDHVTHPDFMLYDALDVVLYMDPMCLDAFPKLVCFKKRIEAIPQIDKYL
KSSKYIAWPLQGWQATFGGGDHPPKSDLVPRGSPNSMAPPSEETPLIPQRSCSLSSSEAGALHVL
LPPRGPGPPQRLSFSFGDYLAEDLCVRAAKACGILPVYHSLFALATEDFSCWFPPSHIFCIEDVD
TQVLVYRLRFYFPDWFGLETCHRFGLRKDLTSAILDLHVLEHLFAQHRSDLVSGRLPVGLSMKEQ
GEFLSLAVLDLAQMAREQAQRPGELLKTVSYKACLPPSLRDVIQGQNFVTRRRIRRTVVLALRRV
VACQADRYALMAKYILDLERLHPAATTETFRVGLPGAQEEPGLLRVAGDNGISWSSGDQELFQTF
CDFPEIVDVSIKQAPRVGPAGEHRLVTVTRMDGHILEAEFPGLPEALSFVALVDGYFRLICDSRH
YFCKEVAPPRLLEEEAELCHGPITLDFAIHKLKAAGSLPGTYILRRSPQDYDSFLLTACVQTPLG
PDYKGCLIRQDPSGAFSLVGLSQPHRSLRELLAACWNSGLRVDGAALNLTSCCAPRPKEKSNLIV
VRRGCTPAPAPGCSPSCCALTQLSFHTIPTDSLEWHENLGHGSFTKIFRGRRREVVDGETHDSEV
LLKVMDSRHRNCMESFLEAASLMSQVSYPHLVLLHGVCMAGDSIMVQEFVYLGAIDMYLRKRGHL
VSASWKLQVTKQLAYALNYLEDKGLPHGNVSARKVLLAREGGDGNPPFIKLSDPGVSPTVLSLEM
LTDRIPWVAPECLQEAQTLCLEADKWGFGATTWEVFSGGPAHITSLEPAKKLKFYEDQGQLPALK
WTELAGLITQCMAYDPGRRPSFRAILRDLNGLITSDYELLSDP*PGIPSPRDELCG

SEQ ID NO: 8 (non-phosphorylated)
SEQ ID NO: 12 (phosphorylated)

FIG. 2C

VFMSPILGYWKIKGLVQPTRLLLEYLEEKYEEHLYERDEGDKWRNKKFELGLEFPNLPYYIDGD
VKLTQSMAIIRYIADKHNMLGGCPKERAEISMLEGAVLDIRYGVSRIAYSKDFETLKVDFLSKL
PEMLKMFEDRLCHKTYLNGDHVTHPDFMLYDALDVVLYMDPMCLDAFPKLVCFKKRIEAIPQID
KYLKSSKYIAWPLQGWQATFGGGDHPPKSDLVPRGSPNSMAPPSEETPLIPQRSCSLSSSEAGA
LHVLLPPRGPGPPQRLSFSFGDYLAEDLCVRAAKACGILPVYHSLFALATEDFSCWFPPSHIFC
IEDVDTQVLVYRLRFYFPDWFGLETCHRFGLRKDLTSAILDLHVLEHLFAQHRSDLVSGRLPVG
LSMKEQGEFLSLAVLDLAQMAREQAQRPGELLKTVSYKACLPPSLRDVIQGQNFVTRRRIRRTV
VLALRRVVACQADRYALMAKYILDLERLHPAATTETFRVGLPGAQEEPGLLRVAGDNGISWSSG
DQELFQTFCDFPEIVDVSIKQAPRVGPAGEHRLVTVTRMDGHILEAEFPGLPEALSFVALVDGY
FRLICDSRHYFCKEVAPPRLLEEEAELCHGPITLDFAIHKLKAAGSLPGTYILRRSPQDYDSFL
LTACVQTPLGPDYKGCLIRQDPSGAFSLVGLSQPHRSLRELLAACWNSGLRVDGAALNLTSCCA
PRPKEKSNLI*VRRGCTPAPAPG

SEQ ID NO: 9 (non-phosphorylated)
SEQ ID NO: 13 (phosphorylated)

FIG. 2D

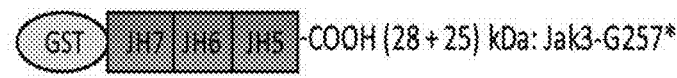 COOH (28 + 25) kDa: Jak3-G257*

```
VFMSPILGYWKIKGLVQPTRLLLEYLEEKYEEHLYERDEGDKWRNKKFELGLEFPNLPYYIDGDVK
LTQSMAIIRYIADKHNMLGGCPKERAEISMLEGAVLDIRYGVSRIAYSKDFETLKVDFLSKLPEML
KMFEDRLCHKTYLNGDHVTHPDFMLYDALDVVLYMDPMCLDAFPKLVCFKKRIEAIPQIDKYLKSS
KYIAWPLQGWQATFGGGDHPPKSDLVPRGSPNSMAPPSEETPLIPQRSCSLSSSEAGALHVLLPPR
GPGPPQRLSFSFGDYLAEDLCVRAAKACGILPVYHSLFALATEDFSCWFPPSHIFCIEDVDTQVLV
YRLRFYFPDWFGLETCHRFGLRKDLTSAILDLHVLEHLFAQHRSDLVSGRLPVGLSMKEQGEFLSL
AVLDLAQMAREQAQRPGELLKTVSYKACLPPSLRDVIQGQNFVTRRRIRRTVVLALRRVVACQADR
YALMAKYILDLERLHPAATTETFRV*LPGAQEEPGLLRVAG
```

SEQ ID NO: 10

FIG. 2E

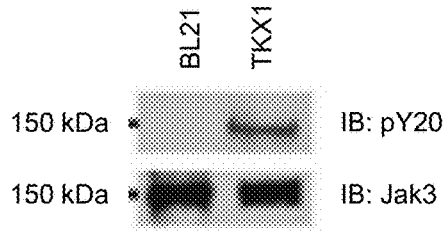

FIG. 3A

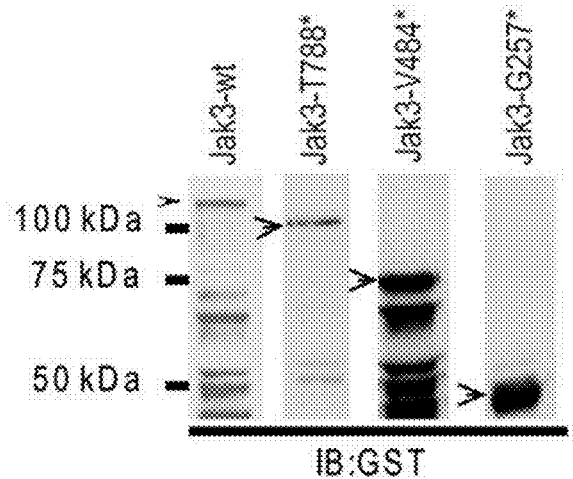

FIG. 3B

SEQUENCE LISTING

```
<160> NUMBER OF SEQ ID NOS: 13

<210> SEQ ID NO 1
<211> LENGTH: 3479
<212> TYPE: DNA
<213> ORGANISM: Artificial Sequence
<220> FEATURE:
<223> OTHER INFORMATION: cDNA sequence for recombinant Janus Kinase 3
      protein

<400> SEQUENCE: 1
atggcacctc caagtgagga gacaccttct gatccctcag cgctcttgca gcctctcatc      60
ctcagaggca ggagccctgc atgtgctcct tcctccccgg ggacctgggc ctccccagcg     120
attgtcattc tcttttgggg actacttggc tgaggattta tgtgtgcgag ctgccaaggc     180
ctgtggcatc ctgcctgttt atcattcgct tttcgctctg gccactgagg acttctcttg     240
ctggtttccc ccaagccaca tcttctgcat agaggacgtg gacactcaag tcttggtcta     300
caggctacgc tttatttcc ctgactggtt tgggctggag acatgtcacc gctttgggct     360
gcgcaaagat ttgaccagtg ccatccttga cttacatgtt ttagaacatc tctttgctca     420
gcaccgcagt gacctggtga gtgggcgcct cccggtgggc cttagcatga aggagcaggg     480
agagttcctg agcctggccg tgctggactt ggcccagatg gctcgtgagc aggcccagcg     540
cccaggagag ctgctgaaga cggtcagtta caaagcctgt ctgccgccca gctgcgcga     600 tgtgatccag ggccagaact tcgtgacacg caggcgcatc cgcaggaccg tggtcttggc     660
gctgcgccgt gtggtcgcct gccaggccga ccgctacgcg ctcatggcca agtatatttct     720 ggacctggag cggctacatc cagcggccac caccgagacc ttccgtgtgg ggctcccggg     780
cgcccaggag gagccggggc ttctgcgtgt ggcggggac aacggcatct cctggagctc     840
cggggaccag gagcttttcc agaccttctg tgactttccg gaaatcgtgg atgtcagcat     900
caagcaggcc ccacgtgtgg gtccggcagg ggagcaccgg ctggtcactg tcaccaggat     960
ggacggccac atcctggaag cggagtttcc gggggctgcct gaggcgctgt ctttcgtggc    1020
cctcgtggat gggtacttcc gcctgatctg cgactccagg cattatttct gcaaggaggt    1080
ggcgccgcca cggctgctgg aggaggaggc ggagctgtgc catggaccca tcacgttaga    1140
```

```
ctttgccatc cacaagctga aggccgctgg ctccctccca ggcacctata ttctccgccg   1200
cagcccgcag gactatgaca gctttcttct taccgcctgc gtccagactc ctcttggccc   1260
cgactacaag ggctgcctca tccgccagga ccccagcggg gctttctccc tggttggcct   1320
cagccagccc cacagaagcc tgcgggagct gcttgcagcc tgctggaatt ctgggctgcg   1380
agtagacggt gctgccctga acctaacatc ctgctgcgct cccagaccca aggaaaagtc   1440
caatttgatc gtggtgcgaa ggggctgcac ccccgcgcct gccccctggct gctcccccgtc   1500
ctgctgtgcg ctgacacagc tgagcttcca cacaattcca acggacagcc tggagtggca   1560
cgagaacctg ggtcacggtt cttttaccaa gatcttccgt ggccgcaggc gggaggtcgt   1620
ggatggtgag acacatgact cggaagtcct cctgaaggtc atggactcca gacatcggaa   1680
ctgcatggag tcttttctgg aagccgcaag cttgatgagc caagtatcct acccgcacct   1740
ggtgttactg cacggcgtct gcatggctgg agacagcatc atggtgcagg aatttgtgta   1800
tctaggagca attgacatgt acctgcgcaa gcgtggccac ctggtgtcag ccagctggaa   1860
actgcaggtg accaagcagc tggcatatgc ccttaactac ttggaggaca aaggccttcc   1920
tcacggcaac gtctcagcac ggaaggtgct cctggctcgt gagggggtg atgggaatcc   1980
acctttcatt aagctgagtg atcctggtgt cagtcccact gtgctgagcc tggaaatgct   2040
caccgacaga ataccctggg tggccccga atgtctccag gaggctcaga cactctgctt   2100
ggaggctgac aagtggggct ttggagccac acgtgggag gtgttcagcg ggggacccgc   2160
ccacatcacc tcgctggagc ccgccaaaaa gctgaagttc tatgaggacc agggacagct   2220
gcccgctctc aaatggacag aactggcggg acttatcaca cagtgcatgg cgtatgatcc   2280
tggccggcgc ccctccttcc gagctatcct cagagacctc aacggcctca ttacatcaga   2340
ttacgagctc ctctcagacc ccacacctgg catcccgagt cctcgagatg agctgtgcgg   2400
tggcgcccag ctctatgcct gccaggaccc cgccatattc gaggagagac accttaagta   2460
catctctttg ctgggcaagg gcaactttgg cagcgtggag ctgtgccgct atgaccccct   2520
gggggacaat acgggacccc tggtggcagt gaaaacagcta cagcacagcg ggccagacca   2580
gcagagggac ttccagcggg agattcagat ccttaaggct ctgcacagcg acttcatcgt   2640
caagtaccgg ggagtcagct atgggccagg tcgccagagc ctgcggttgg tgatggagta   2700
cctgcccagc ggctgcctgc gagacttcct gcagcgccat cgcgcgcgcc tgcacaccga   2760
ccgcctactg ctgttcgctt ggcagatctg caagggcatg gagtacctgg gtgcgcgccg   2820
ctgcgtacac cgtgacctgg ctgcgcgcaa catcttggtg gagagcgagg ctcatgtgaa   2880
gatcgcggac ttcggcctcg ctaagctgct gccccctggga aaggactact acgtggtccg   2940
cgagcctggc caaagcccca tcttttggta tgccccggag tccctatctg acaacatctt   3000
ctccccgccaa tctgacgtgt ggagcttcgg agtggtgttg tacgagctct tcacctactg   3060
cgacaagagc tgcagcccat ccgctgagtt cctgcgcatg atgggcctg agcgtgaagg   3120
acccccgctc tgccgcctcc tggagctgct ggcagagggc cgacgcctcc caccacctcc   3180
cacctgcccc accgaggttc aggagctcat gcagctgtgc tgggcgccca gcccgcacga   3240
ccggccagcc ttcggcaccc tgagccccca gctggacgcg ctgtggcgtg aagacccgg   3300
atagcagcca ggggcgagag tgagcttggt tcctatgatc tggctgtgtg acctcaggca   3360
ggaaactgtc ccttttctggg ccccatcacc cccttatccc ctctggccac tccttcccat   3420
cattctttct tcccagaatg gggatattaa atatgtgagg ccgcatcgtg actgactga   3479
```

```
<210> SEQ ID NO 2
<211> LENGTH: 4172
<212> TYPE: DNA
<213> ORGANISM: Artificial Sequence
<220> FEATURE:
<223> OTHER INFORMATION: cDNA sequence for Glutathione S-transferase-
      Janus Kinase 3 fusion protein

<400> SEQUENCE: 2
```

| | | | | | |
|---|---|---|---|---|---|
| agtattcatg | tcccctatac | taggttattg | gaaaattaag | ggccttgtgc | aacccactcg | 60 |
| acttcttttg | gaatatcttg | aagaaaaata | tgaagagcat | ttgtatgagc | gcgatgaagg | 120 |
| tgataaatgg | cgaaacaaaa | agtttgaatt | gggtttggag | tttcccaatc | ttccttatta | 180 |
| tattgatggt | gatgttaaat | taacacagtc | tatggccatc | atacgttata | tagctgacaa | 240 |
| gcacaacatg | ttgggtggtt | gtccaaaaga | gcgtgcagag | atttcaatgc | ttgaaggagc | 300 |
| ggttttggat | attagatacg | tgtgttcgag | aattgcatat | agtaaagact | tgaaactct | 360 |
| caaagttgat | tttcttagca | agctacctga | aatgctgaaa | atgttcgaag | atcgtttatg | 420 |
| tcataaaaca | tatttaaatg | gtgatcatgt | aacccatcct | gacttcatgt | tgtatgacgc | 480 |
| tcttgatgtt | gttttataca | tggacccaat | gtgcctggat | gcgttcccaa | aattagtttg | 540 |
| ttttaaaaaa | cgtattgaag | ctatcccaca | aattgataag | tacttgaaat | ccagcaagta | 600 |
| tatagcatgg | cctttgcagg | gctggcaagc | cacgtttggt | ggtggcgacc | atcctccaaa | 660 |
| atcggatctg | gttccgcgtg | gatccccgaa | ttccatggca | cctccaagtg | aggagacacc | 720 |
| tctgatccct | cagcgctctt | gcagcctctc | atcctcagag | gcaggagccc | tgcatgtgct | 780 |
| ccttcctccc | cggggacctg | ggcctcccca | gcgattgtca | ttctcttttg | gggactactt | 840 |
| ggctgaggat | ttatgtgtgc | gagctgccaa | ggcctgtggc | atcctgcctg | tttatcattc | 900 |
| gcttttcgct | ctggccactg | aggacttctc | ttgctggttt | cccccaagcc | acatcttctg | 960 |
| catagaggac | gtggacactc | aagtcttggt | ctacaggcta | cgcttttatt | tccctgactg | 1020 |
| gtttgggctg | gagacatgtc | accgctttgg | gctgcgcaaa | gatttgacca | gtgccatcct | 1080 |
| tgacttacat | gttttagaac | atctctttgc | tcagcaccgc | agtgacctgg | tgagtgggcg | 1140 |
| cctcccggtg | ggccttagca | tgaaggagca | gggagagttc | ctgagcctgg | ccgtgctgga | 1200 |
| cttggcccag | atggctcgtg | agcaggccca | gcgcccagga | gagctgctga | agacggtcag | 1260 |
| ttacaaagcc | tgtctgccgc | ccagcctgcg | cgatgtgatc | cagggccaga | acttcgtgac | 1320 |
| acgcaggcgc | atccgcagga | ccgtggtctt | ggcgctgcgc | cgtgtggtcg | cctgccaggc | 1380 |
| cgaccgctac | cgcgctcatg | gccaagtatat | tctggacctg | gagcggctac | atccagcggc | 1440 |
| caccaccgag | accttccgtg | tggggctccc | gggcgcccag | gaggagccgg | ggcttctgcg | 1500 |
| tgtggcgggg | gacaacggca | tctcctggag | ctccggggac | caggagcttt | tccagacctt | 1560 |
| ctgtgacttt | ccggaaatcg | tggatgtcag | catcaagcag | gccccacgtg | tgggtccggc | 1620 |
| agggagcac | cggctggtca | ctgtcaccag | gatggacggc | cacatcctgg | aagcggagtt | 1680 |
| tccggggctg | cctgaggcgc | tgtctttcgt | ggccctcgtg | gatgggtact | tccgcctgat | 1740 |
| ctgcgactcc | aggcattatt | tctgcaagga | ggtggcgccg | ccacggctgc | tggaggagga | 1800 |
| ggcggagctg | tgccatggac | ccatcacgtt | agactttgcc | atccacaagc | tgaaggccgc | 1860 |
| tggctcccctc | ccaggcacct | atattctccg | ccgcagcccg | caggactatg | acagctttct | 1920 |
| tcttaccgcc | tgcgtccaga | ctcctctttgg | ccccgactac | aagggctgcc | tcatccgcca | 1980 |
| ggaccccagc | ggggctttct | ccctggttgg | cctcagccag | cccacagaa | gcctgcggga | 2040 |
| gctgcttgca | gcctgctgga | attctgggct | gcgagtagac | ggtgctgccc | tgaacctaac | 2100 |

-continued

```
atcctgctgc gctcccagac ccaaggaaaa gtccaatttg atcgtggtgc gaagggctg    2160
cacccccgcg cctgcccctg gctgctcccc gtcctgctgt gcgctgacac agctgagctt   2220
ccacacaatt ccaacggaca gcctggagtg gcacgagaac ctgggtcacg gttcttttac   2280
caagatcttc cgtggccgca ggcgggaggt cgtggatggt gagacacatg actcggaagt   2340
cctcctgaag gtcatggact ccagacatcg gaactgcatg gagtcttttc tggaagccgc   2400
aagcttgatg agccaagtat cctacccgca cctggtgtta ctgcacggcg tctgcatggc   2460
tggagacagc atcatggtgc aggaatttgt gtatctagga gcaattgaca tgtacctgcg   2520
caagcgtggc cacctggtgt cagccagctg gaaactgcag gtgaccaagc agctggcata   2580
tgcccttaac tacttggagg acaaaggcct tcctcacggc aacgtctcag cacggaaggt   2640
gctcctggct cgtgaggggg gtgatgggaa tccacctttc attaagctga gtgatcctgg   2700
tgtcagtccc actgtgctga gcctggaaat gctcaccgac agaataccct gggtggcccc   2760
cgaatgtctc caggaggctc agacactctg cttggaggct gacaagtggg gctttggagc   2820
caccacgtgg gaggtgttca gcggggggacc cgcccacatc acctcgctgg agcccgccaa   2880
aaagctgaag ttctatgagg accagggaca gctgcccgct ctcaaatgga cagaactggc   2940
gggacttatc acacagtgca tggcgtatga tcctggccgg cgcccctcct tccgagctat   3000
cctcagagac ctcaacggcc tcattacatc agattacgag ctcctctcag accccacacc   3060
tggcatcccg agtcctcgag atgagctgtg cggtggcgcc cagctctatg cctgccagga   3120
ccccgccata ttcgaggaga gacaccttaa gtacatctct ttgctgggca agggcaactt   3180
tggcagcgtg gagctgtgcc gctatgaccc cctgggggac aatacgggac ccctggtggc   3240
agtgaaacag ctacagcaca gcgggccaga ccagcagagg gacttccagc gggagattca   3300
gatccttaag gctctgcaca gcgacttcat cgtcaagtac cggggagtca gctatgggcc   3360
aggtcgccag agcctgcggt tggtgatgga gtacctgccc agcggctgcc tgcgagactt   3420
cctgcagcgc catcgcgcgc gcctgcacac cgaccgccta ctgctgttcg cttggcagat   3480
ctgcaagggc atggagtacc tgggtgcgcg ccgctgcgta caccgtgacc tggctgcgcg   3540
caacatcttg gtggagagcg aggctcatgt gaagatcgcg gacttcggcc tcgctaagct   3600
gctgccctg ggaaaggact actacgtggt ccgcgagcct ggccaaagcc catcttttg    3660
gtatgccccg gagtccctat ctgacaacat cttctcccgc caatctgacg tgtggagctt   3720
cggagtggtg ttgtacgagc tcttcaccta ctgcgacaag agctgcagcc atccgctga   3780
gttcctgcgc atgatggggc ctgagcgtga aggaccccg ctctgccgcc tcctggagct   3840
gctggcagag ggccgacgcc tcccaccacc tcccacctgc cccaccgagg ttcaggagct   3900
catgcagctg tgctgggcgc ccagcccgca cgaccggcca gccttcggca ccctgagccc   3960
ccagctggac gcgctgtggc gtggaagacc cggatagcag ccaggggcga gagtgagctt   4020
ggttcctatg atctggctgt gtgacctcag gcaggaaact gtccctttct gggccccatc   4080
accccttat cccctctggc cactccttcc catcattctt tcttcccaga atgggatat    4140
taaatatgtg aggccgcatc gtgactgact ga                                4172
```

<210> SEQ ID NO 3
<211> LENGTH: 3120
<212> TYPE: DNA
<213> ORGANISM: Artificial Sequence
<220> FEATURE:
<223> OTHER INFORMATION: cDNA sequence for Glutathione S-transferase-
truncated Janus Kinase fusion protein

<400> SEQUENCE: 3

```
agtattcatg tcccctatac taggttattg gaaaattaag ggccttgtgc aacccactcg    60
acttcttttg gaatatcttg aagaaaaata tgaagagcat ttgtatgagc gcgatgaagg   120
tgataaatgg cgaaacaaaa agtttgaatt gggtttggag tttcccaatc ttccttatta   180
tattgatggt gatgttaaat taacacagtc tatggccatc atacgttata tagctgacaa   240
gcacaacatg ttgggtggtt gtccaaaaga gcgtgcagag atttcaatgc ttgaaggagc   300
ggttttggat attagatacg gtgtttcgag aattgcatat agtaaagact ttgaaactct   360
caaagttgat tttcttagca agctacctga aatgctgaaa atgttcgaag atcgtttatg   420
tcataaaaca tatttaaatg gtgatcatgt aacccatcct gacttcatgt tgtatgacgc   480
tcttgatgtt gttttataca tggacccaat gtgcctggat gcgttcccaa aattagtttg   540
ttttaaaaaa cgtattgaag ctatcccaca aattgataag tacttgaaat ccagcaagta   600
tatagcatgg cctttgcagg gctgcaagc cacgtttggt ggtggcgacc atcctccaaa   660
atcggatctg gttccgcgtg atccccgaa ttccatggca cctccaagtg aggagacacc   720
tctgatccct cagcgctctt gcagcctctc atcctcagag caggagccc tgcatgtgct   780
ccttcctccc cggggaccctg ggcctcccca gcgattgtca ttctcttttg gggactactt   840
ggctgaggat ttatgtgtgc gagctgccaa ggcctgtggc atcctgcctg tttatcattc   900
gcttttcgct ctggccactg aggacttctc ttgctggttt cccccaagcc acatcttctg   960
catagaggac gtggacactc aagtcttggt ctacaggcta cgcttttatt tccctgactg  1020
gtttgggctg gagacatgtc accgctttgg gctgcgcaaa gatttgacca gtgccatcct  1080
tgacttacat gttttagaac atctctttgc tcagcaccgc agtgacctgg tgagtgggcg  1140
cctcccggtg ggccttagca tgaaggagca gggagagttc ctgagcctgg ccgtgctgga  1200
cttggcccag atggctcgtg agcaggccca gcgcccagga gagctgctga agacggtcag  1260
ttacaaagcc tgtctgccgc ccagcctgcg cgatgtgatc cagggccaga acttcgtgac  1320
acgcaggcgc atccgcagga ccgtggtctt ggcgctgcgc cgtgtggtcg cctgccaggc  1380
cgaccgctac gcgctcatgg ccaagtatat tctggacctg gagcggctac atccagcggc  1440
caccaccgag accttccgtg tggggctccc gggcgcccag gaggagccgg ggcttctgcg  1500
tgtggcgggg gacaacggca tctcctggag ctccggggac caggagcttt tccagacctt  1560
ctgtgacttt ccggaaatcg tggatgtcag catcaagcag gccccacgtg tgggtccggc  1620
aggggagcac cggctggtca ctgtcaccag gatggacggc cacatcctgg aagcggagtt  1680
tccggggctg cctgaggcgc tgtctttcgt ggccctcgtg gatgggtact ccgcctgat  1740
ctgcgactcc aggcattatt tctgcaagga ggtggcgccg ccacggctgc tggaggagga  1800
ggcggagctg tgccatggac ccatcacgtt agactttgcc atccacaagc tgaaggccgc  1860
tggctccctc ccaggcacct atattctccg ccgcagcccg caggactatg acagctttct  1920
tcttaccgcc tgcgtccaga ctcctcttgg ccccgactac aagggctgcc tcatccgcca  1980
ggacccccagc ggggctttct ccctggttgg cctcagccag ccccacagaa gcctgcggga  2040
gctgcttgca gcctgctgga attctgggct gcgagtagac ggtgctgccc tgaacctaac  2100
atcctgctgc gctcccagac ccaaggaaaa gtccaatttg atcgtggtgc aaggggctg  2160
cacccccgcg cctgccctg gctgctcccc gtcctgctgt gcgctgacac agctgagctt  2220
ccacacaatt ccaacggaca gcctggagtg gcacgagaac ctgggtcacg gttctttac   2280
```

| | |
|---|---|
| caagatcttc cgtggccgca ggcgggaggt cgtggatggt gagacacatg actcggaagt | 2340 |
| cctcctgaag gtcatggact ccagacatcg gaactgcatg gagtcttttc tggaagccgc | 2400 |
| aagcttgatg agccaagtat cctacccgca cctggtgtta ctgcacggcg tctgcatggc | 2460 |
| tggagacagc atcatggtgc aggaatttgt gtatctagga gcaattgaca tgtacctgcg | 2520 |
| caagcgtggc cacctggtgt cagccagctg gaaactgcag gtgaccaagc agctggcata | 2580 |
| tgcccttaac tacttggagg acaaaggcct tcctcacggc aacgtctcag cacggaaggt | 2640 |
| gctcctggct cgtgaggggg gtgatgggaa tccaccttc attaagctga gtgatcctgg | 2700 |
| tgtcagtccc actgtgctga gcctggaaat gctcaccgac agaataccct gggtggcccc | 2760 |
| cgaatgtctc caggaggctc agacactctg cttggaggct gacaagtggg gctttggagc | 2820 |
| caccacgtgg gaggtgttca gcgggggacc cgcccacatc acctcgctgg agcccgccaa | 2880 |
| aaagctgaag ttctatgagg accagggaca gctgccccgct ctcaaatgga cagaactggc | 2940 |
| gggacttatc acacagtgca tggcgtatga tcctggccgg cgcccctcct tccgagctat | 3000 |
| cctcagagac ctcaacggcc tcattacatc agattacgag ctcctctcag acccctagcc | 3060 |
| tggcatcccg agtcctcgag atgagctgtg cggtggcgcc cagctctatg cctgccagga | 3120 |

<210> SEQ ID NO 4
<211> LENGTH: 2160
<212> TYPE: DNA
<213> ORGANISM: Artificial Sequence
<220> FEATURE:
<223> OTHER INFORMATION: cDNA sequence for Glutathione S-transferase-
    truncated Janus Kinase fusion protein

<400> SEQUENCE: 4

| | |
|---|---|
| agtattcatg tcccctatac taggttattg gaaaattaag ggccttgtgc aacccactcg | 60 |
| acttcttttg gaatatcttg aagaaaaata tgaagagcat ttgtatgagc gcgatgaagg | 120 |
| tgataaatgg cgaaacaaaa agtttgaatt gggtttggag tttcccaatc ttccttatta | 180 |
| tattgatggt gatgttaaat taacacagtc tatggccatc atacgttata tagctgacaa | 240 |
| gcacaacatg ttgggtggtt gtccaaaaga gcgtgcagag atttcaatgc ttgaaggagc | 300 |
| ggttttggat attagatacg gtgtttcgag aattgcatat agtaaagact ttgaaactct | 360 |
| caaagttgat tttcttagca agctacctga aatgctgaaa atgttcgaag atcgtttatg | 420 |
| tcataaaaca tatttaaatg gtgatcatgt aacccatcct gacttcatgt tgtatgacgc | 480 |
| tcttgatgtt gttttataca tggacccaat gtgcctggat gcgttcccaa aattagtttg | 540 |
| tttttaaaaa cgtattgaag ctatcccaca aattgataag tacttgaaat ccagcaagta | 600 |
| tatagcatgg cctttgcagg ctggcaagc cacgtttggt ggtggcgacc atcctccaaa | 660 |
| atcggatctg gttccgcgtg gatccccgaa ttccatggca cctccaagtg aggagacacc | 720 |
| tctgatccct cagcgctctt gcagcctctc atcctcagag caggagccc tgcatgtgct | 780 |
| ccttcctccc cggggacctg ggcctcccca gcgattgtca ttctcttttg gggactactt | 840 |
| ggctgaggat ttatgtgtgc gagctgccaa ggcctgtggc atcctgcctg tttatcattc | 900 |
| gcttttcgct ctggccactg aggacttctc ttgctggttt cccccaagcc acatcttctg | 960 |
| catagaggac gtggacactc aagtcttggt ctacaggcta cgcttttatt tccctgactg | 1020 |
| gtttgggctg gagacatgtc accgctttgg gctgcgcaaa gatttgacca gtgccatcct | 1080 |
| tgacttacat gttttagaac atctctttgc tcagcaccgc agtgacctgg tgagtgggcg | 1140 |
| cctcccggtg ggccttagca tgaaggagca gggagagttc ctgagcctgg ccgtgctgga | 1200 |

| | |
|---|---|
| cttggcccag atggctcgtg agcaggccca gcgcccagga gagctgctga agacggtcag | 1260 |
| ttacaaagcc tgtctgccgc ccagcctgcg cgatgtgatc cagggccaga acttcgtgac | 1320 |
| acgcaggcgc atccgcagga ccgtggtctt ggcgctgcgc cgtgtggtcg cctgccaggc | 1380 |
| cgaccgctac gcgctcatgg ccaagtatat tctggacctg agcggctac atccagcggc | 1440 |
| caccaccgag accttccgtg tggggctccc gggcgcccag gaggagccgg ggcttctgcg | 1500 |
| tgtggcgggg gacaacggca tctcctggag ctccggggac caggagcttt tccagacctt | 1560 |
| ctgtgacttt ccggaaatcg tggatgtcag catcaagcag gccccacgtg tgggtccggc | 1620 |
| aggggagcac cggctggtca ctgtcaccag gatggacggc cacatcctgg aagcggagtt | 1680 |
| tccggggctg cctgaggcgc tgtctttcgt ggccctcgtg gatgggtact tccgcctgat | 1740 |
| ctgcgactcc aggcattatt ctgcaagga ggtggcgccg ccacggctgc tggaggagga | 1800 |
| ggcggagctg tgccatggac ccatcacgtt agactttgcc atccacaagc tgaaggccgc | 1860 |
| tggctccctc ccaggcacct atattctccg ccgcagcccg caggactatg acagcttcct | 1920 |
| tcttaccgcc tgcgtccaga ctcctcttgg ccccgactac aagggctgcc tcatccgcca | 1980 |
| ggaccccagc ggggctttct ccctggttgg cctcagccag ccccacagaa gcctgcggga | 2040 |
| gctgcttgca gcctgctgga attctgggct gcgagtagag ggtgctgccc tgaacctaac | 2100 |
| atcctgctgc gctcccagac ccaaggaaaa gtccaatttg atctaggtgc aaggggctg | 2160 |

<210> SEQ ID NO 5
<211> LENGTH: 1500
<212> TYPE: DNA
<213> ORGANISM: Artificial Sequence
<220> FEATURE:
<223> OTHER INFORMATION: cDNA sequence for Glutathione S-transferase-
   truncated Janus Kinase fusion protein

<400> SEQUENCE: 5

| | |
|---|---|
| agtattcatg tcccctatac taggttattg gaaaattaag ggccttgtgc aacccactcg | 60 |
| acttcttttg gaatatcttg aagaaaaata tgaagagcat ttgtatgagc gcgatgaagg | 120 |
| tgataaatgg cgaaacaaaa agtttgaatt gggtttggag tttcccaatc ttccttatta | 180 |
| tattgatggt gatgttaaat taacacagtc tatggccatc atacgttata tagctgacaa | 240 |
| gcacaacatg ttgggtggtt gtccaaaaga gcgtgcagag atttcaatgc ttgaaggagc | 300 |
| ggttttggat attagatacg tgtgttcgag aattgcatat agtaaagact tgaaactctc | 360 |
| caaagttgat tttcttagca agctacctga aatgctgaaa atgttcgaag atcgtttatg | 420 |
| tcataaaaca tatttaaatg gtgatcatgt aacccatcct gacttcatgt tgtatgacgc | 480 |
| tcttgatgtt gtttatacag tggacccaat gtgcctggat gcgttcccaa aattagtttg | 540 |
| ttttaaaaaa cgtattgaag ctatcccaca aattgataag tacttgaaat ccagcaagta | 600 |
| tatagcatgg cctttgcagg gctggcaagc cacgtttggt ggtggcgacc atcctccaaa | 660 |
| atcggatctg gttccgcgtg gatccccgaa ttccatggca cctccaagtg aggagacacc | 720 |
| tctgatccct cagcgctctt gcagcctctc atcctcagag gcaggagccc tgcatgtgct | 780 |
| ccttcctccc cggggacctg ggcctccca gcgattgtca ttctcttttg gggactactt | 840 |
| ggctgaggat ttatgtgtgc gagctgccaa ggcctgtggg atcctgcctg tttatcattc | 900 |
| gcttttcgct ctggccactg aggacttctc ttgctggttt ccccaagcc acatcttctg | 960 |
| catagaggac gtggacactc aagtcttggt ctacaggcta cgcttttatt tccctgactg | 1020 |
| gtttgggctg gagacatgtc accgctttgg gctgcgcaaa gatttgacca gtgccatcct | 1080 |

-continued

```
tgacttacat gttttagaac atctctttgc tcagcaccgc agtgacctgg tgagtgggcg    1140
cctcccggtg ggccttagca tgaaggagca gggagagttc ctgagcctgg ccgtgctgga    1200
cttggcccag atggctcgtg agcaggccca gcgcccagga gagctgctga agacggtcag    1260
ttacaaagcc tgtctgccgc ccagcctgcg cgatgtgatc cagggccaga acttcgtgac    1320
acgcaggcgc atccgcagga ccgtggtctt ggcgctgcgc cgtgtggtcg cctgccaggc    1380
cgaccgctac cgctcatgg ccaagtatat tctggacctg agcggctac atccagcggc     1440 caccaccgag accttccgtg tgtagctccc gggcgcccag gaggagccgg ggcttctgcg    1500
```

<210> SEQ ID NO 6
<211> LENGTH: 1099
<212> TYPE: PRT
<213> ORGANISM: Artificial Sequence
<220> FEATURE:
<223> OTHER INFORMATION: amino acid sequence of recombinant Janus Kinase 3 protein

<400> SEQUENCE: 6

```
Met Ala Pro Pro Ser Glu Glu Thr Pro Leu Ile Pro Gln Arg Ser
1               5                   10                  15

Cys Ser Leu Ser Ser Glu Ala Gly Ala Leu His Val Leu Leu
                20                  25                  30

Pro Pro Arg Gly Pro Gly Pro Pro Gln Arg Leu Ser Phe Ser Phe
                35                  40                  45

Gly Asp Tyr Leu Ala Glu Asp Leu Cys Val Arg Ala Ala Lys Ala
                50                  55                  60

Cys Gly Ile Leu Pro Val Tyr His Ser Leu Phe Ala Leu Ala Thr
                65                  70                  75

Glu Asp Phe Ser Cys Trp Phe Pro Pro Ser His Ile Phe Cys Ile
                80                  85                  90

Glu Asp Val Asp Thr Gln Val Leu Val Tyr Arg Leu Arg Phe Tyr
                95                  100                 105

Pro Asp Trp Phe Gly Leu Glu Thr Cys His Arg Phe Gly Leu Arg
                110                 115                 120

Lys Asp Leu Thr Ser Ala Ile Leu Asp Leu His Val Leu Glu His
                125                 130                 135

Leu Phe Ala Gln His Arg Ser Asp Leu Val Ser Gly Arg Leu Pro
                140                 145                 150

Val Gly Leu Ser Met Lys Glu Gln Gly Glu Phe Leu Ser Leu Ala
                155                 160                 165

Val Leu Asp Leu Ala Gln Met Ala Arg Glu Gln Ala Gln Arg Pro
                170                 175                 180

Gly Glu Leu Leu Lys Thr Val Ser Tyr Lys Ala Cys Leu Pro Pro
                185                 190                 195

Ser Leu Arg Asp Val Ile Gln Gly Gln Asn Phe Val Thr Arg Arg
                200                 205                 210

Arg Ile Arg Arg Thr Val Val Leu Ala Leu Arg Arg Val Val Ala
                215                 220                 225

Cys Gln Ala Asp Arg Tyr Ala Leu Met Ala Lys Tyr Ile Leu Asp
                230                 235                 240

Leu Glu Arg Leu His Pro Ala Ala Thr Thr Glu Thr Phe Arg Val
                245                 250                 255

Gly Leu Pro Gly Ala Gln Glu Glu Pro Gly Leu Leu Arg Val Ala
                260                 265                 270
```

```
Gly Asp Asn Gly Ile Ser Trp Ser Ser Gly Asp Gln Glu Leu Phe
            275                 280                 285
Gln Thr Phe Cys Asp Phe Pro Glu Ile Val Asp Val Ser Ile Lys
            290                 295                 300
Gln Ala Pro Arg Val Gly Pro Ala Gly Glu His Arg Leu Val Thr
            305                 310                 315
Val Thr Arg Met Asp Gly His Ile Leu Glu Ala Glu Phe Pro Gly
            320                 325                 330
Leu Pro Glu Ala Leu Ser Phe Val Ala Leu Val Asp Gly Tyr Phe
            335                 340                 345
Arg Leu Ile Cys Asp Ser Arg His Tyr Phe Cys Lys Glu Val Ala
            350                 355                 360
Pro Pro Arg Leu Leu Glu Glu Glu Ala Glu Leu Cys His Gly Pro
            365                 370                 375
Ile Thr Leu Asp Phe Ala Ile His Lys Leu Lys Ala Ala Gly Ser
            380                 385                 390
Leu Pro Gly Thr Tyr Ile Leu Arg Arg Ser Pro Gln Asp Tyr Asp
            395                 400                 405
Ser Phe Leu Leu Thr Ala Cys Val Gln Thr Pro Leu Gly Pro Asp
            410                 415                 420
Tyr Lys Gly Cys Leu Ile Arg Gln Asp Pro Ser Gly Ala Phe Ser
            425                 430                 435
Leu Val Gly Leu Ser Gln Pro His Arg Ser Leu Arg Glu Leu Leu
            440                 445                 450
Ala Ala Cys Trp Asn Ser Gly Leu Arg Val Asp Gly Ala Ala Leu
            455                 460                 465
Asn Leu Thr Ser Cys Cys Ala Pro Arg Pro Lys Glu Lys Ser Asn
            470                 475                 480
Leu Ile Val Val Arg Arg Gly Cys Thr Pro Ala Pro Ala Pro Gly
            485                 490                 495
Cys Ser Pro Ser Cys Cys Ala Leu Thr Gln Leu Ser Phe His Thr
            500                 505                 510
Ile Pro Thr Asp Ser Leu Glu Trp His Glu Asn Leu Gly His Gly
            515                 520                 525
Ser Phe Thr Lys Ile Phe Arg Gly Arg Arg Glu Val Val Asp
            530                 535                 540
Gly Glu Thr His Asp Ser Glu Val Leu Leu Lys Val Met Asp Ser
            545                 550                 555
Arg His Arg Asn Cys Met Glu Ser Phe Leu Glu Ala Ala Ser Leu
            560                 565                 570
Met Ser Gln Val Ser Tyr Pro His Leu Val Leu Leu His Gly Val
            575                 580                 585
Cys Met Ala Gly Asp Ser Ile Met Val Gln Glu Phe Val Tyr Leu
            590                 595                 600
Gly Ala Ile Asp Met Tyr Leu Arg Lys Arg Gly His Leu Val Ser
            605                 610                 615
Ala Ser Trp Lys Leu Gln Val Thr Lys Gln Leu Ala Tyr Ala Leu
            620                 625                 630
Asn Tyr Leu Glu Asp Lys Gly Leu Pro His Gly Asn Val Ser Ala
            635                 640                 645
Arg Lys Val Leu Leu Ala Arg Glu Gly Gly Asp Gly Asn Pro Pro
            650                 655                 660
Phe Ile Lys Leu Ser Asp Pro Gly Val Ser Pro Thr Val Leu Ser
```

-continued

```
                665                 670                 675
Leu Glu Met Leu Thr Asp Arg Ile Pro Trp Val Ala Pro Glu Cys
            680                 685                 690

Leu Gln Glu Ala Gln Thr Leu Cys Leu Glu Ala Asp Lys Trp Gly
            695                 700                 705

Phe Gly Ala Thr Thr Trp Glu Val Phe Ser Gly Gly Pro Ala His
            710                 715                 720

Ile Thr Ser Leu Glu Pro Ala Lys Lys Leu Lys Phe Tyr Glu Asp
            725                 730                 735

Gln Gly Gln Leu Pro Ala Leu Lys Trp Thr Glu Leu Ala Gly Leu
            740                 745                 750

Ile Thr Gln Cys Met Ala Tyr Asp Pro Gly Arg Arg Pro Ser Phe
            755                 760                 765

Arg Ala Ile Leu Arg Asp Leu Asn Gly Leu Ile Thr Ser Asp Tyr
            770                 775                 780

Glu Leu Leu Ser Asp Pro Thr Pro Gly Ile Pro Ser Pro Arg Asp
            785                 790                 795

Glu Leu Cys Gly Gly Ala Gln Leu Tyr Ala Cys Gln Asp Pro Ala
            800                 805                 810

Ile Phe Glu Glu Arg His Leu Lys Tyr Ile Ser Leu Leu Gly Lys
            815                 820                 825

Gly Asn Phe Gly Ser Val Glu Leu Cys Arg Tyr Asp Pro Leu Gly
            830                 835                 840

Asp Asn Thr Gly Pro Leu Val Ala Val Lys Gln Leu Gln His Ser
            845                 850                 855

Gly Pro Asp Gln Gln Arg Asp Phe Gln Arg Glu Ile Gln Ile Leu
            860                 865                 870

Lys Ala Leu His Ser Asp Phe Ile Val Lys Tyr Arg Gly Val Ser
            875                 880                 885

Tyr Gly Pro Gly Arg Gln Ser Leu Arg Leu Val Met Glu Tyr Leu
            890                 895                 900

Pro Ser Gly Cys Leu Arg Asp Phe Leu Gln Arg His Arg Ala Arg
            905                 910                 915

Leu His Thr Asp Arg Leu Leu Leu Phe Ala Trp Gln Ile Cys Lys
            920                 925                 930

Gly Met Glu Tyr Leu Gly Ala Arg Arg Cys Val His Arg Asp Leu
            935                 940                 945

Ala Ala Arg Asn Ile Leu Val Glu Ser Glu Ala His Val Lys Ile
            950                 955                 960

Ala Asp Phe Gly Leu Ala Lys Leu Leu Pro Leu Gly Lys Asp Tyr
            965                 970                 975

Tyr Val Val Arg Glu Pro Gly Gln Ser Pro Ile Phe Trp Tyr Ala
            980                 985                 990

Pro Glu Ser Leu Ser Asp Asn Ile Phe Ser Arg Gln Ser Asp Val
            995                1000                1005

Trp Ser Phe Gly Val Val Leu Tyr Glu Leu Phe Thr Tyr Cys Asp
           1010                1015                1020

Lys Ser Cys Ser Pro Ser Ala Glu Phe Leu Arg Met Met Gly Pro
           1025                1030                1035

Glu Arg Glu Gly Pro Pro Leu Cys Arg Leu Leu Glu Leu Leu Ala
           1040                1045                1050

Glu Gly Arg Arg Leu Pro Pro Pro Pro Thr Cys Pro Thr Glu Val
           1055                1060                1065
```

-continued

```
Gln Glu Leu Met Gln Leu Cys Trp Ala Pro Ser Pro His Asp Arg
            1070                1075                1080

Pro Ala Phe Gly Thr Leu Ser Pro Gln Leu Asp Ala Leu Trp Arg
            1085                1090                1095

Gly Arg Pro Gly

<210> SEQ ID NO 7
<211> LENGTH: 1388
<212> TYPE: PRT
<213> ORGANISM: Artificial Sequence
<220> FEATURE:
<223> OTHER INFORMATION: amino acid sequence of Glutathione
      S-transferase-Janus Kinase 3 fusion protein

<400> SEQUENCE: 7

Val Phe Met Ser Pro Ile Leu Gly Tyr Trp Lys Ile Lys Gly Leu
1               5                   10                  15

Val Gln Pro Thr Arg Leu Leu Leu Glu Tyr Leu Glu Glu Lys Tyr
                20                  25                  30

Glu Glu His Leu Tyr Glu Arg Asp Glu Gly Asp Lys Trp Arg Asn
                35                  40                  45

Lys Lys Phe Glu Leu Gly Leu Glu Phe Pro Asn Leu Pro Tyr Tyr
                50                  55                  60

Ile Asp Gly Asp Val Lys Leu Thr Gln Ser Met Ala Ile Ile Arg
                65                  70                  75

Tyr Ile Ala Asp Lys His Asn Met Leu Gly Gly Cys Pro Lys Glu
                80                  85                  90

Arg Ala Glu Ile Ser Met Leu Glu Gly Ala Val Leu Asp Ile Arg
                95                  100                 105

Tyr Gly Val Ser Arg Ile Ala Tyr Ser Lys Asp Phe Glu Thr Leu
                110                 115                 120

Lys Val Asp Phe Leu Ser Lys Leu Pro Glu Met Leu Lys Met Phe
                125                 130                 135

Glu Asp Arg Leu Cys His Lys Thr Tyr Leu Asn Gly Asp His Val
                140                 145                 150

Thr His Pro Asp Phe Met Leu Tyr Asp Ala Leu Asp Val Val Leu
                155                 160                 165

Tyr Met Asp Pro Met Cys Leu Asp Ala Phe Pro Lys Leu Val Cys
                170                 175                 180

Phe Lys Lys Arg Ile Glu Ala Ile Pro Gln Ile Asp Lys Tyr Leu
                185                 190                 195

Lys Ser Ser Lys Tyr Ile Ala Trp Pro Leu Gln Gly Trp Gln Ala
                200                 205                 210

Thr Phe Gly Gly Gly Asp His Pro Pro Lys Ser Asp Leu Val Pro
                215                 220                 225

Arg Gly Ser Pro Asn Ser Met Ala Pro Ser Glu Glu Thr Pro
                230                 235                 240

Leu Ile Pro Gln Arg Ser Cys Ser Leu Ser Ser Ser Glu Ala Gly
                245                 250                 255

Ala Leu His Val Leu Leu Pro Pro Arg Gly Pro Gly Pro Pro Gln
                260                 265                 270

Arg Leu Ser Phe Ser Phe Gly Asp Tyr Leu Ala Glu Asp Leu Cys
                275                 280                 285

Val Arg Ala Ala Lys Ala Cys Gly Ile Leu Pro Val Tyr His Ser
                290                 295                 300
```

```
Leu Phe Ala Leu Ala Thr Glu Asp Phe Ser Cys Trp Phe Pro Pro
                305                 310                 315
Ser His Ile Phe Cys Ile Glu Asp Val Asp Thr Gln Val Leu Val
                320                 325                 330
Tyr Arg Leu Arg Phe Tyr Phe Pro Asp Trp Phe Gly Leu Glu Thr
                335                 340                 345
Cys His Arg Phe Gly Leu Arg Lys Asp Leu Thr Ser Ala Ile Leu
                350                 355                 360
Asp Leu His Val Leu Glu His Leu Phe Ala Gln His Arg Ser Asp
                365                 370                 375
Leu Val Ser Gly Arg Leu Pro Val Gly Leu Ser Met Lys Glu Gln
                380                 385                 390
Gly Glu Phe Leu Ser Leu Ala Val Leu Asp Leu Ala Gln Met Ala
                395                 400                 405
Arg Glu Gln Ala Gln Arg Pro Gly Glu Leu Leu Lys Thr Val Ser
                410                 415                 420
Tyr Lys Ala Cys Leu Pro Pro Ser Leu Arg Asp Val Ile Gln Gly
                425                 430                 435
Gln Asn Phe Val Thr Arg Arg Ile Arg Arg Thr Val Leu
                440                 445                 450
Ala Leu Arg Arg Val Val Ala Cys Gln Ala Asp Arg Tyr Ala Leu
                455                 460                 465
Met Ala Lys Tyr Ile Leu Asp Leu Glu Arg Leu His Pro Ala Ala
                470                 475                 480
Thr Thr Glu Thr Phe Arg Val Gly Leu Pro Gly Ala Gln Glu Glu
                485                 490                 495
Pro Gly Leu Leu Arg Val Ala Gly Asp Asn Gly Ile Ser Trp Ser
                500                 505                 510
Ser Gly Asp Gln Glu Leu Phe Gln Thr Phe Cys Asp Phe Pro Glu
                515                 520                 525
Ile Val Asp Val Ser Ile Lys Gln Ala Pro Arg Val Gly Pro Ala
                530                 535                 540
Gly Glu His Arg Leu Val Thr Val Thr Arg Met Asp Gly His Ile
                545                 550                 555
Leu Glu Ala Glu Phe Pro Gly Leu Pro Glu Ala Leu Ser Phe Val
                560                 565                 570
Ala Leu Val Asp Gly Tyr Phe Arg Leu Ile Cys Asp Ser Arg His
                575                 580                 585
Tyr Phe Cys Lys Glu Val Ala Pro Pro Arg Leu Leu Glu Glu Glu
                590                 595                 600
Ala Glu Leu Cys His Gly Pro Ile Thr Leu Asp Phe Ala Ile His
                605                 610                 615
Lys Leu Lys Ala Ala Gly Ser Leu Pro Gly Thr Tyr Ile Leu Arg
                620                 625                 630
Arg Ser Pro Gln Asp Tyr Asp Ser Phe Leu Leu Thr Ala Cys Val
                635                 640                 645
Gln Thr Pro Leu Gly Pro Asp Tyr Lys Gly Cys Leu Ile Arg Gln
                650                 655                 660
Asp Pro Ser Gly Ala Phe Ser Leu Val Gly Leu Ser Gln Pro His
                665                 670                 675
Arg Ser Leu Arg Glu Leu Leu Ala Ala Cys Trp Asn Ser Gly Leu
                680                 685                 690
```

```
Arg Val Asp Gly Ala Ala Leu Asn Leu Thr Ser Cys Cys Ala Pro
            695                 700                 705

Arg Pro Lys Glu Lys Ser Asn Leu Ile Val Val Arg Arg Gly Cys
            710                 715                 720

Thr Pro Ala Pro Ala Pro Gly Cys Ser Pro Ser Cys Cys Ala Leu
            725                 730                 735

Thr Gln Leu Ser Phe His Thr Ile Pro Thr Asp Ser Leu Glu Trp
            740                 745                 750

His Glu Asn Leu Gly His Gly Ser Phe Thr Lys Ile Phe Arg Gly
            755                 760                 765

Arg Arg Arg Glu Val Val Asp Gly Glu Thr His Asp Ser Glu Val
            770                 775                 780

Leu Leu Lys Val Met Asp Ser Arg His Arg Asn Cys Met Glu Ser
            785                 790                 795

Phe Leu Glu Ala Ala Ser Leu Met Ser Gln Val Ser Tyr Pro His
            800                 805                 810

Leu Val Leu Leu His Gly Val Cys Met Ala Gly Asp Ser Ile Met
            815                 820                 825

Val Gln Glu Phe Val Tyr Leu Gly Ala Ile Asp Met Tyr Leu Arg
            830                 835                 840

Lys Arg Gly His Leu Val Ser Ala Ser Trp Lys Leu Gln Val Thr
            845                 850                 855

Lys Gln Leu Ala Tyr Ala Leu Asn Tyr Leu Glu Asp Lys Gly Leu
            860                 865                 870

Pro His Gly Asn Val Ser Ala Arg Lys Val Leu Leu Ala Arg Glu
            875                 880                 885

Gly Gly Asp Gly Asn Pro Pro Phe Ile Lys Leu Ser Asp Pro Gly
            890                 895                 900

Val Ser Pro Thr Val Leu Ser Leu Glu Met Leu Thr Asp Arg Ile
            905                 910                 915

Pro Trp Val Ala Pro Glu Cys Leu Gln Glu Ala Gln Thr Leu Cys
            920                 925                 930

Leu Glu Ala Asp Lys Trp Gly Phe Gly Ala Thr Thr Trp Glu Val
            935                 940                 945

Phe Ser Gly Gly Pro Ala His Ile Thr Ser Leu Glu Pro Ala Lys
            950                 955                 960

Lys Leu Lys Phe Tyr Glu Asp Gln Gly Gln Leu Pro Ala Leu Lys
            965                 970                 975

Trp Thr Glu Leu Ala Gly Leu Ile Thr Gln Cys Met Ala Tyr Asp
            980                 985                 990

Pro Gly Arg Arg Pro Ser Phe Arg Ala Ile Leu Arg Asp Leu Asn
            995                 1000                1005

Gly Leu Ile Thr Ser Asp Tyr Glu Leu Leu Ser Asp Pro Thr Pro
            1010                1015                1020

Gly Ile Pro Ser Pro Arg Asp Glu Leu Cys Gly Gly Ala Gln Leu
            1025                1030                1035

Tyr Ala Cys Gln Asp Pro Ala Ile Phe Glu Glu Arg His Leu Lys
            1040                1045                1050

Tyr Ile Ser Leu Leu Gly Lys Gly Asn Phe Gly Ser Val Glu Leu
            1055                1060                1065

Cys Arg Tyr Asp Pro Leu Gly Asp Asn Thr Gly Pro Leu Val Ala
            1070                1075                1080

Val Lys Gln Leu Gln His Ser Gly Pro Asp Gln Gln Arg Asp Phe
```

```
          1085                1090                1095

Gln Arg Glu Ile Gln Ile Leu Lys Ala Leu His Ser Asp Phe Ile
         1100                1105                1110

Val Lys Tyr Arg Gly Val Ser Tyr Gly Pro Gly Arg Gln Ser Leu
         1115                1120                1125

Arg Leu Val Met Glu Tyr Leu Pro Ser Gly Cys Leu Arg Asp Phe
         1130                1135                1140

Leu Gln Arg His Arg Ala Arg Leu His Thr Asp Arg Leu Leu Leu
         1145                1150                1155

Phe Ala Trp Gln Ile Cys Lys Gly Met Glu Tyr Leu Gly Ala Arg
         1160                1165                1170

Arg Cys Val His Arg Asp Leu Ala Ala Arg Asn Ile Leu Val Glu
         1175                1180                1185

Ser Glu Ala His Val Lys Ile Ala Asp Phe Gly Leu Ala Lys Leu
         1190                1195                1200

Leu Pro Leu Gly Lys Asp Tyr Tyr Val Val Arg Glu Pro Gly Gln
         1205                1210                1215

Ser Pro Ile Phe Trp Tyr Ala Pro Glu Ser Leu Ser Asp Asn Ile
         1220                1225                1230

Phe Ser Arg Gln Ser Asp Val Trp Ser Phe Gly Val Val Leu Tyr
         1235                1240                1245

Glu Leu Phe Thr Tyr Cys Asp Lys Ser Cys Ser Pro Ser Ala Glu
         1250                1255                1260

Phe Leu Arg Met Met Gly Pro Glu Arg Glu Gly Pro Pro Leu Cys
         1265                1270                1275

Arg Leu Leu Glu Leu Leu Ala Glu Gly Arg Arg Leu Pro Pro Pro
         1280                1285                1290

Pro Thr Cys Pro Thr Glu Val Gln Glu Leu Met Gln Leu Cys Trp
         1295                1300                1305

Ala Pro Ser Pro His Asp Arg Pro Ala Phe Gly Thr Leu Ser Pro
         1310                1315                1320

Gln Leu Asp Ala Leu Trp Arg Gly Arg Pro Gly Gln Pro Gly Ala
         1325                1330                1335

Arg Val Ser Leu Val Pro Met Ile Trp Leu Cys Asp Leu Arg Gln
         1340                1345                1350

Glu Thr Val Pro Phe Trp Ala Pro Ser Pro Pro Tyr Pro Leu Trp
         1355                1360                1365

Pro Leu Leu Pro Ile Ile Leu Ser Ser Gln Asn Gly Asp Ile Lys
         1370                1375                1380

Tyr Val Arg Pro His Arg Asp Leu
         1385

<210> SEQ ID NO 8
<211> LENGTH: 1030
<212> TYPE: PRT
<213> ORGANISM: Artificial Sequence
<220> FEATURE:
<223> OTHER INFORMATION: amino acid sequence of Glutathione
      S-Transferase-truncated Janus Kinase 3 fusion protein

<400> SEQUENCE: 8

Val Phe Met Ser Pro Ile Leu Gly Tyr Trp Lys Ile Lys Gly Leu
1               5                   10                  15

Val Gln Pro Thr Arg Leu Leu Leu Glu Tyr Leu Glu Glu Lys Tyr
                20                  25                  30
```

-continued

Glu Glu His Leu Tyr Glu Arg Asp Glu Gly Asp Lys Trp Arg Asn
             35                  40                  45

Lys Lys Phe Glu Leu Gly Leu Glu Phe Pro Asn Leu Pro Tyr Tyr
         50                  55                  60

Ile Asp Gly Asp Val Lys Leu Thr Gln Ser Met Ala Ile Ile Arg
             65                  70                  75

Tyr Ile Ala Asp Lys His Asn Met Leu Gly Gly Cys Pro Lys Glu
             80                  85                  90

Arg Ala Glu Ile Ser Met Leu Glu Gly Ala Val Leu Asp Ile Arg
             95                 100                 105

Tyr Gly Val Ser Arg Ile Ala Tyr Ser Lys Asp Phe Glu Thr Leu
            110                 115                 120

Lys Val Asp Phe Leu Ser Lys Leu Pro Glu Met Leu Lys Met Phe
            125                 130                 135

Glu Asp Arg Leu Cys His Lys Thr Tyr Leu Asn Gly Asp His Val
            140                 145                 150

Thr His Pro Asp Phe Met Leu Tyr Asp Ala Leu Asp Val Val Leu
            155                 160                 165

Tyr Met Asp Pro Met Cys Leu Asp Ala Phe Pro Lys Leu Val Cys
            170                 175                 180

Phe Lys Lys Arg Ile Glu Ala Ile Pro Gln Ile Asp Lys Tyr Leu
            185                 190                 195

Lys Ser Ser Lys Tyr Ile Ala Trp Pro Leu Gln Gly Trp Gln Ala
            200                 205                 210

Thr Phe Gly Gly Gly Asp His Pro Pro Lys Ser Asp Leu Val Pro
            215                 220                 225

Arg Gly Ser Pro Asn Ser Met Ala Pro Ser Glu Glu Thr Pro
            230                 235                 240

Leu Ile Pro Gln Arg Ser Cys Ser Leu Ser Ser Ser Glu Ala Gly
            245                 250                 255

Ala Leu His Val Leu Leu Pro Pro Arg Gly Pro Gly Pro Pro Gln
            260                 265                 270

Arg Leu Ser Phe Ser Phe Gly Asp Tyr Leu Ala Glu Asp Leu Cys
            275                 280                 285

Val Arg Ala Ala Lys Ala Cys Gly Ile Leu Pro Val Tyr His Ser
            290                 295                 300

Leu Phe Ala Leu Ala Thr Glu Asp Phe Ser Cys Trp Phe Pro Pro
            305                 310                 315

Ser His Ile Phe Cys Ile Glu Asp Val Asp Thr Gln Val Leu Val
            320                 325                 330

Tyr Arg Leu Arg Phe Tyr Phe Pro Asp Trp Phe Gly Leu Glu Thr
            335                 340                 345

Cys His Arg Phe Gly Leu Arg Lys Asp Leu Thr Ser Ala Ile Leu
            350                 355                 360

Asp Leu His Val Leu Glu His Leu Phe Ala Gln His Arg Ser Asp
            365                 370                 375

Leu Val Ser Gly Arg Leu Pro Val Gly Leu Ser Met Lys Glu Gln
            380                 385                 390

Gly Glu Phe Leu Ser Leu Ala Val Leu Asp Leu Ala Gln Met Ala
            395                 400                 405

Arg Glu Gln Ala Gln Arg Pro Gly Glu Leu Leu Lys Thr Val Ser
            410                 415                 420

Tyr Lys Ala Cys Leu Pro Pro Ser Leu Arg Asp Val Ile Gln Gly

-continued

Gln Asn Phe Val Thr Arg Arg Ile Arg Arg Thr Val Val Leu
                425                 430                 435
Ala Leu Arg Arg Val Val Ala Cys Gln Ala Asp Arg Tyr Ala Leu
            440                 445                 450
Met Ala Lys Tyr Ile Leu Asp Leu Glu Arg Leu His Pro Ala Ala
        455                 460                 465
Thr Thr Glu Thr Phe Arg Val Gly Leu Pro Gly Ala Gln Glu Glu
    470                 475                 480
Pro Gly Leu Leu Arg Val Ala Gly Asp Asn Gly Ile Ser Trp Ser
485                 490                 495
Ser Gly Asp Gln Glu Leu Phe Gln Thr Phe Cys Asp Phe Pro Glu
            500                 505                 510
Ile Val Asp Val Ser Ile Lys Gln Ala Pro Arg Val Gly Pro Ala
        515                 520                 525
Gly Glu His Arg Leu Val Thr Val Thr Arg Met Asp Gly His Ile
    530                 535                 540
Leu Glu Ala Glu Phe Pro Gly Leu Pro Glu Ala Leu Ser Phe Val
545                 550                 555
Ala Leu Val Asp Gly Tyr Phe Arg Leu Ile Cys Asp Ser Arg His
            560                 565                 570
Tyr Phe Cys Lys Glu Val Ala Pro Pro Arg Leu Leu Glu Glu
        575                 580                 585
Ala Glu Leu Cys His Gly Pro Ile Thr Leu Asp Phe Ala Ile His
    590                 595                 600
Lys Leu Lys Ala Ala Gly Ser Leu Pro Gly Thr Tyr Ile Leu Arg
605                 610                 615
Arg Ser Pro Gln Asp Tyr Asp Ser Phe Leu Leu Thr Ala Cys Val
            620                 625                 630
Gln Thr Pro Leu Gly Pro Asp Tyr Lys Gly Cys Leu Ile Arg Gln
        635                 640                 645
Asp Pro Ser Gly Ala Phe Ser Leu Val Gly Leu Ser Gln Pro His
    650                 655                 660
Arg Ser Leu Arg Glu Leu Leu Ala Ala Cys Trp Asn Ser Gly Leu
665                 670                 675
Arg Val Asp Gly Ala Ala Leu Asn Leu Thr Ser Cys Cys Ala Pro
            680                 685                 690
Arg Pro Lys Glu Lys Ser Asn Leu Ile Val Val Arg Arg Gly Cys
        695                 700                 705
Thr Pro Ala Pro Ala Pro Gly Cys Ser Pro Ser Cys Cys Ala Leu
    710                 715                 720
Thr Gln Leu Ser Phe His Thr Ile Pro Thr Asp Ser Leu Glu Trp
725                 730                 735
His Glu Asn Leu Gly His Gly Ser Phe Thr Lys Ile Phe Arg Gly
            740                 745                 750
Arg Arg Arg Glu Val Val Asp Gly Glu Thr His Asp Ser Glu Val
        755                 760                 765
Leu Leu Lys Val Met Asp Ser Arg His Arg Asn Cys Met Glu Ser
    770                 775                 780
Phe Leu Glu Ala Ala Ser Leu Met Ser Gln Val Ser Tyr Pro His
785                 790                 795
Leu Val Leu Leu His Gly Val Cys Met Ala Gly Asp Ser Ile Met
            800                 805                 810
                815                 820                 825

```
Val Gln Glu Phe Val Tyr Leu Gly Ala Ile Asp Met Tyr Leu Arg
            830                 835                 840

Lys Arg Gly His Leu Val Ser Ala Ser Trp Lys Leu Gln Val Thr
            845                 850                 855

Lys Gln Leu Ala Tyr Ala Leu Asn Tyr Leu Glu Asp Lys Gly Leu
            860                 865                 870

Pro His Gly Asn Val Ser Ala Arg Lys Val Leu Leu Ala Arg Glu
            875                 880                 885

Gly Gly Asp Gly Asn Pro Pro Phe Ile Lys Leu Ser Asp Pro Gly
            890                 895                 900

Val Ser Pro Thr Val Leu Ser Leu Glu Met Leu Thr Asp Arg Ile
            905                 910                 915

Pro Trp Val Ala Pro Glu Cys Leu Gln Glu Ala Gln Thr Leu Cys
            920                 925                 930

Leu Glu Ala Asp Lys Trp Gly Phe Gly Ala Thr Thr Trp Glu Val
            935                 940                 945

Phe Ser Gly Gly Pro Ala His Ile Thr Ser Leu Glu Pro Ala Lys
            950                 955                 960

Lys Leu Lys Phe Tyr Glu Asp Gln Gly Gln Leu Pro Ala Leu Lys
            965                 970                 975

Trp Thr Glu Leu Ala Gly Leu Ile Thr Gln Cys Met Ala Tyr Asp
            980                 985                 990

Pro Gly Arg Arg Pro Ser Phe Arg Ala Ile Leu Arg Asp Leu Asn
            995                 1000                1005

Gly Leu Ile Thr Ser Asp Tyr Glu Leu Leu Ser Asp Pro Pro Gly
            1010                1015                1020

Ile Pro Ser Pro Arg Asp Glu Leu Cys Gly
            1025                1030

<210> SEQ ID NO 9
<211> LENGTH: 726
<212> TYPE: PRT
<213> ORGANISM: Artificial Sequence
<220> FEATURE:
<223> OTHER INFORMATION: amino acid sequence of Glutathione
      S-transferase-truncated Janus Kinase 3 fusion protein

<400> SEQUENCE: 9

Val Phe Met Ser Pro Ile Leu Gly Tyr Trp Lys Ile Lys Gly Leu
1               5                   10                  15

Val Gln Pro Thr Arg Leu Leu Leu Glu Tyr Leu Glu Glu Lys Tyr
                20                  25                  30

Glu Glu His Leu Tyr Glu Arg Asp Glu Gly Asp Lys Trp Arg Asn
            35                  40                  45

Lys Lys Phe Glu Leu Gly Leu Glu Phe Pro Asn Leu Pro Tyr Tyr
        50                  55                  60

Ile Asp Gly Asp Val Lys Leu Thr Gln Ser Met Ala Ile Ile Arg
    65                  70                  75

Tyr Ile Ala Asp Lys His Asn Met Leu Gly Gly Cys Pro Lys Glu
            80                  85                  90

Arg Ala Glu Ile Ser Met Leu Glu Gly Ala Val Leu Asp Ile Arg
            95                  100                 105

Tyr Gly Val Ser Arg Ile Ala Tyr Ser Lys Asp Phe Glu Thr Leu
            110                 115                 120

Lys Val Asp Phe Leu Ser Lys Leu Pro Glu Met Leu Lys Met Phe
```

```
                    125                 130                 135
Glu Asp Arg Leu Cys His Lys Thr Tyr Leu Asn Gly Asp His Val
                140                 145                 150
Thr His Pro Asp Phe Met Leu Tyr Asp Ala Leu Asp Val Val Leu
                155                 160                 165
Tyr Met Asp Pro Met Cys Leu Asp Ala Phe Pro Lys Leu Val Cys
                170                 175                 180
Phe Lys Lys Arg Ile Glu Ala Ile Pro Gln Ile Asp Lys Tyr Leu
                185                 190                 195
Lys Ser Ser Lys Tyr Ile Ala Trp Pro Leu Gln Gly Trp Gln Ala
                200                 205                 210
Thr Phe Gly Gly Gly Asp His Pro Pro Lys Ser Asp Leu Val Pro
                215                 220                 225
Arg Gly Ser Pro Asn Ser Met Ala Pro Ser Glu Glu Thr Pro
                230                 235                 240
Leu Ile Pro Gln Arg Ser Cys Ser Leu Ser Ser Ser Glu Ala Gly
                245                 250                 255
Ala Leu His Val Leu Leu Pro Pro Arg Gly Pro Gly Pro Pro Gln
                260                 265                 270
Arg Leu Ser Phe Ser Phe Gly Asp Tyr Leu Ala Glu Asp Leu Cys
                275                 280                 285
Val Arg Ala Ala Lys Ala Cys Gly Ile Leu Pro Val Tyr His Ser
                290                 295                 300
Leu Phe Ala Leu Ala Thr Glu Asp Phe Ser Cys Trp Phe Pro Pro
                305                 310                 315
Ser His Ile Phe Cys Ile Glu Asp Val Asp Thr Gln Val Leu Val
                320                 325                 330
Tyr Arg Leu Arg Phe Tyr Phe Pro Asp Trp Phe Gly Leu Glu Thr
                335                 340                 345
Cys His Arg Phe Gly Leu Arg Lys Asp Leu Thr Ser Ala Ile Leu
                350                 355                 360
Asp Leu His Val Leu Glu His Leu Phe Ala Gln His Arg Ser Asp
                365                 370                 375
Leu Val Ser Gly Arg Leu Pro Val Gly Leu Ser Met Lys Glu Gln
                380                 385                 390
Gly Glu Phe Leu Ser Leu Ala Val Leu Asp Leu Ala Gln Met Ala
                395                 400                 405
Arg Glu Gln Ala Gln Arg Pro Gly Glu Leu Leu Lys Thr Val Ser
                410                 415                 420
Tyr Lys Ala Cys Leu Pro Pro Ser Leu Arg Asp Val Ile Gln Gly
                425                 430                 435
Gln Asn Phe Val Thr Arg Arg Ile Arg Arg Thr Val Val Leu
                440                 445                 450
Ala Leu Arg Arg Val Val Ala Cys Gln Ala Asp Arg Tyr Ala Leu
                455                 460                 465
Met Ala Lys Tyr Ile Leu Asp Leu Glu Arg Leu His Pro Ala Ala
                470                 475                 480
Thr Thr Glu Thr Phe Arg Val Gly Leu Pro Gly Ala Gln Glu Glu
                485                 490                 495
Pro Gly Leu Leu Arg Val Ala Gly Asp Asn Gly Ile Ser Trp Ser
                500                 505                 510
Ser Gly Asp Gln Glu Leu Phe Gln Thr Phe Cys Asp Phe Pro Glu
                515                 520                 525
```

```
Ile Val Asp Val Ser Ile Lys Gln Ala Pro Arg Val Gly Pro Ala
            530                 535                 540

Gly Glu His Arg Leu Val Thr Val Thr Arg Met Asp Gly His Ile
            545                 550                 555

Leu Glu Ala Glu Phe Pro Gly Leu Pro Glu Ala Leu Ser Phe Val
            560                 565                 570

Ala Leu Val Asp Gly Tyr Phe Arg Leu Ile Cys Asp Ser Arg His
            575                 580                 585

Tyr Phe Cys Lys Glu Val Ala Pro Pro Arg Leu Leu Glu Glu Glu
            590                 595                 600

Ala Glu Leu Cys His Gly Pro Ile Thr Leu Asp Phe Ala Ile His
            605                 610                 615

Lys Leu Lys Ala Ala Gly Ser Leu Pro Gly Thr Tyr Ile Leu Arg
            620                 625                 630

Arg Ser Pro Gln Asp Tyr Asp Ser Phe Leu Leu Thr Ala Cys Val
            635                 640                 645

Gln Thr Pro Leu Gly Pro Asp Tyr Lys Gly Cys Leu Ile Arg Gln
            650                 655                 660

Asp Pro Ser Gly Ala Phe Ser Leu Val Gly Leu Ser Gln Pro His
            665                 670                 675

Arg Ser Leu Arg Glu Leu Leu Ala Ala Cys Trp Asn Ser Gly Leu
            680                 685                 690

Arg Val Asp Gly Ala Ala Leu Asn Leu Thr Ser Cys Cys Ala Pro
            695                 700                 705

Arg Pro Lys Glu Lys Ser Asn Leu Ile Val Arg Arg Gly Cys Thr
            710                 715                 720

Pro Ala Pro Ala Pro Gly
            725

<210> SEQ ID NO 10
<211> LENGTH: 502
<212> TYPE: PRT
<213> ORGANISM: Artificial Sequence
<220> FEATURE:
<223> OTHER INFORMATION: amino acid sequence of Glutathione
      S-transferase-truncated Janus Kinase 3 fusion protein

<400> SEQUENCE: 10

Val Phe Met Ser Pro Ile Leu Gly Tyr Trp Lys Ile Lys Gly Leu
1               5                   10                  15

Val Gln Pro Thr Arg Leu Leu Leu Glu Tyr Leu Glu Glu Lys Tyr
            20                  25                  30

Glu Glu His Leu Tyr Glu Arg Asp Glu Gly Asp Lys Trp Arg Asn
            35                  40                  45

Lys Lys Phe Glu Leu Gly Leu Glu Phe Pro Asn Leu Pro Tyr Tyr
            50                  55                  60

Ile Asp Gly Asp Val Lys Leu Thr Gln Ser Met Ala Ile Ile Arg
            65                  70                  75

Tyr Ile Ala Asp Lys His Asn Met Leu Gly Gly Cys Pro Lys Glu
            80                  85                  90

Arg Ala Glu Ile Ser Met Leu Glu Gly Ala Val Leu Asp Ile Arg
            95                  100                 105

Tyr Gly Val Ser Arg Ile Ala Tyr Ser Lys Asp Phe Glu Thr Leu
            110                 115                 120

Lys Val Asp Phe Leu Ser Lys Leu Pro Glu Met Leu Lys Met Phe
```

```
                        125                 130                 135
Glu Asp Arg Leu Cys His Lys Thr Tyr Leu Asn Gly Asp His Val
                140                 145                 150
Thr His Pro Asp Phe Met Leu Tyr Asp Ala Leu Asp Val Val Leu
                155                 160                 165
Tyr Met Asp Pro Met Cys Leu Asp Ala Phe Pro Lys Leu Val Cys
                170                 175                 180
Phe Lys Lys Arg Ile Glu Ala Ile Pro Gln Ile Asp Lys Tyr Leu
                185                 190                 195
Lys Ser Ser Lys Tyr Ile Ala Trp Pro Leu Gln Gly Trp Gln Ala
                200                 205                 210
Thr Phe Gly Gly Gly Asp His Pro Pro Lys Ser Asp Leu Val Pro
                215                 220                 225
Arg Gly Ser Pro Asn Ser Met Ala Pro Ser Glu Glu Thr Pro
                230                 235                 240
Leu Ile Pro Gln Arg Ser Cys Ser Leu Ser Ser Ser Glu Ala Gly
                245                 250                 255
Ala Leu His Val Leu Leu Pro Pro Arg Gly Pro Gly Pro Pro Gln
                260                 265                 270
Arg Leu Ser Phe Ser Phe Gly Asp Tyr Leu Ala Glu Asp Leu Cys
                275                 280                 285
Val Arg Ala Ala Lys Ala Cys Gly Ile Leu Pro Val Tyr His Ser
                290                 295                 300
Leu Phe Ala Leu Ala Thr Glu Asp Phe Ser Cys Trp Phe Pro Pro
                305                 310                 315
Ser His Ile Phe Cys Ile Glu Asp Val Asp Thr Gln Val Leu Val
                320                 325                 330
Tyr Arg Leu Arg Phe Tyr Phe Pro Asp Trp Phe Gly Leu Glu Thr
                335                 340                 345
Cys His Arg Phe Gly Leu Arg Lys Asp Leu Thr Ser Ala Ile Leu
                350                 355                 360
Asp Leu His Val Leu Glu His Leu Phe Ala Gln His Arg Ser Asp
                365                 370                 375
Leu Val Ser Gly Arg Leu Pro Val Gly Leu Ser Met Lys Glu Gln
                380                 385                 390
Gly Glu Phe Leu Ser Leu Ala Val Leu Asp Leu Ala Gln Met Ala
                395                 400                 405
Arg Glu Gln Ala Gln Arg Pro Gly Glu Leu Leu Lys Thr Val Ser
                410                 415                 420
Tyr Lys Ala Cys Leu Pro Pro Ser Leu Arg Asp Val Ile Gln Gly
                425                 430                 435
Gln Asn Phe Val Thr Arg Arg Ile Arg Arg Thr Val Val Leu
                440                 445                 450
Ala Leu Arg Arg Val Val Ala Cys Gln Ala Asp Arg Tyr Ala Leu
                455                 460                 465
Met Ala Lys Tyr Ile Leu Asp Leu Glu Arg Leu His Pro Ala Ala
                470                 475                 480
Thr Thr Glu Thr Phe Arg Val Leu Pro Gly Ala Gln Glu Glu Pro
                485                 490                 495
Gly Leu Leu Arg Val Ala Gly
                500

<210> SEQ ID NO 11
```

-continued

```
<211> LENGTH: 1388
<212> TYPE: PRT
<213> ORGANISM: Artificial Sequence
<220> FEATURE:
<223> OTHER INFORMATION: amino acid sequence of Glutathione
      S-transferase-Phosphorylated Janus Kinase 3 fusion protein
<220> FEATURE:
<221> NAME/KEY: misc_feature
<222> LOCATION: 603..703
<223> OTHER INFORMATION: region in SH2 domain in which phosphorylation
      occurs
<220> FEATURE:
<221> NAME/KEY: misc_feature
<222> LOCATION: 1202..1251
<223> OTHER INFORMATION: region in PH1 domain in which phosphorylation
      occurs

<400> SEQUENCE: 11

Val Phe Met Ser Pro Ile Leu Gly Tyr Trp Lys Ile Lys Gly Leu
 1               5                  10                  15

Val Gln Pro Thr Arg Leu Leu Leu Glu Tyr Leu Glu Glu Lys Tyr
                20                  25                  30

Glu Glu His Leu Tyr Glu Arg Asp Glu Gly Asp Lys Trp Arg Asn
                35                  40                  45

Lys Lys Phe Glu Leu Gly Leu Glu Phe Pro Asn Leu Pro Tyr Tyr
                50                  55                  60

Ile Asp Gly Asp Val Lys Leu Thr Gln Ser Met Ala Ile Ile Arg
                65                  70                  75

Tyr Ile Ala Asp Lys His Asn Met Leu Gly Gly Cys Pro Lys Glu
                80                  85                  90

Arg Ala Glu Ile Ser Met Leu Glu Gly Ala Val Leu Asp Ile Arg
                95                 100                 105

Tyr Gly Val Ser Arg Ile Ala Tyr Ser Lys Asp Phe Glu Thr Leu
               110                 115                 120

Lys Val Asp Phe Leu Ser Lys Leu Pro Glu Met Leu Lys Met Phe
               125                 130                 135

Glu Asp Arg Leu Cys His Lys Thr Tyr Leu Asn Gly Asp His Val
               140                 145                 150

Thr His Pro Asp Phe Met Leu Tyr Asp Ala Leu Asp Val Val Leu
               155                 160                 165

Tyr Met Asp Pro Met Cys Leu Asp Ala Phe Pro Lys Leu Val Cys
               170                 175                 180

Phe Lys Lys Arg Ile Glu Ala Ile Pro Gln Ile Asp Lys Tyr Leu
               185                 190                 195

Lys Ser Ser Lys Tyr Ile Ala Trp Pro Leu Gln Gly Trp Gln Ala
               200                 205                 210

Thr Phe Gly Gly Gly Asp His Pro Pro Lys Ser Asp Leu Val Pro
               215                 220                 225

Arg Gly Ser Pro Asn Ser Met Ala Pro Ser Glu Glu Thr Pro
               230                 235                 240

Leu Ile Pro Gln Arg Ser Cys Ser Leu Ser Ser Ser Glu Ala Gly
               245                 250                 255

Ala Leu His Val Leu Leu Pro Pro Arg Gly Pro Gly Pro Pro Gln
               260                 265                 270

Arg Leu Ser Phe Ser Phe Gly Asp Tyr Leu Ala Glu Asp Leu Cys
               275                 280                 285

Val Arg Ala Ala Lys Ala Cys Gly Ile Leu Pro Val Tyr His Ser
               290                 295                 300
```

```
Leu Phe Ala Leu Ala Thr Glu Asp Phe Ser Cys Trp Phe Pro Pro
                305                 310                 315

Ser His Ile Phe Cys Ile Glu Asp Val Asp Thr Gln Val Leu Val
            320                 325                 330

Tyr Arg Leu Arg Phe Tyr Phe Pro Asp Trp Phe Gly Leu Glu Thr
                335                 340                 345

Cys His Arg Phe Gly Leu Arg Lys Asp Leu Thr Ser Ala Ile Leu
            350                 355                 360

Asp Leu His Val Leu Glu His Leu Phe Ala Gln His Arg Ser Asp
                365                 370                 375

Leu Val Ser Gly Arg Leu Pro Val Gly Leu Ser Met Lys Glu Gln
            380                 385                 390

Gly Glu Phe Leu Ser Leu Ala Val Leu Asp Leu Ala Gln Met Ala
                395                 400                 405

Arg Glu Gln Ala Gln Arg Pro Gly Glu Leu Leu Lys Thr Val Ser
            410                 415                 420

Tyr Lys Ala Cys Leu Pro Pro Ser Leu Arg Asp Val Ile Gln Gly
                425                 430                 435

Gln Asn Phe Val Thr Arg Arg Ile Arg Arg Thr Val Val Leu
            440                 445                 450

Ala Leu Arg Arg Val Val Ala Cys Gln Ala Asp Arg Tyr Ala Leu
                455                 460                 465

Met Ala Lys Tyr Ile Leu Asp Leu Glu Arg Leu His Pro Ala Ala
            470                 475                 480

Thr Thr Glu Thr Phe Arg Val Gly Leu Pro Gly Ala Gln Glu Glu
                485                 490                 495

Pro Gly Leu Leu Arg Val Ala Gly Asp Asn Gly Ile Ser Trp Ser
            500                 505                 510

Ser Gly Asp Gln Glu Leu Phe Gln Thr Phe Cys Asp Phe Pro Glu
                515                 520                 525

Ile Val Asp Val Ser Ile Lys Gln Ala Pro Arg Val Gly Pro Ala
            530                 535                 540

Gly Glu His Arg Leu Val Thr Val Thr Arg Met Asp Gly His Ile
                545                 550                 555

Leu Glu Ala Glu Phe Pro Gly Leu Pro Glu Ala Leu Ser Phe Val
            560                 565                 570

Ala Leu Val Asp Gly Tyr Phe Arg Leu Ile Cys Asp Ser Arg His
                575                 580                 585

Tyr Phe Cys Lys Glu Val Ala Pro Pro Arg Leu Leu Glu Glu
            590                 595                 600

Ala Glu Leu Cys His Gly Pro Ile Thr Leu Asp Phe Ala Ile His
                605                 610                 615

Lys Leu Lys Ala Ala Gly Ser Leu Pro Gly Thr Tyr Ile Leu Arg
            620                 625                 630

Arg Ser Pro Gln Asp Tyr Asp Ser Phe Leu Leu Thr Ala Cys Val
                635                 640                 645

Gln Thr Pro Leu Gly Pro Asp Tyr Lys Gly Cys Leu Ile Arg Gln
            650                 655                 660

Asp Pro Ser Gly Ala Phe Ser Leu Val Gly Leu Ser Gln Pro His
                665                 670                 675

Arg Ser Leu Arg Glu Leu Leu Ala Ala Cys Trp Asn Ser Gly Leu
            680                 685                 690

Arg Val Asp Gly Ala Ala Leu Asn Leu Thr Ser Cys Cys Ala Pro
```

```
                    695                 700                 705
Arg Pro Lys Glu Lys Ser Asn Leu Ile Val Val Arg Arg Gly Cys
                710                 715                 720

Thr Pro Ala Pro Ala Pro Gly Cys Ser Pro Ser Cys Cys Ala Leu
                725                 730                 735

Thr Gln Leu Ser Phe His Thr Ile Pro Thr Asp Ser Leu Glu Trp
                740                 745                 750

His Glu Asn Leu Gly His Gly Ser Phe Thr Lys Ile Phe Arg Gly
                755                 760                 765

Arg Arg Arg Glu Val Val Asp Gly Glu Thr His Asp Ser Glu Val
                770                 775                 780

Leu Leu Lys Val Met Asp Ser Arg His Arg Asn Cys Met Glu Ser
                785                 790                 795

Phe Leu Glu Ala Ala Ser Leu Met Ser Gln Val Ser Tyr Pro His
                800                 805                 810

Leu Val Leu Leu His Gly Val Cys Met Ala Gly Asp Ser Ile Met
                815                 820                 825

Val Gln Glu Phe Val Tyr Leu Gly Ala Ile Asp Met Tyr Leu Arg
                830                 835                 840

Lys Arg Gly His Leu Val Ser Ala Ser Trp Lys Leu Gln Val Thr
                845                 850                 855

Lys Gln Leu Ala Tyr Ala Leu Asn Tyr Leu Glu Asp Lys Gly Leu
                860                 865                 870

Pro His Gly Asn Val Ser Ala Arg Lys Val Leu Leu Ala Arg Glu
                875                 880                 885

Gly Gly Asp Gly Asn Pro Pro Phe Ile Lys Leu Ser Asp Pro Gly
                890                 895                 900

Val Ser Pro Thr Val Leu Ser Leu Glu Met Leu Thr Asp Arg Ile
                905                 910                 915

Pro Trp Val Ala Pro Glu Cys Leu Gln Glu Ala Gln Thr Leu Cys
                920                 925                 930

Leu Glu Ala Asp Lys Trp Gly Phe Gly Ala Thr Thr Trp Glu Val
                935                 940                 945

Phe Ser Gly Gly Pro Ala His Ile Thr Ser Leu Glu Pro Ala Lys
                950                 955                 960

Lys Leu Lys Phe Tyr Glu Asp Gln Gly Gln Leu Pro Ala Leu Lys
                965                 970                 975

Trp Thr Glu Leu Ala Gly Leu Ile Thr Gln Cys Met Ala Tyr Asp
                980                 985                 990

Pro Gly Arg Arg Pro Ser Phe Arg Ala Ile Leu Arg Asp Leu Asn
                995                 1000                1005

Gly Leu Ile Thr Ser Asp Tyr Glu Leu Leu Ser Asp Pro Thr Pro
                1010                1015                1020

Gly Ile Pro Ser Pro Arg Asp Glu Leu Cys Gly Gly Ala Gln Leu
                1025                1030                1035

Tyr Ala Cys Gln Asp Pro Ala Ile Phe Glu Glu Arg His Leu Lys
                1040                1045                1050

Tyr Ile Ser Leu Leu Gly Lys Gly Asn Phe Gly Ser Val Glu Leu
                1055                1060                1065

Cys Arg Tyr Asp Pro Leu Gly Asp Asn Thr Gly Pro Leu Val Ala
                1070                1075                1080

Val Lys Gln Leu Gln His Ser Gly Pro Asp Gln Gln Arg Asp Phe
                1085                1090                1095
```

```
Gln Arg Glu Ile Gln Ile Leu Lys Ala Leu His Ser Asp Phe Ile
            1100                1105                1110

Val Lys Tyr Arg Gly Val Ser Tyr Gly Pro Gly Arg Gln Ser Leu
            1115                1120                1125

Arg Leu Val Met Glu Tyr Leu Pro Ser Gly Cys Leu Arg Asp Phe
            1130                1135                1140

Leu Gln Arg His Arg Ala Arg Leu His Thr Asp Arg Leu Leu Leu
            1145                1150                1155

Phe Ala Trp Gln Ile Cys Lys Gly Met Glu Tyr Leu Gly Ala Arg
            1160                1165                1170

Arg Cys Val His Arg Asp Leu Ala Ala Arg Asn Ile Leu Val Glu
            1175                1180                1185

Ser Glu Ala His Val Lys Ile Ala Asp Phe Gly Leu Ala Lys Leu
            1190                1195                1200

Leu Pro Leu Gly Lys Asp Tyr Tyr Val Val Arg Glu Pro Gly Gln
            1205                1210                1215

Ser Pro Ile Phe Trp Tyr Ala Pro Glu Ser Leu Ser Asp Asn Ile
            1220                1225                1230

Phe Ser Arg Gln Ser Asp Val Trp Ser Phe Gly Val Val Leu Tyr
            1235                1240                1245

Glu Leu Phe Thr Tyr Cys Asp Lys Ser Cys Ser Pro Ser Ala Glu
            1250                1255                1260

Phe Leu Arg Met Met Gly Pro Glu Arg Glu Gly Pro Pro Leu Cys
            1265                1270                1275

Arg Leu Leu Glu Leu Leu Ala Glu Gly Arg Arg Leu Pro Pro Pro
            1280                1285                1290

Pro Thr Cys Pro Thr Glu Val Gln Glu Leu Met Gln Leu Cys Trp
            1295                1300                1305

Ala Pro Ser Pro His Asp Arg Pro Ala Phe Gly Thr Leu Ser Pro
            1310                1315                1320

Gln Leu Asp Ala Leu Trp Arg Gly Arg Pro Gly Gln Pro Gly Ala
            1325                1330                1335

Arg Val Ser Leu Val Pro Met Ile Trp Leu Cys Asp Leu Arg Gln
            1340                1345                1350

Glu Thr Val Pro Phe Trp Ala Pro Ser Pro Pro Tyr Pro Leu Trp
            1355                1360                1365

Pro Leu Leu Pro Ile Ile Leu Ser Ser Gln Asn Gly Asp Ile Lys
            1370                1375                1380

Tyr Val Arg Pro His Arg Asp Leu
            1385

<210> SEQ ID NO 12
<211> LENGTH: 1030
<212> TYPE: PRT
<213> ORGANISM: Artificial Sequence
<220> FEATURE:
<223> OTHER INFORMATION: amino acid sequence of Glutathione
      S-transferase-Phosphorylated truncated Janus Kinase 3 fusion
      protein
<220> FEATURE:
<221> NAME/KEY: misc_feature
<222> LOCATION: 603..703
<223> OTHER INFORMATION: region in SH2 domain in which phosphorylation
      occurs

<400> SEQUENCE: 12

Val Phe Met Ser Pro Ile Leu Gly Tyr Trp Lys Ile Lys Gly Leu
```

-continued

```
1               5                   10                  15
Val Gln Pro Thr Arg Leu Leu Glu Tyr Leu Glu Glu Lys Tyr
                20                  25                  30
Glu Glu His Leu Tyr Glu Arg Asp Gly Asp Lys Trp Arg Asn
                35                  40                  45
Lys Lys Phe Glu Leu Gly Leu Glu Phe Pro Asn Leu Pro Tyr Tyr
                50                  55                  60
Ile Asp Gly Asp Val Lys Leu Thr Gln Ser Met Ala Ile Ile Arg
                65                  70                  75
Tyr Ile Ala Asp Lys His Asn Met Leu Gly Gly Cys Pro Lys Glu
                80                  85                  90
Arg Ala Glu Ile Ser Met Leu Glu Gly Ala Val Leu Asp Ile Arg
                95                  100                 105
Tyr Gly Val Ser Arg Ile Ala Tyr Ser Lys Asp Phe Glu Thr Leu
                110                 115                 120
Lys Val Asp Phe Leu Ser Lys Leu Pro Glu Met Leu Lys Met Phe
                125                 130                 135
Glu Asp Arg Leu Cys His Lys Thr Tyr Leu Asn Gly Asp His Val
                140                 145                 150
Thr His Pro Asp Phe Met Leu Tyr Asp Ala Leu Asp Val Val Leu
                155                 160                 165
Tyr Met Asp Pro Met Cys Leu Asp Ala Phe Pro Lys Leu Val Cys
                170                 175                 180
Phe Lys Lys Arg Ile Glu Ala Ile Pro Gln Ile Asp Lys Tyr Leu
                185                 190                 195
Lys Ser Ser Lys Tyr Ile Ala Trp Pro Leu Gln Gly Trp Gln Ala
                200                 205                 210
Thr Phe Gly Gly Gly Asp His Pro Pro Lys Ser Asp Leu Val Pro
                215                 220                 225
Arg Gly Ser Pro Asn Ser Met Ala Pro Ser Glu Glu Thr Pro
                230                 235                 240
Leu Ile Pro Gln Arg Ser Cys Ser Leu Ser Ser Ser Glu Ala Gly
                245                 250                 255
Ala Leu His Val Leu Leu Pro Pro Arg Gly Pro Gly Pro Pro Gln
                260                 265                 270
Arg Leu Ser Phe Ser Phe Gly Asp Tyr Leu Ala Glu Asp Leu Cys
                275                 280                 285
Val Arg Ala Ala Lys Ala Cys Gly Ile Leu Pro Val Tyr His Ser
                290                 295                 300
Leu Phe Ala Leu Ala Thr Glu Asp Phe Ser Cys Trp Phe Pro Pro
                305                 310                 315
Ser His Ile Phe Cys Ile Glu Asp Val Asp Thr Gln Val Leu Val
                320                 325                 330
Tyr Arg Leu Arg Phe Tyr Phe Pro Asp Trp Phe Gly Leu Glu Thr
                335                 340                 345
Cys His Arg Phe Gly Leu Arg Lys Asp Leu Thr Ser Ala Ile Leu
                350                 355                 360
Asp Leu His Val Leu Glu His Leu Phe Ala Gln His Arg Ser Asp
                365                 370                 375
Leu Val Ser Gly Arg Leu Pro Val Gly Leu Ser Met Lys Glu Gln
                380                 385                 390
Gly Glu Phe Leu Ser Leu Ala Val Leu Asp Leu Ala Gln Met Ala
                395                 400                 405
```

```
Arg Glu Gln Ala Gln Arg Pro Gly Glu Leu Leu Lys Thr Val Ser
                410                 415                 420

Tyr Lys Ala Cys Leu Pro Pro Ser Leu Arg Asp Val Ile Gln Gly
                425                 430                 435

Gln Asn Phe Val Thr Arg Arg Ile Arg Arg Thr Val Val Leu
                440                 445                 450

Ala Leu Arg Arg Val Val Ala Cys Gln Ala Asp Arg Tyr Ala Leu
                455                 460                 465

Met Ala Lys Tyr Ile Leu Asp Leu Glu Arg Leu His Pro Ala Ala
                470                 475                 480

Thr Thr Glu Thr Phe Arg Val Gly Leu Pro Gly Ala Gln Glu Glu
                485                 490                 495

Pro Gly Leu Leu Arg Val Ala Gly Asp Asn Gly Ile Ser Trp Ser
                500                 505                 510

Ser Gly Asp Gln Glu Leu Phe Gln Thr Phe Cys Asp Phe Pro Glu
                515                 520                 525

Ile Val Asp Val Ser Ile Lys Gln Ala Pro Arg Val Gly Pro Ala
                530                 535                 540

Gly Glu His Arg Leu Val Thr Val Thr Arg Met Asp Gly His Ile
                545                 550                 555

Leu Glu Ala Glu Phe Pro Gly Leu Pro Glu Ala Leu Ser Phe Val
                560                 565                 570

Ala Leu Val Asp Gly Tyr Phe Arg Leu Ile Cys Asp Ser Arg His
                575                 580                 585

Tyr Phe Cys Lys Glu Val Ala Pro Pro Arg Leu Leu Glu Glu Glu
                590                 595                 600

Ala Glu Leu Cys His Gly Pro Ile Thr Leu Asp Phe Ala Ile His
                605                 610                 615

Lys Leu Lys Ala Ala Gly Ser Leu Pro Gly Thr Tyr Ile Leu Arg
                620                 625                 630

Arg Ser Pro Gln Asp Tyr Asp Ser Phe Leu Leu Thr Ala Cys Val
                635                 640                 645

Gln Thr Pro Leu Gly Pro Asp Tyr Lys Gly Cys Leu Ile Arg Gln
                650                 655                 660

Asp Pro Ser Gly Ala Phe Ser Leu Val Gly Leu Ser Gln Pro His
                665                 670                 675

Arg Ser Leu Arg Glu Leu Leu Ala Ala Cys Trp Asn Ser Gly Leu
                680                 685                 690

Arg Val Asp Gly Ala Ala Leu Asn Leu Thr Ser Cys Cys Ala Pro
                695                 700                 705

Arg Pro Lys Glu Lys Ser Asn Leu Ile Val Val Arg Arg Gly Cys
                710                 715                 720

Thr Pro Ala Pro Ala Pro Gly Cys Ser Pro Ser Cys Cys Ala Leu
                725                 730                 735

Thr Gln Leu Ser Phe His Thr Ile Pro Thr Asp Ser Leu Glu Trp
                740                 745                 750

His Glu Asn Leu Gly His Gly Ser Phe Thr Lys Ile Phe Arg Gly
                755                 760                 765

Arg Arg Arg Glu Val Val Asp Gly Glu Thr His Asp Ser Glu Val
                770                 775                 780

Leu Leu Lys Val Met Asp Ser Arg His Arg Asn Cys Met Glu Ser
                785                 790                 795
```

-continued

```
Phe Leu Glu Ala Ala Ser Leu Met Ser Gln Val Ser Tyr Pro His
                800                 805                 810

Leu Val Leu Leu His Gly Val Cys Met Ala Gly Asp Ser Ile Met
            815                 820                 825

Val Gln Glu Phe Val Tyr Leu Gly Ala Ile Asp Met Tyr Leu Arg
        830                 835                 840

Lys Arg Gly His Leu Val Ser Ala Ser Trp Lys Leu Gln Val Thr
    845                 850                 855

Lys Gln Leu Ala Tyr Ala Leu Asn Tyr Leu Glu Asp Lys Gly Leu
860                 865                 870

Pro His Gly Asn Val Ser Ala Arg Lys Val Leu Leu Ala Arg Glu
                875                 880                 885

Gly Gly Asp Gly Asn Pro Pro Phe Ile Lys Leu Ser Asp Pro Gly
            890                 895                 900

Val Ser Pro Thr Val Leu Ser Leu Glu Met Leu Thr Asp Arg Ile
        905                 910                 915

Pro Trp Val Ala Pro Glu Cys Leu Gln Glu Ala Gln Thr Leu Cys
    920                 925                 930

Leu Glu Ala Asp Lys Trp Gly Phe Gly Ala Thr Thr Trp Glu Val
935                 940                 945

Phe Ser Gly Gly Pro Ala His Ile Thr Ser Leu Glu Pro Ala Lys
                950                 955                 960

Lys Leu Lys Phe Tyr Glu Asp Gln Gly Gln Leu Pro Ala Leu Lys
            965                 970                 975

Trp Thr Glu Leu Ala Gly Leu Ile Thr Gln Cys Met Ala Tyr Asp
        980                 985                 990

Pro Gly Arg Arg Pro Ser Phe Arg Ala Ile Leu Arg Asp Leu Asn
    995                 1000                1005

Gly Leu Ile Thr Ser Asp Tyr Glu Leu Leu Ser Asp Pro Pro Gly
                1010                1015                1020

Ile Pro Ser Pro Arg Asp Glu Leu Cys Gly
            1025                1030

<210> SEQ ID NO 13
<211> LENGTH: 726
<212> TYPE: PRT
<213> ORGANISM: Artificial Sequence
<220> FEATURE:
<223> OTHER INFORMATION: amino acid sequence of Glutathione
      S-transferase-Phosphorylated truncated Janus Kinase 3 fusion
      protein
<220> FEATURE:
<221> NAME/KEY: misc_feature
<222> LOCATION: 603..703
<223> OTHER INFORMATION: region in SH2 domain in which phosphorylation
      occurs

<400> SEQUENCE: 13

Val Phe Met Ser Pro Ile Leu Gly Tyr Trp Lys Ile Lys Gly Leu
1               5                   10                  15

Val Gln Pro Thr Arg Leu Leu Leu Glu Tyr Leu Glu Glu Lys Tyr
                20                  25                  30

Glu Glu His Leu Tyr Glu Arg Asp Glu Gly Asp Lys Trp Arg Asn
            35                  40                  45

Lys Lys Phe Glu Leu Gly Leu Glu Phe Pro Asn Leu Pro Tyr Tyr
        50                  55                  60

Ile Asp Gly Asp Val Lys Leu Thr Gln Ser Met Ala Ile Ile Arg
    65                  70                  75
```

-continued

```
Tyr Ile Ala Asp Lys His Asn Met Leu Gly Gly Cys Pro Lys Glu
                 80                  85                  90

Arg Ala Glu Ile Ser Met Leu Glu Gly Ala Val Leu Asp Ile Arg
             95                 100                 105

Tyr Gly Val Ser Arg Ile Ala Tyr Ser Lys Asp Phe Glu Thr Leu
            110                 115                 120

Lys Val Asp Phe Leu Ser Lys Leu Pro Glu Met Leu Lys Met Phe
            125                 130                 135

Glu Asp Arg Leu Cys His Lys Thr Tyr Leu Asn Gly Asp His Val
            140                 145                 150

Thr His Pro Asp Phe Met Leu Tyr Asp Ala Leu Asp Val Val Leu
            155                 160                 165

Tyr Met Asp Pro Met Cys Leu Asp Ala Phe Pro Lys Leu Val Cys
            170                 175                 180

Phe Lys Lys Arg Ile Glu Ala Ile Pro Gln Ile Asp Lys Tyr Leu
            185                 190                 195

Lys Ser Ser Lys Tyr Ile Ala Trp Pro Leu Gln Gly Trp Gln Ala
            200                 205                 210

Thr Phe Gly Gly Gly Asp His Pro Pro Lys Ser Asp Leu Val Pro
            215                 220                 225

Arg Gly Ser Pro Asn Ser Met Ala Pro Ser Glu Glu Thr Pro
            230                 235                 240

Leu Ile Pro Gln Arg Ser Cys Ser Leu Ser Ser Ser Glu Ala Gly
            245                 250                 255

Ala Leu His Val Leu Leu Pro Pro Arg Gly Pro Gly Pro Pro Gln
            260                 265                 270

Arg Leu Ser Phe Ser Phe Gly Asp Tyr Leu Ala Glu Asp Leu Cys
            275                 280                 285

Val Arg Ala Ala Lys Ala Cys Gly Ile Leu Pro Val Tyr His Ser
            290                 295                 300

Leu Phe Ala Leu Ala Thr Glu Asp Phe Ser Cys Trp Phe Pro Pro
            305                 310                 315

Ser His Ile Phe Cys Ile Glu Asp Val Asp Thr Gln Val Leu Val
            320                 325                 330

Tyr Arg Leu Arg Phe Tyr Phe Pro Asp Trp Phe Gly Leu Glu Thr
            335                 340                 345

Cys His Arg Phe Gly Leu Arg Lys Asp Leu Thr Ser Ala Ile Leu
            350                 355                 360

Asp Leu His Val Leu Glu His Leu Phe Ala Gln His Arg Ser Asp
            365                 370                 375

Leu Val Ser Gly Arg Leu Pro Val Gly Leu Ser Met Lys Glu Gln
            380                 385                 390

Gly Glu Phe Leu Ser Leu Ala Val Leu Asp Leu Ala Gln Met Ala
            395                 400                 405

Arg Glu Gln Ala Gln Arg Pro Gly Glu Leu Leu Lys Thr Val Ser
            410                 415                 420

Tyr Lys Ala Cys Leu Pro Pro Ser Leu Arg Asp Val Ile Gln Gly
            425                 430                 435

Gln Asn Phe Val Thr Arg Arg Arg Ile Arg Arg Thr Val Val Leu
            440                 445                 450

Ala Leu Arg Arg Val Val Ala Cys Gln Ala Asp Arg Tyr Ala Leu
            455                 460                 465
```

```
Met Ala Lys Tyr Ile Leu Asp Leu Glu Arg Leu His Pro Ala Ala
                470                 475                 480
Thr Thr Glu Thr Phe Arg Val Gly Leu Pro Gly Ala Gln Glu Glu
                485                 490                 495
Pro Gly Leu Leu Arg Val Ala Gly Asp Asn Gly Ile Ser Trp Ser
                500                 505                 510
Ser Gly Asp Gln Glu Leu Phe Gln Thr Phe Cys Asp Phe Pro Glu
                515                 520                 525
Ile Val Asp Val Ser Ile Lys Gln Ala Pro Arg Val Gly Pro Ala
                530                 535                 540
Gly Glu His Arg Leu Val Thr Val Thr Arg Met Asp Gly His Ile
                545                 550                 555
Leu Glu Ala Glu Phe Pro Gly Leu Pro Glu Ala Leu Ser Phe Val
                560                 565                 570
Ala Leu Val Asp Gly Tyr Phe Arg Leu Ile Cys Asp Ser Arg His
                575                 580                 585
Tyr Phe Cys Lys Glu Val Ala Pro Pro Arg Leu Leu Glu Glu Glu
                590                 595                 600
Ala Glu Leu Cys His Gly Pro Ile Thr Leu Asp Phe Ala Ile His
                605                 610                 615
Lys Leu Lys Ala Ala Gly Ser Leu Pro Gly Thr Tyr Ile Leu Arg
                620                 625                 630
Arg Ser Pro Gln Asp Tyr Asp Ser Phe Leu Leu Thr Ala Cys Val
                635                 640                 645
Gln Thr Pro Leu Gly Pro Asp Tyr Lys Gly Cys Leu Ile Arg Gln
                650                 655                 660
Asp Pro Ser Gly Ala Phe Ser Leu Val Gly Leu Ser Gln Pro His
                665                 670                 675
Arg Ser Leu Arg Glu Leu Leu Ala Ala Cys Trp Asn Ser Gly Leu
                680                 685                 690
Arg Val Asp Gly Ala Ala Leu Asn Leu Thr Ser Cys Cys Ala Pro
                695                 700                 705
Arg Pro Lys Glu Lys Ser Asn Leu Ile Val Arg Arg Gly Cys Thr
                710                 715                 720
Pro Ala Pro Ala Pro Gly
                725
```

METHODS OF SCREENING FOR JANUS KINASE 3 INTERACTING COMPOUNDS

CROSS-REFERENCE TO RELATED APPLICATION

This application is a continuation-in-part under 35 U.S.C. §120 of pending non-provisional application U.S. Ser. No. 14/483,622, filed Sep. 11, 2014, which claims benefit of priority under 35 U.S.C. §119(e) of provisional application U.S. Ser. No. 61/960,652, filed Sep. 23, 2013, now abandoned, the entirety of both of which are hereby incorporated by reference.

BACKGROUND OF THE INVENTION

Field of the Invention

The present invention is in the field of pre-clinical therapeutics. More specifically, the present invention is directed to a method of screening synthetic and natural compounds for Janus Kinase 3 (Jak3) modulating activity.

Description of the Related Art

Janus Kinases (Jaks) are a family of non-receptor tyrosine kinase with four members; Jak1, Jak2, Jak3, and Tyk2, that transduce cytokine-mediated signals through interactions with the common γ chain of the immune receptors for IL-2, 1L-5, IL-7, IL-9, and IL-15 (1). Several studies have shown that deficiency or over-activation of Jak3 in particular, results in a multitude of disorders including, autoimmunity (2), arthritis (3) allergy (4,5), cancer (6-8), diabetes (9,10), immune deficiencies (11-13), transplant rejection (14-17) and neuromuscular diseases (18). Therefore, synthetic compounds and biomolecules that modulate Jak3 functions, without compromising normal immune functions are valuable in the treatment of these diseases.

While widely expressed in different organs in both humans and mice, Jak3 shows significant expression in the cells of the epithelial and hematologic lineages (1,19-20). In agreement with this distribution, abnormal Jak3 activation is associated with human hematologic and epithelial malignancies (21, 22).

Pharmacological inhibitors of Jak3 have shown utility in autoimmune disorders, acute lymphoblastic leukemia, Type 1 diabetes, rheumatoid arthritis, allergy and asthma. While, many of these have demonstrated promise in clinical trials, there is a need to develop sensitive, selective and reproducible tools for identifying synthetic and natural compounds that modulate Jak3 function.

The N-terminal region of Jak3 (about 550 amino acids) is known to interact not only with the cytoplasmic tail of the cytokine receptors discussed above, but also to cytoskeletal and adapter proteins. This region further contains a four-point-one ezrin/radixin/moesin (FERM) domain (23) that is implicated in cell-cell communication and cell adhesion (24), important contributors to cell motility. Thus, targeting the FERM domain is expected to inhibit kinase activity and in addition, disrupt Jak3/cytokine receptor engagement. The present invention offers a high-throughput screening method to rapidly identify compounds in tandem, for their ability to interact with the FERM domain and/or the kinase domain, with desired end use as therapeutics in the management of Jak3-associated diseases.

Currently available methods for identifying Jak3 regulators employ the kinase domain of Jak3 in two popular formats viz; (a) Caliper format and (b) Perkin Elmer format. Caliper's mobility shift assay (Caliper Life Science, Hopkinton, Mass.) uses a nanofluid-based technology, which involves electrophoretic separation of fluorescently labeled phosphorylated and non-phosphorylated substrates on a microchip, followed by fluorimetric quantification. Additionally, the reactions are run on a chip or in micro-plate wells with the microchip being used solely to separate the substrate from the phosphorylated product. The main limitation of this technology is use of external peptide substrate and the need to screen an efficient substrate that can fit into this technology. Screening of these substrates introduces yet another layer of complexity, in addition to being expensive on account of instrument and manpower costs.

Perkin Elmer's (Waltham, Mass.) Streptavidin-coated Flashplate radiometric assay differs from Caliper's assay in the use of a radiolabeled external substrate. This method uses one of three ways to assess phosphorylation: (1) measuring ATP depletion (easy-Lite-Kinase), (2) direct measurement of phosphate incorporation in the substrate using $^{33}$P-labeled ATP (FLASHPLATE), or (3) capture and measurement of phosphorylated substrate (ALPHASCREEN, Lance, DELFIA).

Another technology marketed by Dynamii Pharmaceticals (DynamixFit) also uses the kinase-only domain of Jak3, but rather than using the classical "lock and key" enzyme model, it utilizes an "induced fit" model, which is based on the concept that, enzymes being flexible proteins, have 3D active-site structures that are continuously reshaped by interactions with their substrates (or inhibitors).

Overall, there is a deficiency in the art for optimal screening tools, due to limitations imposed by use of kinase-only domains and external substrates, that is further complicated due to sensitivity, need for radioactive detection, absence of a user-friendly interface and poor cost-effectiveness. Thus, there is a recognized need for improved methods to screen Jak3 regulators. The present invention fulfills this longstanding need and desire in the art.

SUMMARY OF THE INVENTION

The present invention is directed to a method of screening synthetic and natural compounds that inhibit Jak3 autophosphorylation, in the absence of an external substrate.

This invention is also directed to a method of screening synthetic and natural compounds that bind Jak3 or its truncated, domain-deleted mutants.

This invention also describes development of a screening kit comprising a recombinant Jak3 protein, to identify compounds that inhibit Jak3 autophosphorylation.

This invention further describes development of a screening kit comprising, a plurality of recombinant, Jak3 proteins and Jak3 fusion proteins including, truncated Jak3 fusion proteins. This kit further comprises instructions to identify compounds that inhibit Jak3 autophosphorylation, and to identify compounds that bind full-length Jak3 and/or truncated Jak3.

Other and further aspects, features, benefits, and advantages of the present invention will be apparent from the following description of the presently preferred embodiments of the invention given for the purpose of disclosure.

BRIEF DESCRIPTION OF THE DRAWINGS

FIGS. 1A-1E show the cDNA sequences for WT and domain deleted mutants of Jak3, which were cloned (26) in a pGEX-4T vector. FIG. 1A shows the cDNA sequence encoding the WT-Jak3 (full length) (SEQ ID NO: 1). FIG. 1B shows the cDNA sequence encoding the GST-WT-Jak3 fusion protein (SEQ ID NO: 2). FIG. 1C shows the cDNA sequence encoding the GST-Jak3 fusion protein lacking the JH1 domain (SEQ ID NO: 3). FIG. 1D shows the cDNA sequence encoding GST-Jak3 fusion protein lacking the JH1 and JH2 domains (SEQ ID NO: 4). FIG. 1E shows the cDNA sequence encoding the GST-Jak3 fusion protein lacking the JH1, JH2, JH3, and JH4 domains (SEQ ID NO: 5).

FIGS. 2A-2E show the schematic representation and the amino acid sequences for WT and domain-deleted mutants of Jak3, expressed in a *E. coli* BL21 and where indicated, their phosphorylated forms expressed in a *E. coli* TKX1 protein expression system. FIG. 2A shows the schematic representation and the amino acid sequence of the WT-Jak3 (full length) recombinant protein (SEQ ID NO: 6). FIG. 2B shows the schematic representation and the amino acid sequence of the non-phosphorylated GST-WT-Jak3 fusion protein (SEQ ID NO: 7) and phosphorylated GST-WT-Jak3 fusion protein (SEQ ID NO: 11) Underlined amino acid sequences 603-703 and 1202-1251 correspond to the regions in the SH2 and JH1 domain sequences in which phosphorylation occurs, respectively. FIG. 2C shows the schematic representation and the amino acid sequence of the GST-Jak3 fusion protein lacking the JH1 domain (SEQ ID NO: 8) and phosphorylated GST-Jak3 fusion protein lacking the JH1 domain (SEQ ID NO: 12). FIG. 2D shows the schematic representation and the amino acid sequence of the GST-truncated Jak3 fusion protein lacking the JH1 and JH2 domains (SEQ ID NO: 9) and phosphorylated GST-truncated Jak3 fusion protein lacking the JH1 and JH2 domains (SEQ ID NO: 13). Underlined amino acids 603-703 corresponds to the SH2 domain sequence in which phosphorylation occurs in FIGS. 2D-2E. FIG. 2E shows the schematic representation and the amino acid sequence of the GST-truncated Jak3 fusion protein lacking the JH1, JH2, JH3 and JH4 domains (SEQ ID NO: 10).

FIGS. 3A-3B show expression and purification of recombinant Jak3 proteins and recombinant Glutathione-S-transferase (GST)-Jak3 fusion proteins. FIG. 3A Immunoblotting (IB) analysis of purified recombinant proteins expressed in BL21 and TKX1 cells. A phospho-tyrosine specific antibody (pY20) was used to visualize phosphorylated Jak3 and a Jak3 antibody was used to visualize both non-phosphorylated and phosphorylated Jak3. These data demonstrate that only the TKX1 expressed protein is phosphorylated. FIG. 3B shows western blot analyses of the purified recombinant fusion proteins expressed in bacteria. Anti-GST antibody was used as the primary antibody and HRP-conjugated secondary antibody was used to visualize the fusion proteins. Arrows indicate recombinant proteins.

FIG. 6A shows binding of Jak3 to the cytoskeletal protein, Villin, measured in 96-well ELISA multiplates pre-coated with phospho-Villin (P-Villin), and using increasing concentrations of GST-P-Jak3 fusion protein ranging from 0 μM to 600 μM. GST is the reporter protein and the primary binding partner is a GST antibody. FIG. 6B represents the Hill equation plot of the data from FIG. 6A, and shows the relation between the log Y/(1−Y) and log (Jak3), where Y is the fractional saturation of absorbance.

FIG. 7A shows binding of Jak3 with the adapter protein, p52ShcA, measured in 96-well ELISA multiplate pre-coated with phospho-p52ShcA, and using increasing concentrations of GST-P-Jak3 fusion protein, ranging from 0 μM to 600 μM. GST is the reporter protein and the primary binding partner is a GST antibody. FIG. 7B shows a Hill equation plot of the data from FIG. 7A, and shows the relation between the log Y/(1−Y) and log (Jak3), where Y is the fractional saturation of absorbance.

FIG. 8A shows direct interactions between Villin and, recombinant, GST-Jak3 or its indicated truncated-Jak3 mutants, or GST-P-Jak3 or its truncated mutants. Absorbance values for wells containing P-Villin contacted with GST alone were used as control, and data presented on the ordinate axis represent absorbance values after subtraction of control values. FIG. 8B shows binding of GST-Jak3G257 to the cytoskeletal protein, Villin, measured in 96-well ELISA multiplates pre-coated with phospho-Villin (P-Villin), and using increasing concentrations of GST-Jak3-G257 ranging from 0 μM to 20 μM.

DETAILED DESCRIPTION OF THE PRESENT INVENTION

Figure 4:
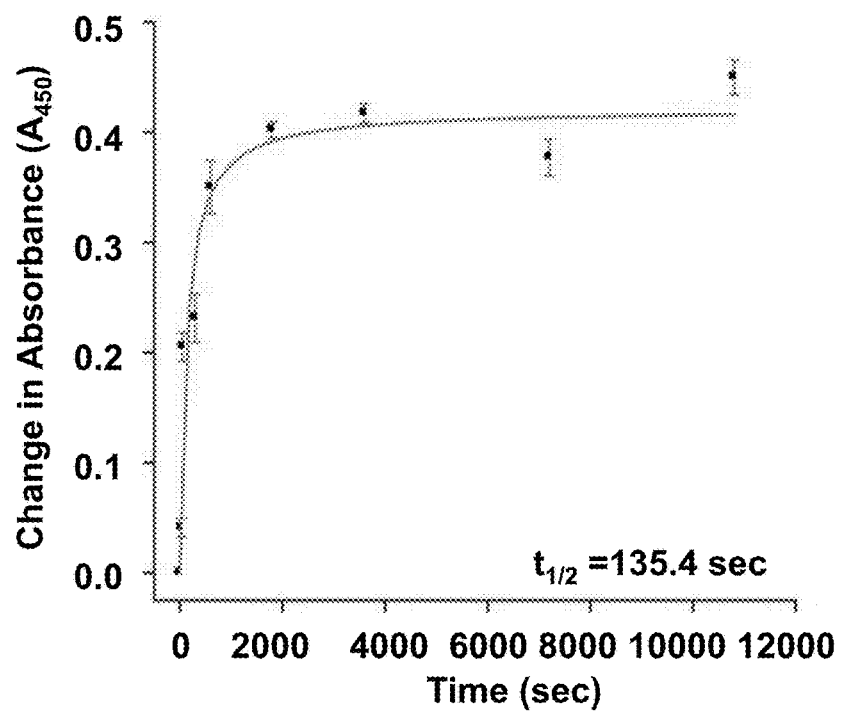
FIG. 4 shows time-dependent changes in tyrosine autophosphorylation of recombinant wild-type Jak3 in the presence or absence (control) of ATP using a 96-well ELISA multiplate coated with GST-Jak3 and the phospho-tyrosine specific antibody, pY20 as the primary binding partner. Measurements were made for a times ranging from 0 to 200 minutes.

For convenience, before further description of the present invention, certain terms employed in the specification, examples and appended claims are collected herein. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" when used in conjunction with the term "comprising" in the claims and/or the specification, may refer to "one", but it is also consistent with the meaning of one or more", at least one", and "one or more than one". Some embodiments of the invention may consist of or consist essentially of one or more elements, components, method steps, and/or methods of the invention. It is contemplated that any composition, component or method described herein can be implemented with respect to any other composition, component or method described herein.

The term "or" in the claims refers to "and/or" unless explicitly indicated to refer to alternatives only or the alternatives are mutually exclusive, although the disclosure supports a definition that refers to only alternatives and "and/or".

The terms "comprise" and "comprising" are used in the inclusive, open sense, meaning that additional elements may be included.

The term "including" is used herein to mean "including, but not limited to". "Including" and "including but not limited to" are used interchangeably.

Provided in the present invention are screening tools to identify not only Jak3 inhibiting compounds but also compounds that interact with Jak3 without interfering with Jak3 activation. Such interacting compounds have implications in treatment of diseases where normal kinase functions of Jak3 are desired, but the disease causing functions of Jak3 are undesirable. For example, biomolecules contribution to cell motility, such as the cytoskeletal proteins Villin and gelsolin, were determined, using this invention, to interact with Jak3 domains other than the kinase domain. Similarly, this invention was used to identify interactions between adapter protein, p52ShcA and Jak3, such interactions positively contributing to cell migration. Screening for compounds that interact with Jak3 therefore finds utility in cancer treatment, since these compounds may be employed to interfere with cancer cell migration, which is central to metastatic spread of the disease, the primary cause of fatalities in cancer. Similarly, screening for Jak3 interacting compounds also finds utility in preventing spurious immune cell migration in allergy and autoimmune disease, The present invention is directed to a method for screening for a compound that inhibits Jak3 protein, comprising the steps of; selecting a potential inhibitory compound; contacting, a phosphate donor with a recombinant Jak3 protein and the potential inhibitory compound in a first sample; contacting said phosphate donor with the recombinant Jak3 protein in a second control sample; and measuring a level of autophosphorylation of said Jak3 protein in the first sample and in the second sample; wherein a reduction in the level of Jak3 autophosphorylation in the first sample compared to the level in the second control sample indicates that the compound inhibits Jak3 protein.

Potential inhibitory compounds that may be selected for screening include, synthetic compounds, their derivatives and analogs; chemical libraries; synthetic peptides, natural peptides, their derivatives and analogs; peptide libraries; proteins, modified proteins, antibodies or their fragments thereof; synthetic and natural lipids including, fatty acids, phospholipids, sterols, their derivatives and analogs; synthetic and natural sugars, including, monosaccharides, disaccharides, their derivatives and analogs.

In one embodiment, the method of screening compounds that inhibit Jak3 autophosphorylation encompasses use of a recombinant full length Jak3 protein. This Jak3 protein may be produced in a bacterial, yeast, insect or mammalian host cell that is transduced with the appropriate vector comprising the cDNA sequence of said Jak3 protein, using methods well known in the art.

In a second embodiment, the method of screening compounds that inhibit Jak3 autophosphorylation comprises use of a recombinant full length Jak3-fusion protein that is attached at the N-terminus to a reporter molecule.

In a preferred embodiment, the reporter molecule attached to the N-terminus of the Jak3 proteins discussed supra may be a peptide such a poly(histidine)$_x$-tag, where x=6 or 10 histidine molecules, attached either directly to the N-terminus sequence of said Jak3, or attached via a linker amino acid sequence, to the N-terminus of Jak3. Methods for attaching the poly(histidine) tag nucleotide sequence, with or without the linker amino acid nucleotide sequence, upstream to the nucleotide sequence of said Jak3 protein(s), and methods to package these sequences in vectors so as to express fusion proteins in high yield, are well known in the art (25).

Alternatively, the reporter molecule may be a FLAG-tag, 3xFLAG-tag, a human influenza hemagglutinin (HA)-tag or a myc-tag, all of which are also well known in the art and may be attached upstream to the Jak3 sequence as discussed supra. In a preferred embodiment, the reporter molecule is glutathione-S-transferase (GST).

The method of screening for compounds inhibiting Jak3 autophosphorylation encompasses use of a high-energy phosphate donor. Such phosphate donors include, nucleotide triphosphates, nucleotide diphosphates, nucleotide monophosphates, their derivatives and analogs. In a preferred embodiment, the phosphate donor is a nucleotide triphosphate, wherein the nucleoside is adenosine or guanosine, and in a more preferred embodiment, the phosphate donor is adenosine triphosphate. In other embodiments, the phosphate donor may be generated in situ using a high-energy phosphate regenerating system such as an ATP-regenerating system, which is well known in the art.

The method further encompasses measuring the level of Jak3 autophosphorylation in the test sample. In one embodiment, this includes use of primary binding partners such as, peptides, or, antibodies or their fragments thereof, which selectively bind to the phosphotyrosine moiety, or bind selectively to phosphorylated Jak3 but not to non-phosphorylated Jak3. In a more preferred embodiment, such a binding partner would be an immunologic binding partner including, a monoclonal antibody having specificity to phosphorylated-Jak3.

The measurement step further encompasses methods and reagents for quantitating binding of the primary binding partner to autophosphorylated Jak3. These include, radiometric, preferably, fluorimetric and more preferably, colorimetric methods.

In one embodiment of the quantitation method, a radioisotope is conjugated directly to the primary binding partner. Alternately, the radioisotope is conjugated to a secondary molecule such as a secondary antibody, which binds specifically to the primary binding partner. Examples of radioisotopes that may be used for this purpose include, gamma emitters like $^{125}$Iodine, beta emitters like $^{14}$Carbon and alpha emitters like $^3$H (tritium).

In a preferred embodiment of the quantitating step, a fluorophore is conjugated directly to the primary binding partner, or to a secondary molecule such as a secondary antibody, which binds specifically to the primary binding partner.

Alternatively, quantitation by use of the fluorimetric method is by a proximity assay such as, Förster resonance energy transfer (FRET), in which the primary and the secondary binding partners are each conjugated with a donor or acceptor fluorophore that constitute a resonance energy transfer system. Examples of such fluorophore pairs known in the art include, FITC/Rhodamine, Alexa488/Rhodamine and Cy3/Cy5. In yet another modification of the FRET proximity assay, the donor/acceptor pairs are selected such that binding of the secondary binding partner to the primary binding partner results in a reduction in fluorescence quantum yields due to quenching. Examples of such reagents include the fluorophore/quencher pairs; Alexa488/Dabcyl and Cy3/DDQ II.

A more preferred embodiment of the method of quantitation is the colorimetric assay, which uses an enzyme-linked antibody to drive a colorimetric reaction. Such enzymes are known in the art to include, horseradish peroxidase and alkaline phosphate that catalyze the release of colored dyes, concentration of the dye directly correlating with the level of phosphorylated Jak3.

In all of the above instances, data analysis includes comparison of the test sample with control samples. Examples of control samples include, contacting the recombinant Jak3 protein with the phosphate donor in the absence of the potential inhibitory compound (positive control sample) and contacting the potential inhibitory compound with the phosphate donor in the absence of recombinant Jak3 (negative control sample).

This invention is also directed to a method for screening for a compound that binds Jak3 protein comprising the steps of selecting a potential binding compound; contacting a recombinant Jak3 fusion protein comprising a reporter protein with the potential binding compound in a first sample; contacting said reporter protein with the potential binding compound in a second control sample; and, measuring a level of binding in the first sample and in the second control sample; wherein an increase in the level of binding of the potential binding compound in the first sample compared to the level of binding in the second control sample indicates that the compound binds Jak3 protein.

Potential binding compounds that may be selected for screening include, synthetic compounds, their derivatives and analogs; chemical libraries; synthetic peptides, natural peptides, their derivatives and analogs; peptide libraries; proteins, modified proteins, antibodies or their fragments thereof; synthetic and natural lipids including, fatty acids, phospholipids, sterols, their derivatives and analogs; synthetic and natural sugars, including, monosaccharides, disaccharides, their derivatives and analogs.

In one embodiment, the method of screening compounds that bind Jak3 encompasses use of a recombinant full length Jak3 protein. This Jak3 protein may be produced in a bacterial, yeast, insect or mammalian host cell that is transduced with the appropriate vector comprising the cDNA sequence of said Jak3 protein, using methods well known in the art.

The method of screening also encompasses use of recombinant Jak3 protein(s) truncated to contain only one of the domains, JH1 (C-terminus) to JH7 (N-terminus), or sequentially truncated to exclude domains JH1 to JH6 (truncation from the C-terminus) or JH7 to JH2 (truncation from the N-terminus). Such truncated mutant Jak3 proteins may be produced in a bacterial, yeast, insect or mammalian host cell that is transduced with the appropriate vector comprising the cDNA sequence of said truncated Jak3 protein(s), using methods well known in the art.

In a second embodiment, the method of screening compounds that bind Jak3 comprises use of a recombinant full length Jak3-fusion protein that is attached at the N-terminus to a reporter molecule. The method also comprises use of recombinant truncated-Jak3 fusion protein(s) that is attached at the N-terminus to a reporter molecule. In this case, the Jak3 is truncated to contain only one of the domains, JH1 (C-terminus) to JH7 (N-terminus), or truncated to exclude one or a multiplicity of domains JH1 to JH6 (truncation from the C-terminus) or JH7 to JH2 (truncation from the N-terminus). Both the recombinant full length Jak3-fusion protein and the truncated mutant Jak3-fusion proteins may be produced in a bacterial, yeast, insect or mammalian host cell that is transduced with the appropriate vector comprising the cDNA sequence of said truncated Jak3 protein(s), using methods well known in the art.

In a third embodiment, the method of screening compounds that bind Jak3 comprises use of a recombinant phosphorylated full length Jak3-fusion protein that is attached at the N-terminus to a reporter molecule. The method also comprises use of a recombinant phosphorylated truncated-Jak3 fusion protein(s) that is attached at the N-terminus to a reporter molecule. In this case, the Jak3 is truncated to contain only one of the domains, JH1 (C-terminus) to JH7 (N-terminus), or truncated to exclude one or a multiplicity of domains JH1 to JH6 (truncation from the C-terminus) or JH7 to JH2 (truncation from the N-terminus). Both the recombinant phosphorylated Jak3-fusion protein and the phosphorylated truncated mutant Jak3-fusion proteins may be produced in a bacterial, yeast, insect or mammalian expression system and preferably in a TKX1 bacterial expression system. Such expression hosts will be transduced with the appropriate vector comprising the cDNA sequence of said truncated Jak3 protein(s), using methods well known in the art.

In a preferred embodiment, the reporter molecule attached to the N-terminus of the Jak3 proteins discussed supra may be a peptide such a poly(histidine)$_x$-tag, where x=6 or 10 histidine molecules, attached either directly to the N-terminus sequence of said Jak3, or attached via a linker amino acid sequence, to the N-terminus of Jak3. Methods for attaching the poly(histidine) tag nucleotide sequence, with or without the linker amino acid nucleotide sequence, upstream to the nucleotide sequence of said Jak3 protein(s), and methods to package these sequences in vectors, so as to express fusion proteins in high yield, are well known in the art (25). Alternatively, the reporter molecule may be a FLAG-tag, 3xFLAG-tag, a human influenza hemagglutinin (HA)-tag or a myc-tag, all of which are also well known in the art and may be attached upstream to the Jak3 nucleotide sequence as discussed supra.

In a more preferred embodiment, the reporter molecule may be a bioluminescent protein, including Renilla luciferase, Nano-lantern, Yellow fluorescent protein or, a florescent protein including, green fluorescent protein, red fluorescent protein, cyan fluorescent protein or yellow fluorescent protein. In a most preferred embodiment, the reporter molecule is glutathione-S-transferase (GST).

The method of screening for compounds that bind Jak3 or its truncated mutants or phosphorylated Jak3 or phoshorylated truncated Jak3 discussed supra also encompasses measuring the level of Jak3 binding in the test sample. In one embodiment, this includes, measurement of fluorescence quantum yields using a fluorescent protein reporter. Such reporters may include, green fluorescent protein, red fluorescent protein, cyan fluorescent protein or yellow fluorescent protein. In a second embodiment, measurement is by luminescence using a bioluminescent protein reporter. Such reporters include, Renilla luciferase, Nano-lantern and Yellow fluorescent protein among others. In a third, preferred embodiment, primary binding partners including an immunologic binding partner may be used. These include, antibodies or their fragments thereof, which selectively bind to the reporter molecule. Examples of such reporter molecules include, poly(histidine)-tag, HA-tag, FLAG-tag, myc-tag and GST-tag.

In a preferred embodiment, the immunologic binding partner is a polyclonal antibody, and in a more preferred embodiment, the immunologic binding partner is a monoclonal antibody. In a most preferred embodiment the reporter is GST and the primary binding partner is a monoclonal GST antibody.

For the methods not employing fluorescent or luminescent reporters, the measurement step further encompasses methods and reagents for quantitating binding of said primary binding partner to the reporter-Jak3 or the reporter-truncated Jak3 fusion proteins. These include, preferably, radiometric, more preferably, fluorimetric and most preferably, colorimetric methods.

In one embodiment of the quantitation method, a radioisotope is conjugated directly to the said primary binding partner. Alternately, the radioisotope is conjugated to a secondary molecule such as a secondary antibody, which binds specifically to the primary binding partner. Examples of radioisotopes that may be used for this purpose include, gamma emitters like $^{125}$Iodine, beta emitters like $^{14}$Carbon and alpha emitters like $^3$H (tritium).

In a more preferred embodiment of the quantitating step, a fluorophore is conjugated directly to the said, primary binding partner, or to a secondary molecule such as a secondary antibody, which binds specifically to the primary binding partner.

Alternatively, quantitation by use of the fluorimetric method is by a proximity assay such as, Förster resonance energy transfer (FRET), in which the primary and the secondary binding partners are each conjugated with a donor or acceptor fluorophore that constitute a resonance energy transfer system. Examples of such fluorophore pairs known in the art include, FITC/Rhodamine, Alexa488/Rhodamine and Cy3/Cy5. In yet another modification of the FRET proximity assay, the donor/acceptor pairs are selected such that binding of the immunologic binding partner to the reporter-Jak3 or the reporter-truncated Jak3 fusion protein, results in a reduction in fluorescence quantum yields due to quenching. Examples of such reagents include the fluorophore/quencher; Alexa488/Dabcyl and Cy3/DDQ II.

A most preferred embodiment of the method of quantitation is the colorimetric assay, which uses an enzyme-linked antibody to drive a colorimetric reaction. Such enzymes are known in the art to include, horseradish peroxidase and alkaline phosphate that catalyze the release of colored dyes, concentration of the dye directly correlating with the level of bound Jak3 or bound truncated Jak3.

In all of the above instances, data analysis includes comparison of the test sample with control samples. Examples of control samples include, contacting the reporter-Jak3 or the reporter-truncated Jak3 fusion protein with the cytoskeletal protein Villin (positive control sample) whereas the negative control sample may, for example, when doing protein-protein interactions, BSA alone or GST alone.

This invention is also directed to a screening kit comprising a recombinant Jak3 protein and instructions for using this to screen for a compound that inhibits Jak3 autophosphorylation. In a preferred embodiment, the recombinant Jak3 protein has a sequence shown in SEQ ID NO: 6 or SEQ ID NO: 7. The instructions provide methods to perform the Jak3 autophosphorylation assay in the presence of the potential inhibitory compound, and these are discussed supra and further illustrated by means of Examples provided below. All of the reagents including, primary binding partners, secondary binding partners, colorimetric dyes and buffers are known in the art and availably commercially to one of skill in this art.

This invention is further directed to a screening kit comprising a multiplicity of recombinant Jak3 proteins and instructions to, screen for a compound that inhibits Jak3 autophosphorylation and screen for a compound or biomolecule that binds Jak3 or truncated Jak3 or phosphorylated Jak3 or phoshorylated truncated Jak3. In a preferred embodiment, the recombinant Jak3 protein has a sequence shown in SEQ ID NO: 6, recombinant reporter-Jak3 fusion protein has a sequence shown in SEQ ID NO: 7, recombinant reporter-truncated-Jak3 fusion proteins discussed supra have sequences shown in SEQ ID NO: 8-10, the recombinant phosphorylated reporter-Jak3 fusion protein has a sequence shown in SEQ ID NO: 11, the recombinant phosphorylated reporter-truncated-Jak3 fusion proteins discussed supra have sequences shown in SEQ ID NO: 12-13, The instructions provide methods to perform, the Jak3 autophosphorylation assay in the presence of the potential inhibitory compound, and the non-phosphorylated and phosphorylated Jak3 or truncated-Jak3 binding assay in the presence of the potential binding compound, and these are discussed supra and further illustrated by means of Examples provided below. All of the reagents including, primary binding partners, secondary binding partners, colorimetric dyes and buffers are known in the art and availably commercially to one of skill in this art.

The following examples are given for the purpose of illustrating various embodiments of the invention and are not meant to limit the present invention in any fashion.

EXAMPLE 1

Materials

ELISA multiplates, horseradish peroxidase (HRP)-conjugated secondary antibody, and 3,3,5,5-tetramethylbenzidine substrate kit were purchased from Thermo Scientific (Waltham, Mass.). Adenosine triphosphate, β-D-1-thiogalactopyranoside, indoleacrylic acid and buffers were purchased from Sigma-Aldrich (S. Louis Mo.), pY20 monoclonal antibody to phosphorylated tyrosine was purchased from MP Biomedical (Santa Ana, Calif.), pGEX-4T vector was purchased from GE Healthcare. pGEX2T was purchased from Addgene. BL21 and TKX1 competent cells were from Agilent Technologies (Santa Clara Calif.).

EXAMPLE 2

Expression and Purification of Recombinant Proteins and Recombinant Phosphorylated Proteins GST-tagged wild type and truncated, mutant Jak3 cDNAs having SEQ ID NO: 1 (FIG. 1A), SEQ ID NO: 2 (FIG. 1B), SEQ ID NO: 3 (FIG. 1C), SEQ ID NO: 4 (FIG. 1D) and SEQ ID NO: 5 (FIG. 1E) were cloned (26) in a pGEX-4T vector. Proteins and fusion proteins having amino acid sequences having SEQ ID NO: 6 (FIG. 2A), SEQ ID NO: 7 (FIG. 2B), SEQ ID NO: 8 (FIG. 2C), SEQ ID NO: 9 (FIG. 2D) and SEQ ID NO: 10 (FIG. 2E) were expressed using an *E. coli*, BL21 protein expression system, by induction using Isopropyl β-D-1-thiogalactopyranoside. Recombinant phosphorylated Jak3 (P-Jak3) proteins having SEQ ID NO: 11 (FIG. 2B), SEQ ID NO: 12 (FIG. 2C), SEQ ID NO: 13 (FIG. 2D) were obtained by expression in a *E. coli*, TKX1 protein expression system, using a two-step induction method with β-D-1-thiogalactopyranoside and indoleacrylic acid as described (27). FIG. 3A shows by immunoblotting that while recombinant Jak3 protein is expressed in both BL21 and TKX1 cells, only the protein expressed in the later is phosphorylated.

Recombinant cytoskeletal protein, Villin was cloned in the prokaryotic expression vector pGEX2T, expressed using a BL21 expressing system and purified as reported before (28). Phosphorylated (P) Villin was generated by cloning and expression in a *E. coli*, TKX1 protein expression system, as described supra.

Recombinant adapter protein, p52ShcA was cloned in the pGEX2T vector and the protein expressed using an *E. coli*, BL21 protein expression system as described supra. The phosphorylated form of this protein, P-p52ShcA was generated by cloning and expression in a *E. coli*, TKX1 protein expression system, as described supra.

FIG. 3B shows immunoblotting (IB) analyses of the purified recombinant wild type and fusion proteins expressed in *E. coli* BL21, using GST antibody. Arrows indicate recombinant proteins.

EXAMPLE 3

Kinetics of Jak3 Autophosphorylation

To determine whether the non-phosphorylated form of Jak3 was functionally active, a phosphorylation assay was performed in the presence of a phosphate donor, to test the ability of Jak3 to phosphorylate itself. Jak3 was contacted with the phosphate donor, adenosine triphosphate (ATP) for different times ranging from 0 min to 200 minutes. The level of phosphorylated Jak3 (P-Jak3) was then measured by multiplate ELISA, using the phospho-tyrosine specific antibody, pY20, as the primary binding partner. FIG. 4 shows that Jak3 is rapidly autophosphorylated in a time dependent manner by the addition of ATP, with a half time maximum ($t_{1/2}$) value of 135 s.

Screening of CP-690505 as a Potential Inhibitor of Jak3 Autophosphorylation

Figure 5:
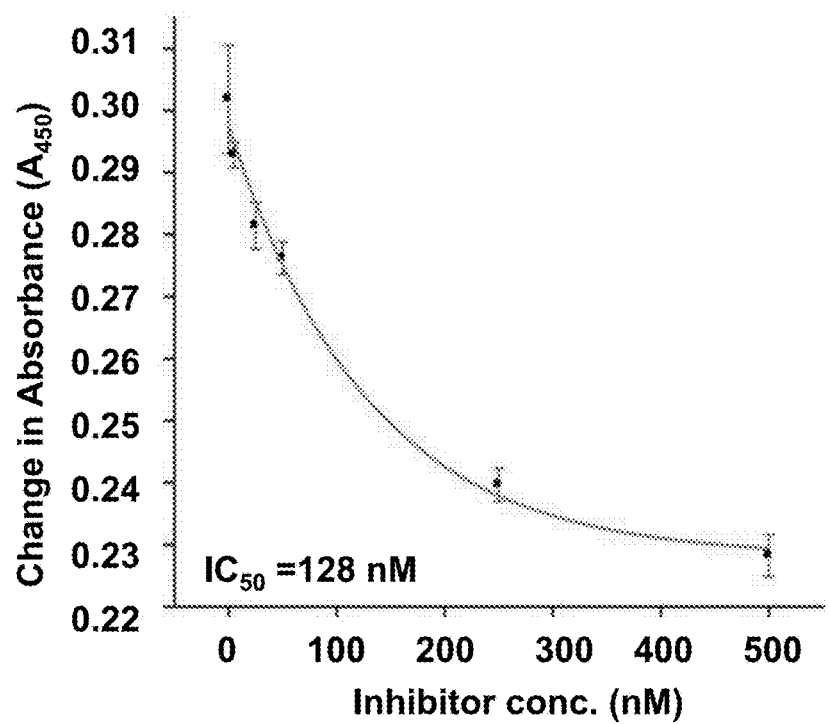
FIG. 5 shows inhibition of GST-WT-Jak3 autophosphorylation in the presence or absence of different concentrations of the Jak3 inhibitor, CP-690505 ranging from 0 nM to 500 nM. pY20 antibody was used as the primary binding partner.

To test the utility of this invention to screen for inhibitors of Jak3 autophosphorylation, in the absence of additional substrates, recombinant non-phosphorylated Jak3 purified from BL21 cells were contacted with CP-690505, in the absence (control sample) or presence (test sample) of the phosphate donor, ATP. The level of P-Jak3 was determined by an ELISA-based multiplate assay, using the phospho-tyrosine specific pY20 antibody as primary binding partner, horse radish peroxidase conjugated antibody as the secondary binding partner and 3,3',5,5'-tetramethylbenzidine as the colorimetric substrate. Raw absorbance data for the control samples were subtracted from the absorbance for the test samples to obtain the corrected absorbance values. FIG. 5 shows a CP-690505 concentration dependent decrease in the level of P-Jak3, with an $IC_{50}$ value of 128 nM, in agreement with an established function for CP-690505 as an inhibitor of Jak3 phosphorylation (29).

EXAMPLE 4

P-Jak3 Binds to the Cytoskeletal Protein P-Villin

Figure 6A:
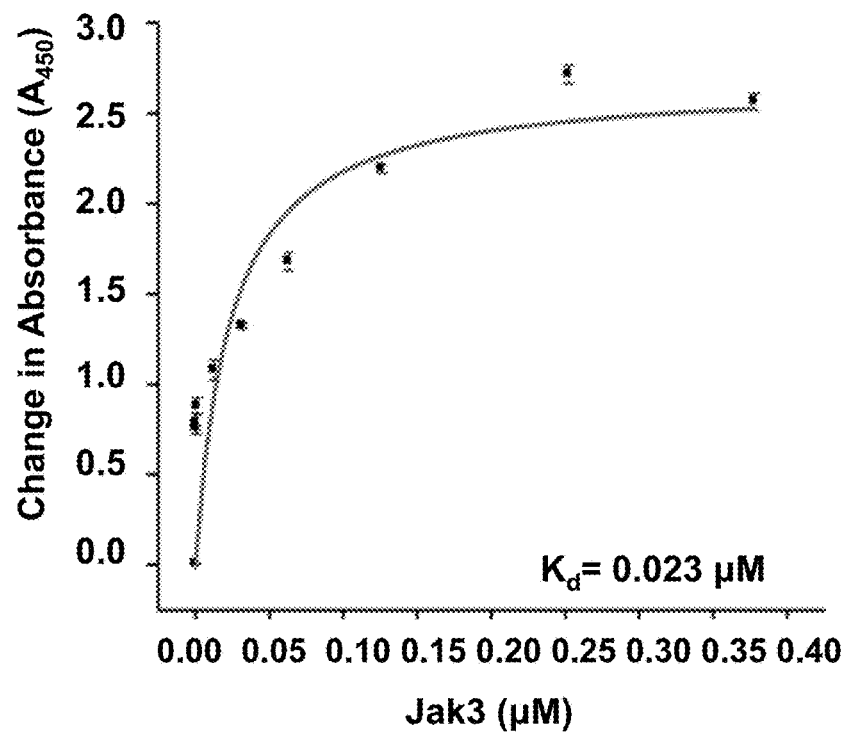
FIGS. 6A-6B shows binding profile for Jak3-Villin interactions by multiplate ELISA assay and the calculation of binding parameters.
Figure 6B:
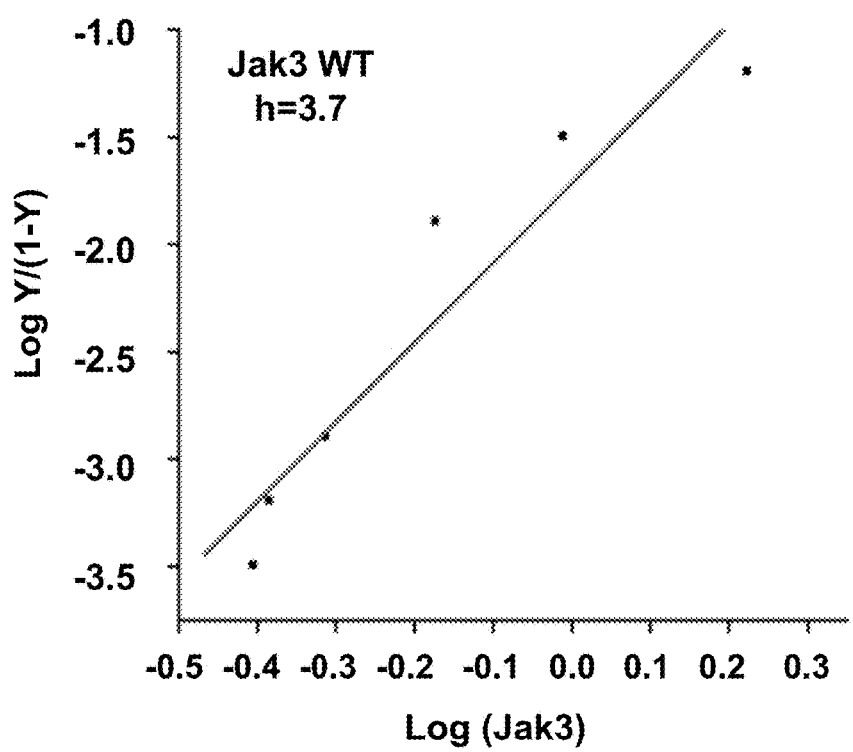

To determine the ability of Jak3 to interact with natural compounds including biomolecules, binding studies were performed in a multiplate using the cytoskeletal protein, Villin, known in the art to be a substrate for P-Jak3. Multiplates pre-coated with P-Villin were contacted with increasing concentrations of GST-P-Jak3 fusion protein (test samples) or GST alone (control sample). Binding levels were measured using GST antibody as the primary binding partner, horse radish peroxidase conjugated antibody as the secondary binding partner and 3,3',5,5'-tetramethylbenzidine as the colorimetric substrate. Raw absorbance data for the control samples were subtracted from the absorbance for the test samples to obtain the corrected absorbance values. FIG. 6A shows an increase in the level of binding as measured by the corrected absorbance, as a function of P-Jak3 concentration ranging from 0-400 nM, with a dissociation constant ($K_d$) of 23 nM. FIG. 6B shows a rearranged Hill equation plot (30), which shows the relationship between log $Y/(1-Y)$ and log (Jak3), where Y is the fractional saturation of absorbance. The Hill coefficient (h) is determined to be 3.7, suggestive of positive cooperative binding.

P-Jak3 Interacts to the Adapter Protein P-p52ShcA

Figure 7A:
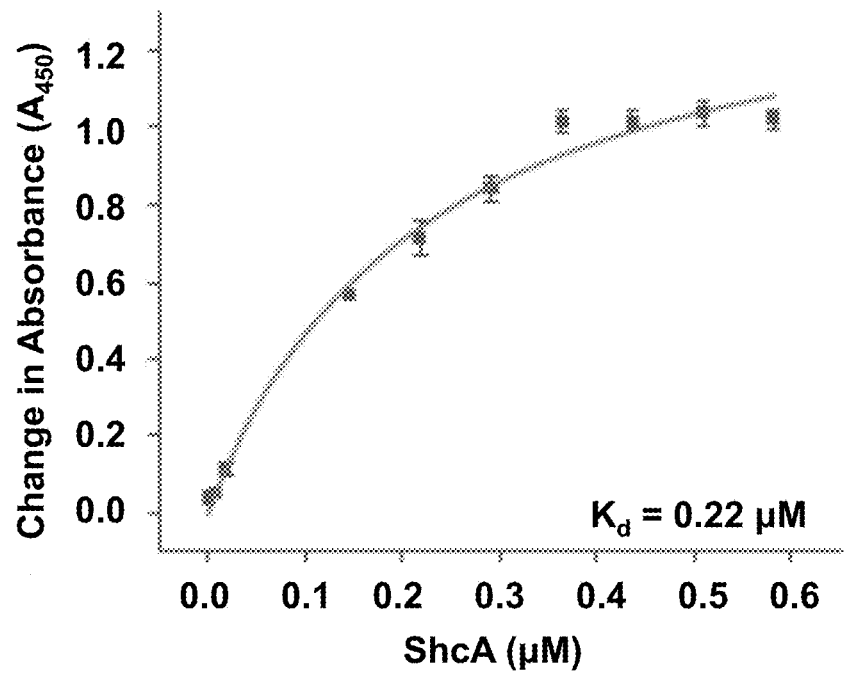
FIGS. 7A-7B shows binding profile for Jak3-p52ShcA interactions by multiplate ELISA assay and the calculation of binding parameters.
Figure 7B:
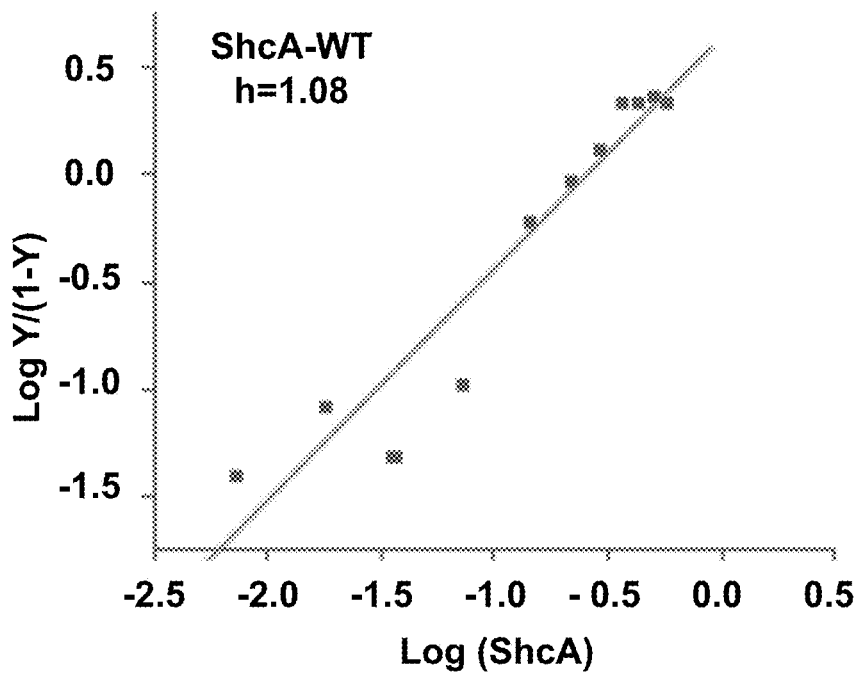

To further establish the utility of this screening method, the ability of Jak3 to bind the phosphorylated adapter molecule, P-p52ShcA was determined by performing the multiplate assay as described supra with the exception that the P-Villin was replaced with P-p52ShcA in the pre-coating step. FIG. 7A shows an increase in the level of binding of P-Jak3 with P-p52ShcA, as a function of P-Jak3 concentration (0-600 nM). The dissociation constant ($K_d$) of this binding was found to be 220 µM, which is about 10 fold weaker compared to P-Jak3 binding with P-Villin (FIG. 6A). Analysis of these data using a rearranged Hill equation plot as described supra, revealed a Hill coefficient (h) value of 1.08 (FIG. 7B) that is suggestive of non-cooperative binding, which is also distinct from the data obtained using P-Villin as the binding compound.

The use of internal controls in the screening method of this invention is advantageous, as it eliminates ambiguity in interpreting raw absorbance values, allowing the end user to compare binding parameters for a plurality of compounds screened on different multiplates and in different multiplate formats. Moreover, the data discussed above underscore the advantages of using this screening method as a high-throughput analysis tool for scoring a plurality of potential binding compounds, based on their binding affinities and Hill parameters, allowing the end user to rapidly select compounds for any desired application including, preclinical, clinical and, research and development.

EXAMPLE 5

FERM Domain of Jak3 is Sufficient for Interactions Between Jak3 and Villin

Figure 8A:
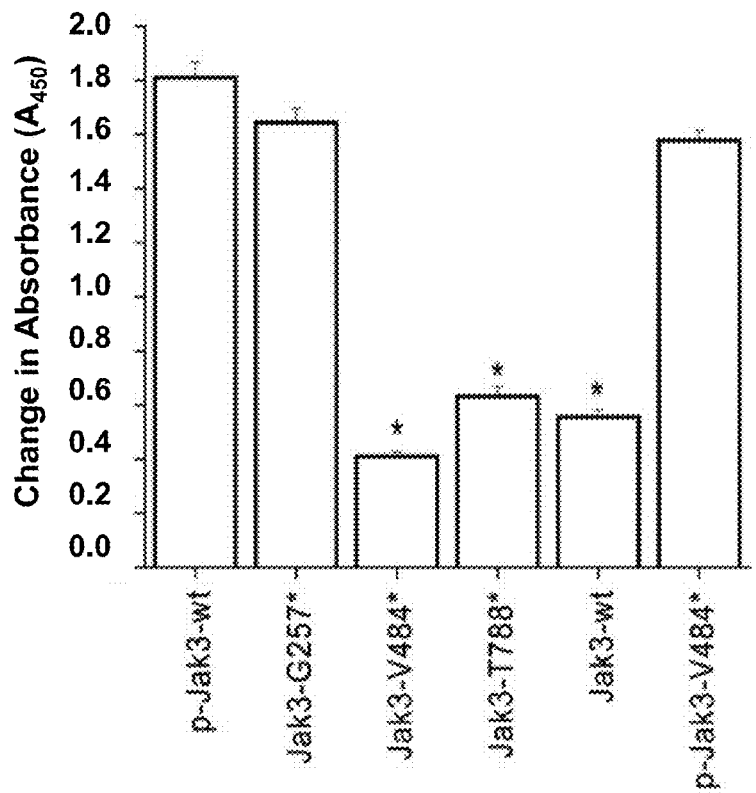
FIGS. 8A-8B shows binding of recombinant truncated-Jak3 proteins with Villin by multiplate ELISA assay and the calculation of binding parameters.
Figure 8B:
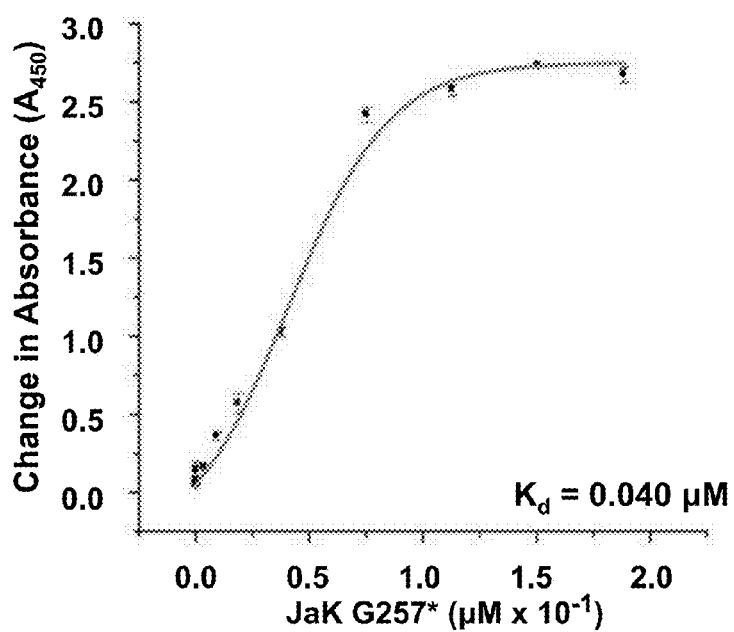

To determine whether the kinase domains of Jak3 are critical for Villin binding, recombinant GST-truncated-Jak3 fusion proteins shown in FIGS. 2C-2E were expressed in BL21 (for non-phosphorylated proteins) or TKX1 (for phosphorylated proteins) cells, and purified. Multiplates pre-coated with P-Villin were contacted with these GST-tagged recombinant truncated-Jak3 or with GST-tagged recombinant WT-Jak3, and binding measured as described supra. FIG. 8A shows that, among the various proteins tested, Jak3-G257 (SEQ ID NO. 10), which contains the FERM domain alone, but not the inhibitory SH2 domain, bound P-Villin at approximately the same level as P-WT-Jak3. The dissociation constant ($K_d$) value for Jak3-G257 was found to be 40 nM (FIG. 8B) compared to a value of 23 nM for P-WT-Jak3 (FIG. 6A)

Figure 9:
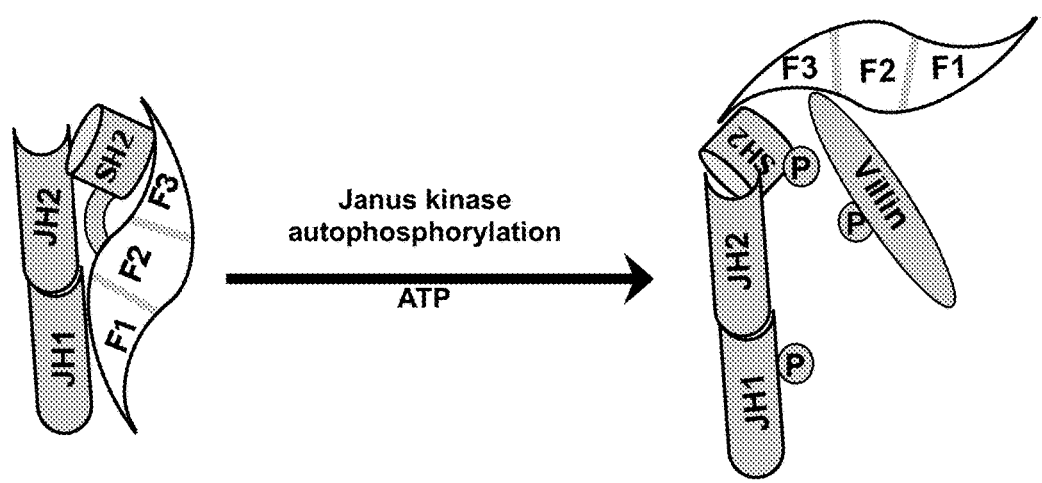
FIG. 9 shows a working model for Jak3 binding with Villin. Tyrosine phosphorylation of the SH2 domain of Jak3 disrupts the interactions between the Jak3-FERM domain and Jak3-SH2 domain, making the F3 subdomain of the FERM domain available to interact with phosphorylated Villin.

FIG. 8A also shows that the recombinant non-phosphorylated Jak3 proteins, Jak-V484 (SEQ ID NO. 9), Jak3-T788 (SEQ ID NO. 8) and WT-Jak3 (SEQ ID NO. 7) displayed relatively lower level of binding, though the level of binding is above the GST-alone controls (subtracted values are shown in FIG. 8A). P-Jak-V484 bound P-Villin at approximately the same level as P-WT-Jak3 and Jak3-G257 because the inhibitory property of SH2 domain being annulled due to phosphorylation (FIG. 9).

The following references are cited herein:
1. Safford, et al., (1997). *Exp Hemato.* 25, 374-386.
2. O'Shea, et al., (2002). *Nat Rev Immuno.* 2, 37-45.
3. Ferrari-Lacraz, et al., (2004). *J Immuno* 173, 5818-5826.
4. Townsend, et al., (2000). *Immunity* 13, 573-583.
5 Malaviya, et al., (1999). *J Biol Chem* 274, 27028-27038.
6. Klink, et al., (2012). *Immuno/Invest* 41,382-398.
7. Yoo, et al., (2011). *Cancer Res Treat* 43, 108-116.
8. Ye, et al., (2013). *J Mol Biol* 425, 755-766.
9. Tian, et al., (1998). *Immunological reviews* 164, 119-127.

10. Macchi, et al., (1995). *Nature* 377, 65-68.
11. Cetkovic-Cvrlje, et al., (2003). *Clin Immuno* 106, 213-225.
12. Tortolani, et al., (1995). *J Immuno* 155, 5220-5226.
13. Ward, et al., (2000). *Blood* 95, 19-29.
14. Changelian, et al., (2003). *Science* 302, 875-878.
15. Hall, B. M. (1991). *Transplantation* 51, 1141-1151.
16. Stepkowski, et al., (2002). *Blood* 99,680-689.
17. Saemann, et al., (2003). *American journal of transplantation* 3, 1341-1349.
18. Cetkovic-Cvrlje, M., and Tibbles, H. E. (2004). *Curr Pharm Des* 10, 1767-1784.
19. Takahashi, T., and Shirasawa, T. (1994). *FEBS Lett* 342, 124-128.
20. Mishra, et al., (2013). *J Biol Chem* 288,31795-31806
21. Cornejo, et al., (2009). *Int J Biochem Cell Biol* 41,2376-2379
22. Un, et al., (2005). *Am J Pathol* 167, 969-980.
23. Girault, et al., (1999). *Trends Biochem Sci* 24, 54-57.
24. Zhou, et al., (2001). *Mol Celi* 8, 959-969.
25. Mohanty, A., Wiener M. (2004). *Protein Expr Purif.* 33, 311-25.
26. Zhou, et al., (1997). *Proc. Natl. Acad. Sci. U.S.A.* 94, 13850-13855.
27. Mishra, J. and Kumar, N. (2014). *J. Biol. Chem.* 289, 15951-15956.
28. Kumar, et al., (2004). *J. Biol. Chem.* 279, 3096-3110.
29. Chrencik, et al., (2010). *J. Mol. Biol.* 400, 413-433.
30. Ferrary, et al., (1999). *J. Cell Biol.* 146, 819-830

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. The terms in the claims have their plain, ordinary meaning unless otherwise explicitly and clearly defined by the patentee.

What is claimed is:

1. A method for screening for a compound that inhibits Janus kinase 3 (Jak3) protein, comprising the steps of:
   selecting a potential inhibitory compound;
   contacting, a phosphate donor with a recombinant Jak3 protein and the potential inhibitory compound in a first sample;
   contacting said phosphate donor with the recombinant Jak3 protein in a second control sample wherein the recombinant Jak3 protein has a sequence of SEQ ID NO. 6 or SEQ ID No. 7;
   measuring a level of autophosphorylation of said Jak3 protein in the first sample and in the second sample;
   wherein a reduction in the level of Jak3 autophosphorylation in the first sample compared to the level in the second control sample indicates that the compound inhibits Jak3 protein.

2. The method of claim 1, wherein the recombinant Jak3 protein is a reporter-Jak3 fusion protein.

3. The method of claim 2, wherein the reporter protein is Glutathione-S-transferase (GST).

4. The method of claim 1, wherein the phosphate donor is adenosine triphosphate.

5. The method of claim 1, wherein the level of Jak3 phosphorylation is measured by ELISA.

6. The method of claim 5, wherein the primary antibody for ELISA is a monoclonal phosphorylated-Jak3 specific antibody.

7. The method of claim 1 wherein the compound is a biomolecule.

8. A method for screening for a compound that binds Jak3 protein comprising the steps of:
   selecting a potential binding compound;
   contacting a recombinant Jak3 fusion protein or a recombinant phosphorylated Jak3 fusion protein comprising a reporter protein with the potential binding compound in a first sample;
   contacting said reporter protein with the potential binding compound in a second control sample wherein the recombinant Jak3 fusion protein has a sequence of SEQ ID NO. 6 or SEQ ID No. 7;

measuring a level of binding in the first sample and in the second control sample; wherein an increase in the level of binding of the potential binding compound in the first sample compared to the level of binding in the second control sample indicates that the compound binds Jak3 protein.

9. The method of claim 8, wherein the reporter protein is Glutathione-S-transferase (GST).

10. The method of claim 8, wherein the recombinant Jak3 fusion protein or the recombinant phosphorylated Jak3 fusion protein comprises a truncated Jak3 protein sequence.

11. The method of claim 10, wherein the recombinant truncated Jak3 fusion protein has a sequence shown in SEQ ID NO: 8, SEQ ID NO: 9 or SEQ ID NO: 10.

12. The method of claim 10, wherein the recombinant phosphorylated truncated-Jak3 fusion protein has a sequence shown in SEQ ID NO: 12 or SEQ ID NO: 13.

13. The method of claim 8, wherein the level of binding is measured by ELISA.

14. The method of claim 13, wherein the primary antibody for ELISA is a monoclonal GST specific antibody.

15. The method of claim 8 wherein the compound is a biomolecule.

\* \* \* \* \*